US010543192B2

(12) United States Patent
Statler et al.

(10) Patent No.: US 10,543,192 B2
(45) Date of Patent: *Jan. 28, 2020

(54) GLYCOPYRROLATE SALTS

(71) Applicant: Dermira, Inc., Menlo Park, CA (US)

(72) Inventors: John Allan Statler, Redwood City, CA (US); Anthony Adrian Shaw, North Vancouver (CA); Delphine Caroline Imbert, Cupertino, CA (US); Jennifer Leigh Nelson, Kokomo, IN (US); Patricia Andres, West Lafayette, IN (US); Lisa Lynn McQueen, West Lafayette, IN (US); Stephan Xander Mattheus Boerrigter, West Lafayette, IN (US); Jon Gordon Selbo, West Lafayette, IN (US); Mark Christopher Andres, West Lafayette, IN (US)

(73) Assignee: Dermira, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/996,353

(22) Filed: Jun. 1, 2018

(65) Prior Publication Data

US 2018/0271833 A1  Sep. 27, 2018

Related U.S. Application Data

(63) Continuation of application No. 15/438,636, filed on Feb. 21, 2017, now Pat. No. 10,004,717, which is a continuation of application No. 14/989,995, filed on Jan. 7, 2016, now Pat. No. 9,610,278, which is a continuation of application No. 14/643,553, filed on Mar. 10, 2015, now Pat. No. 9,259,414, which is a continuation of application No. 14/473,537, filed on Aug. 29, 2014, now Pat. No. 9,006,462, which is a continuation of application No. PCT/US2014/019552, filed on Feb. 28, 2014, which is a continuation-in-part of application No. 14/024,480, filed on Sep. 11, 2013, now Pat. No. 9,006,461, which is a continuation-in-part of application No. 14/024,484, filed on Sep. 11, 2013, now Pat. No. 8,859,610, which is a continuation of application No. 13/781,390, filed on Feb. 28, 2013, now Pat. No. 8,558,008, and a continuation of application No. 13/781,390, filed on Feb. 28, 2013, now Pat. No. 8,558,008.

(60) Provisional application No. 61/770,925, filed on Feb. 28, 2013, provisional application No. 61/770,920, filed on Feb. 28, 2013.

(51) Int. Cl.
| | | |
|---|---|---|
| *C07D 207/12* | (2006.01) | |
| *A61K 31/40* | (2006.01) | |
| *A61K 9/00* | (2006.01) | |
| *A61K 9/08* | (2006.01) | |
| *A61K 47/10* | (2017.01) | |
| *A61K 47/12* | (2006.01) | |
| *A61K 47/32* | (2006.01) | |
| *A61K 47/34* | (2017.01) | |

(52) U.S. Cl.
CPC ............ *A61K 31/40* (2013.01); *A61K 9/0014* (2013.01); *A61K 9/08* (2013.01); *A61K 47/10* (2013.01); *A61K 47/12* (2013.01); *A61K 47/32* (2013.01); *A61K 47/34* (2013.01); *C07D 207/12* (2013.01)

(58) Field of Classification Search
CPC .................................................. C07D 207/12
See application file for complete search history.

(56) References Cited

U.S. PATENT DOCUMENTS

| | | |
|---|---|---|
| 2,956,062 A | 10/1960 | Lunsford |
| 4,372,098 A | 2/1983 | Mason |
| 4,824,676 A | 4/1989 | Bodor |
| 4,849,224 A | 7/1989 | Chang et al. |
| 4,885,282 A | 12/1989 | Thornfeldt |
| 4,891,227 A | 1/1990 | Thaman et al. |
| 4,891,228 A | 1/1990 | Thaman et al. |
| 4,899,739 A | 2/1990 | Konishi |
| 4,977,138 A | 12/1990 | Okuhara |
| 4,983,395 A | 1/1991 | Chang et al. |
| 5,008,111 A | 4/1991 | Bodor |
| 5,122,383 A | 6/1992 | Heiber et al. |
| 5,198,567 A | 3/1993 | Lang et al. |
| 5,290,961 A | 3/1994 | Okamoto et al. |
| 5,338,874 A | 8/1994 | Nakanishi et al. |
| 5,352,456 A | 10/1994 | Fallon et al. |
| 5,370,917 A | 12/1994 | Niitsuma et al. |
| 5,403,588 A | 4/1995 | Santa Ana, Jr. |
| 5,409,946 A | 4/1995 | Garvey et al. |

(Continued)

FOREIGN PATENT DOCUMENTS

| | | |
|---|---|---|
| EP | 1 616 567 A1 | 1/2006 |
| GB | 1080960 | 8/1967 |

(Continued)

OTHER PUBLICATIONS

"Robinul Injection (Glycopyrrolate Injection, USP)," *FDA Label*, pp. 3-11.
"USP Glycopyrrolate," The United States Pharmacopeia) Convention, 3170-3173, Dec. 1, 2014.
Abell et al., "The Treatment of Idiopathic Hyperhidrosis by Glycopyrronium Bromide and Tap Water Iontophoresis," *British Journal of Dermatology*, 91:87-91 (1974).
Allmendinger et al., "Carry Over of Impurities: A Detailed Exemplification for Glycopyrrolate (NVA237)", Org. Process. Dev., (2012), vol. 16, pp. 1754-1769.
Anonymous Third Party Observations dated Apr. 7, 2017 for EP application No. 14716654.0, 7 pages.

(Continued)

*Primary Examiner* — Shawquia Jackson
(74) *Attorney, Agent, or Firm* — Squire Patton Boggs (US) LLP

(57) ABSTRACT

Salts of glycopyrrolate, including solid forms and formulations such as topicals thereof, are disclosed. Methods of making glycopyrrolate salts, including formulations such as topicals thereof, and methods of treating hyperhidrosis with salts of glycopyrrolate, and formulations such as topicals thereof, are disclosed.

41 Claims, 45 Drawing Sheets

(56) References Cited

U.S. PATENT DOCUMENTS

| | | | |
|---|---|---|---|
| 5,420,319 A | 5/1995 | Okamoto et al. |
| 5,446,070 A | 8/1995 | Mantelle |
| 5,460,820 A | 10/1995 | Ebert et al. |
| 5,472,958 A | 12/1995 | Gunn, Jr. et al. |
| 5,525,347 A | 6/1996 | Kellner et al. |
| 5,612,324 A | 3/1997 | Guang Lin et al. |
| 5,616,337 A | 4/1997 | Kasianovitz et al. |
| 5,620,694 A | 4/1997 | Girardot |
| 5,635,203 A | 6/1997 | Gale et al. |
| 5,641,507 A | 6/1997 | Devillez |
| 5,670,524 A | 9/1997 | Eek |
| 5,733,912 A | 3/1998 | Wasicak et al. |
| 5,744,151 A | 4/1998 | Capelli |
| 5,750,137 A | 5/1998 | Taskovich et al. |
| 5,820,875 A | 10/1998 | Fallon et al. |
| 5,834,489 A | 11/1998 | Eek |
| 5,919,471 A | 7/1999 | Saferstein et al. |
| 5,919,760 A | 7/1999 | Simon |
| 5,962,505 A | 10/1999 | Bobrove et al. |
| 5,976,499 A | 11/1999 | Rubenstein et al. |
| 5,996,797 A | 12/1999 | Flaig |
| 6,036,964 A | 3/2000 | Guertin et al. |
| 6,040,344 A | 3/2000 | Gao et al. |
| 6,063,808 A | 5/2000 | Fabiano et al. |
| 6,074,630 A | 6/2000 | Devillez et al. |
| 6,114,346 A | 9/2000 | Harris et al. |
| 6,127,353 A | 10/2000 | Yuen et al. |
| 6,133,253 A | 10/2000 | Holladay et al. |
| 6,165,500 A | 12/2000 | Cevc |
| 6,183,455 B1 | 2/2001 | Gerstenberger et al. |
| 6,203,810 B1 | 3/2001 | Alemany et al. |
| 6,204,285 B1 | 3/2001 | Fabiano et al. |
| 6,214,792 B1 | 4/2001 | Simon |
| 6,265,414 B1 | 7/2001 | Harris et al. |
| 6,307,060 B1 | 10/2001 | Noe et al. |
| 6,358,516 B1 | 3/2002 | Harod |
| 6,395,757 B1 | 5/2002 | Bobrove et al. |
| 6,433,003 B1 | 8/2002 | Bobrove et al. |
| 6,436,417 B1 | 8/2002 | Singh et al. |
| 6,446,795 B1 | 9/2002 | Allen et al. |
| 6,471,986 B1 | 10/2002 | Cline et al. |
| 6,472,563 B1 | 10/2002 | Tanoury et al. |
| 6,537,576 B1 | 3/2003 | Lindahl et al. |
| 6,613,795 B2 | 9/2003 | Noe et al. |
| 6,716,805 B1 | 4/2004 | Sherry et al. |
| 6,720,453 B2 | 4/2004 | Tanoury et al. |
| 6,743,433 B2 | 6/2004 | Perricone |
| 6,780,877 B2 | 8/2004 | Kita et al. |
| 6,790,435 B1 | 9/2004 | Ma et al. |
| 7,060,289 B2 | 6/2006 | Wassenaar |
| 7,145,036 B2 | 12/2006 | Tanoury et al. |
| 7,253,182 B2 | 8/2007 | Noe et al. |
| 7,358,204 B2 | 4/2008 | Brennan |
| 7,569,598 B2 | 8/2009 | Noe et al. |
| 7,608,280 B2 | 10/2009 | Ueda et al. |
| 7,611,724 B2 | 11/2009 | Ueda et al. |
| 7,754,240 B2 | 7/2010 | Staniforth et al. |
| 7,838,447 B2 | 11/2010 | Clark et al. |
| 7,872,019 B2 | 1/2011 | Lohray et al. |
| 7,915,303 B2 | 3/2011 | Baxter |
| 8,101,646 B2 | 1/2012 | Weeratunga et al. |
| 8,114,900 B2 | 2/2012 | Ini et al. |
| 8,252,316 B2 | 8/2012 | Wassenaar |
| 8,278,339 B2 | 10/2012 | Marti et al. |
| 8,278,461 B2 | 10/2012 | Thaper et al. |
| 8,558,008 B2 | 10/2013 | Statler et al. |
| 8,618,160 B2 | 12/2013 | Johnston et al. |
| 8,679,524 B2 | 3/2014 | Wassenaar |
| 8,859,610 B2 | 10/2014 | Statler et al. |
| 9,006,461 B2 | 4/2015 | Statler et al. |
| 9,006,462 B2 | 4/2015 | Statler et al. |
| 9,034,368 B2 | 5/2015 | Wassenaar |
| 9,259,414 B2 | 2/2016 | Statler et al. |
| 9,610,278 B2 | 4/2017 | Statler et al. |
| 9,744,105 B2 | 8/2017 | Johnston et al. |
| 10,004,717 B2 | 6/2018 | Statler et al. |
| 10,052,267 B2 | 8/2018 | Johnston et al. |
| 2001/0031787 A1 | 10/2001 | Hsu et al. |
| 2002/0037264 A1 | 3/2002 | Burry et al. |
| 2002/0173536 A1 | 11/2002 | Noe et al. |
| 2003/0064040 A1 | 4/2003 | Lukacsko |
| 2004/0209954 A1 | 10/2004 | Lukacsko |
| 2006/0069073 A1 | 3/2006 | Pieper et al. |
| 2006/0167275 A1 | 7/2006 | Noe et al. |
| 2006/0211729 A1 | 9/2006 | Fyrnys et al. |
| 2007/0167496 A1 | 7/2007 | Karl et al. |
| 2007/0185067 A1 | 8/2007 | Roscher et al. |
| 2007/0253911 A1 | 11/2007 | Tamarkin et al. |
| 2008/0063719 A1 | 3/2008 | Morton et al. |
| 2008/0227988 A1 | 9/2008 | Baxter et al. |
| 2008/0267886 A1 | 10/2008 | Collingwood |
| 2008/0279948 A1 | 11/2008 | Collingwood et al. |
| 2008/0286363 A1 | 11/2008 | Collingwood et al. |
| 2008/0292560 A1 | 11/2008 | Tamarkin et al. |
| 2008/0292562 A1 | 11/2008 | Pieper et al. |
| 2008/0300226 A1 | 12/2008 | Goede et al. |
| 2008/0317832 A1 | 12/2008 | Dillaha |
| 2008/0317862 A1 | 12/2008 | Collingwood et al. |
| 2009/0005577 A1 | 1/2009 | Kraiouchkine |
| 2009/0062372 A1 | 3/2009 | Baxter |
| 2009/0208437 A1 | 8/2009 | Woehrmann et al. |
| 2010/0166671 A1 | 7/2010 | Collingwood et al. |
| 2010/0184727 A1 | 7/2010 | Roach et al. |
| 2010/0276329 A1 | 11/2010 | Johnston et al. |
| 2011/0305645 A1 | 12/2011 | Pivetti et al. |
| 2011/0306650 A1 | 12/2011 | Pivetti et al. |
| 2013/0211101 A1 | 8/2013 | Statler et al. |
| 2018/0311116 A1 | 11/2018 | Johnston et al. |

FOREIGN PATENT DOCUMENTS

| | | |
|---|---|---|
| WO | WO 86/02272 | 4/1986 |
| WO | WO 1995/009006 A1 | 4/1995 |
| WO | WO 98/00109 A1 | 1/1998 |
| WO | WO 98/00132 A1 | 1/1998 |
| WO | WO 98/06260 | 2/1998 |
| WO | WO 1998/058631 A1 | 12/1998 |
| WO | WO 1999/066793 A1 | 12/1999 |
| WO | WO 2000/035327 A1 | 6/2000 |
| WO | WO 00/45798 | 8/2000 |
| WO | WO 2000/069483 A1 | 11/2000 |
| WO | WO 2000/073552 A1 | 12/2000 |
| WO | WO 2001/008681 A1 | 2/2001 |
| WO | WO 2001/010427 A2 | 2/2001 |
| WO | WO 2001/035883 A1 | 5/2001 |
| WO | WO 2001/035906 A2 | 5/2001 |
| WO | WO 2002/034224 A1 | 5/2002 |
| WO | WO 2003/011340 A1 | 2/2003 |
| WO | WO 03/092641 | 11/2003 |
| WO | WO 2006/100453 A1 | 9/2006 |
| WO | WO 2009/051818 A1 | 4/2009 |
| WO | WO 2009/142589 A1 | 11/2009 |
| WO | WO 2010/115937 A1 | 10/2010 |
| WO | WO 2011/157536 A1 | 12/2011 |

OTHER PUBLICATIONS

Atkin et al., "Treatment of Diabetic Gustatory Sweating with Topical Glycopyrrolate Cream," *Diabetic Medicine*, 13:493-494 (1996).

Attwood, "Micellar and Nonmicellar Association of Antiacetylcholine Drugs in Aqueous Solution," *The Journal of Physical Chemistry*, 80(18):1984-1987 (1976).

Breezhaler, EMA, Assessment report, 2012, 84 pages.

Communication Pursuant to Rule 114(2) EPC dated Nov. 23, 2017 for EP application No. 14716654.0, 5 pages.

D. J. Snodin, "Residues of genotoxic alkyl mesylates in mesylate salt drug substances: Real or imaginary problems?", *Regulatory Toxicology and Pharmacology*, 2006, vol. 45, pp. 79-90.

Guy et al., "Stereochemistry of Anticholinergic Agents. Part II. Crystal and Molecular Structure of Glycopyrronium Bromide," *J. Chem. Soc., Perkin Trans.* 2, 1875-1879 (1973).

(56) References Cited

OTHER PUBLICATIONS

Hays et al., "The Frey Syndrome: A Simple, Effective Treatment," *OtolaryngoL Head Neck Surg.*, 90:419-425 (1982).
Hays, "The Frey Syndrome: A Review and Double Blind Evaluation of the Topical Use of a New Anticholinergic Agent," *The Laryngoscope*, 88:1796-1824 (1978).
Ingallinera et aL, "Compatibility of Glycopyrrolate Injection and Commonly Used Infusion Solutions and Additives," *Am. J. Hosp. Pharm.*, 36:508-510 (1979).
International Search Report and Written Opinion of the International Searching Authority dated Jul. 2, 2014, in International Patent Application No. PCT/US2014/019552.
Juniper, Jr., et al., "Finger-Tip Sweat-Gland Activity and Salivary Secretion as Indices of Anticholinergic Drug Effect," *American Journal of Digestive Diseases*, 9(1):31-42 (1964).
Kavanagh et al., "Topical glycopyrrolate should not be overlooked in treatment of focal hyperhidrosis", *British Journal of Dermatology*, 2006, vol. 155, p. 487.
Klaber et al., "Anticholinergic Drugs Were Not Mentioned ," *Letters to the Editor*, BMJ, 321:702-703 (2000).
Luh et al., "Craniofacial Hyperhidrosis Successfully Treated with Topical Glycopyrrolate," *Southern Medical Journal*, 95(7):756-758 (2002).
May et al., "Frey's Syndrome: Treatment with Topical Glycopyrrolate," *Head & Neck*, pp. 85-89 (1989).
Mirakhur et al., "Evaluation of the Anticholinergic Actions of Glycopyrronium Bromide," *Br. J. din. Pharmac.*, 5:77-84 (1978).
Mirakhur et al., "Minireview—Glycopyrrolate," *Gen. Pharmac.*, 12:423-427 (1981).
Ording et al., "Glykopyrron (Robinul)," Videnskab OG Praksis, 3389-3390 (1984) with machine translation.
Sessions et al., "Frey's Syndrome—A Technical Remedy," *Ann. Otol.*, 85:734-739 (1976).
Seukeran et al., "The Use of Topical Glycopyrrolate in the Treatment of Hyperhidrosis," *Clinical and Experimental Dermatology*, 23:204-205 (1998).
Shaw et al., "A Randomised Controlled Trial of Topical Glycopyrrolate, the First Specific Treatment for Diabetic Gustatory Sweating," *Diabetologia*, 40:299-301 (1997).
Shen et al., "A New Strategy of Iontophoresis for Hyperhidrosis," *J. Am. Acad. Dermatol.*, 22:239-241 (1990).
Stegehuis et al., "Treatment of Frey's Syndrome (Gustatory Sweating) with Topical Glycopyrrolate: Case Report," *New Zealand Medical Journal*, p. 479 (1989).
Stewart et al., "Stability of Ondansetron Hydrochloride and 12 Medications in Plastic Syringes," *Am. J. Health-Syst. Pharm.*, 55:2630-2634 (1998).
Teasdale et al., "Mechanism and Processing Parameters Affecting the Formation of Methyl Methanesulfonate from Methanol and Methanesulfonic Acid: An Illustrative Example for Sulfonate Ester Impurity Formation", *Organic Process Research & Development*, 2009, vol. 13, pp. 429-433.
The Merck Index, p. 646, (1983).
U.S. Appl. No. 60/325,105, Compositions and Methods for Inhibiting Eccrine Perspiration in Humans, filed Sep. 26, 2001.
Urman et al., "Diabetic Gustatory Sweating Successfully Treated with Topical Glycopyrrolate," *Arch. Intern. Med.*, 159:877-878 (1999).
Varssano et al., "The Mydriatic Effect of Topical Glycopyrrolate," Graefe's Arch. Clin. Exp. Ophthalmol., 234:205-207 (1996).
Demian et al., "High-Performance Liquid Chromatographic Separation of 3- [(Cyclopentylhydroxyphenylacetyl)oxy]-1,1-dimethyl-pyrrolidinium Bromide Diastereomers," Journal of Liquid Chromatography, 13(4):779-787 (1990).
European Medicines Agency "CHMP Assessment Report for Viracept", (Sep. 20, 2007); 31 pages.
European Medicines Agency, "Request to Assess the Risk of Occurrences of Contamination with Mesilate Esters and Related Compounds in Pharmaceuticals", (Jan. 24, 2008); 3 pages.
Flack, "On Enantiomorph-Polarity Estimation," Acta Cryst., A39(6):876-881 (1983).
Hooft et al., "Determination of absolute structure using Bayesian statistics on Bijvoet differences," Journal of Applied Crystallography, 41:96-103 (2008).
Jouyban et al., "Genotoxic Impurities in Pharmaceuticals," Toxicity and Drug Testing, Chapter 387 (Prof. Acree, ed.), InTech (2012); 29 pages.
NDA 17-558/S-053, Robinul Injection (Glycopyrrolate Injection, USP), pp. 3-12 (2005).
Nebiu et al., "Determination of (R,R)-glycopyrronium bromide and its related impurities by ion-pair HPLC," Pharmazie, 62:406-410 (2007).
Opposition Notice for Israeli Patent application No. 240684 dated May 26, 2016, 2 pages.
Motion to Revoke Acceptance of Israeli Patent application No. 240684 dated Jun. 13, 2016, 55 pages.
Otwinowski et al., "Processing of X-Ray Diffraction Data Collected in Oscillation Mode," Methods in Enzymology, 276:307-326 (1997).
Pahl et al., "Synergistic effects of the anti-cholinergic R,R-glycopyrrolate with anti-inflammatory drugs," Biochemical Pharmacology, 72:1690-1696 (2006).

ORTEP OF FORM D GLYCOPYRROLATE TOSYLATE MONOHYDRATE

FIG. 20 DSC AND TG OVERLAY OF A GLYCOPYRROLATE TOSYLATE X-RAY AMORPHOUS MATERIAL

GLYCOPYRROLATE SALTS

CROSS REFERENCE TO RELATED APPLICATIONS

This application is a continuation of U.S. patent application Ser. No. 15/438,636, filed Feb. 21, 2017 (now U.S. Pat. No. 10,004,717), which is a continuation of U.S. patent application Ser. No. 14/989,995 filed Jan. 7, 2016 (now U.S. Pat. No. 9,610,278), which is a continuation of U.S. patent application Ser. No. 14/643,553 filed Mar. 10, 2015 (now U.S. Pat. No. 9,259,414), which is a continuation application of U.S. patent application Ser. No. 14/473,537 filed Aug. 29, 2014 (now U.S. Pat. No. 9,006,462), which is a continuation of International Patent Application No. PCT/US2014/019552 filed Feb. 28, 2014, which claims priority to U.S. Provisional Patent Application No. 61/770,920 filed Feb. 28, 2013 and U.S. Provisional Patent Application No. 61/770,925 filed Feb. 28, 2013; International Patent Application No. PCT/US2014/019552 filed Feb. 28, 2014, claims priority to and is a continuation-in-part of U.S. patent application Ser. No. 14/024,480 filed Sep. 11, 2013 (now U.S. Pat. No. 9,006,461); and International Patent Application No. PCT/US2014/019552 filed Feb. 28, 2014, claims priority to and is a continuation-in-part of U.S. patent application Ser. No. 14/024,484 filed Sep. 11, 2013 (now U.S. Pat. No. 8,859,610). U.S. patent application Ser. Nos. 14/024,480 and 14/024,484 are each a continuation application of U.S. patent application Ser. No. 13/781,390, filed Feb. 28, 2013 (now U.S. Pat. No. 8,558,008). The entirety of each of these applications is hereby incorporated by reference.

BACKGROUND OF THE INVENTION

Glycopyrrolate is a quaternary ammonium cation of the muscarinic anticholinergic group. Glycopyrrolate, typically as a bromide salt, has been used in the treatment of a variety of conditions including diarrhea (U.S. Pat. Nos. 6,214,792 and 5,919,760), urinary incontinence (U.S. Pat. Nos. 6,204,285 and 6,063,808), and anxiety (U.S. Pat. No. 5,525,347). Additionally, U.S. Pat. No. 5,976,499 discloses a method for diagnosing cystic fibrosis in a patient by, in part, stimulating sweat production through the injection of a glycopyrrolate solution into a patient. Glycopyrrolate has also been used for the treatment of hyperhidrosis in US 20100276329.

Hyperhidrosis affects 8.8 million individuals in the United States alone, of whom 50.8% are estimated to have axillary hyperhidrosis and 25-34% have palmar or plantar hyperhidrosis. Hyperhidrosis is often treated with aluminum salts. Applying aluminum salts, such as aluminum chloride, causes frequent skin irritation and is of only limited effectiveness. Topically applied glycopyrrolate bromide has been shown to cause less skin irritation and have increased effectiveness over aluminum chloride.

Glycopyrrolate has well-known pharmacology (anticholinergic) and acts as a muscarinic receptor antagonist. As with other anticholinergic agents, glycopyrrolate inhibits the action of acetylcholine on structures innervated by postganglionic cholinergic nerves, such as sweat glands. Under physiologic conditions, salts of glycopyrrolate are dissociated; therefore, the pharmacological activity of glycopyrrolate is mediated by the active cation moiety, also referred to as glycopyrronium.

Glycopyrrolate has previously been made available as a bromide salt or an acetate salt. The bromide salt of glycopyrrolate is sold as Rubinol®. The term "glycopyrrolate" as used in the label for Rubinol® refers to the bromide salt which is more formally referred to as glycopyrronium bromide.

A drawback of using bromide salts of pharmaceutical compounds is the potential for inducing bromism which can result from too high an intake of bromide. Symptoms of bromism may include neurological abnormalities such as vision impairment and upper motor neuron disorders and dermatologic conditions such as papular and macular rashes. Symptoms more often develop due to chronic use rather than acute toxicity.

SUMMARY OF THE INVENTION

In one aspect of the invention, a salt of glycopyrrolate is provided wherein the anion is selected from benzoate, edisylate, oxalate, hydrogen sulfate, and tosylate.

In a further aspect of the invention, glycopyrrolate tosylate, including polymorphs, co-crystals, hydrates and solvates thereof, is provided.

In a further aspect of the invention, solid glycopyrrolate tosylate is provided, including polymorphs, solvates, hydrates and co-crystals thereof and amorphous glycopyrrolate tosylate.

In another aspect of the invention, glycopyrrolate tosylate monohydrate is provided.

In a further aspect of the invention, crystalline glycopyrrolate tosylate, including polymorphs, co-crystals, hydrates and solvates thereof, is provided.

In a yet another aspect of the invention, crystalline glycopyrrolate tosylate monohydrate and polymorphs thereof are provided.

In another aspect of the invention, Form C glycopyrrolate tosylate is provided.

In a further aspect of the invention, dehydrated crystalline glycopyrrolate tosylate monohydrate, hereinafter referred to as dehydrated Form D, is provided.

In further aspects of the invention, processes for making Forms C and D of glycopyrrolate tosylate are provided, as are Form C and Form D glycopyrrolate tosylate made by those processes.

In an additional aspect of the invention, processes for making threo glycopyrrolate tosylate are provided.

In another aspect of the invention, glycopyrrolate tosylate is provided.

In a further aspect of the invention threo glycopyrrolate tosylate is provided.

In another aspect of the invention, methods of treating hyperhidrosis using Forms C or D of glycopyrrolate tosylate are provided.

In another aspect of the invention, amorphous glycopyrrolate tosylate is provided.

In an additional aspect of the invention, solid dispersions comprising glycopyrrolate tosylate are provided.

In a further aspect of the invention, a topical comprising glycopyrrolate tosylate is provided.

In yet another aspect of the invention, processes for preparing an absorbent pad containing an aqueous solution of glycopyrrolate tosylate absorbed onto the pad is provided.

DETAILED DESCRIPTION OF THE INVENTION

Figure 1:
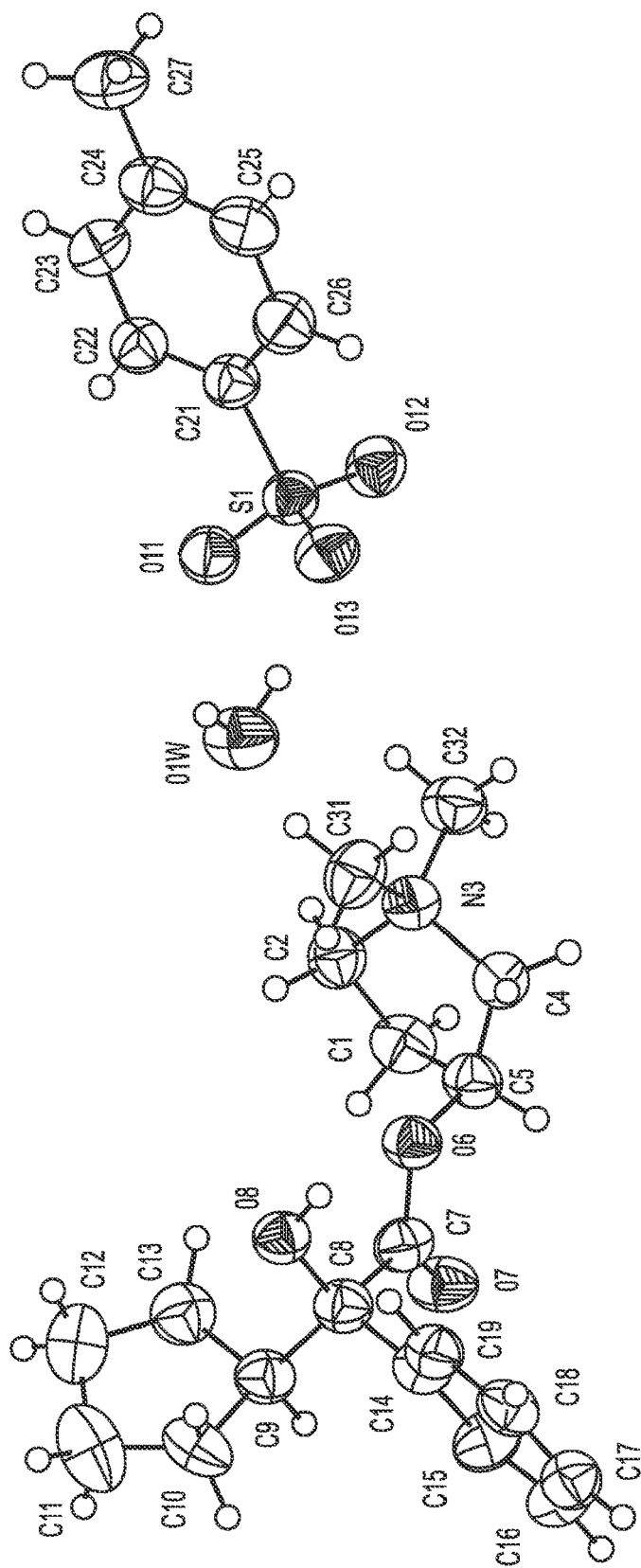
FIG. 1 is the ORTEP drawing of Form D glycopyrrolate tosylate monohydrate.

The term "solid form" is often used to refer to a class or type of solid-state material. One kind of solid form is a "polymorph" which refers to two or more compounds having the same chemical formula but differing in solid-state structure. Salts may be polymorphic. When polymorphs are elements, they are termed allotropes. Carbon possesses the well-known allotropes of graphite, diamond, and buckminsterfullerene. Polymorphs of molecular compounds, such as active pharmaceutical ingredients ("APIs"), are often prepared and studied in order to identify compounds meeting scientific or commercial needs including, but not limited to, improved solubility, dissolution rate, hygroscopicity, and stability.

Other solid forms include solvates and hydrates of compounds including salts. A solvate is a compound wherein a solvent molecule is present in the crystal structure together with another compound, such as an API. When the solvent is water, the solvent is termed a hydrate. Solvates and hydrates may be stoichiometric or non-stoichiometric. A monohydrate is the term used when there is one water molecule, stoichiometrically, with respect to, for example, an API, in the unit cell.

In order to identify the presence of a particular solid form, one of ordinary skill typically uses a suitable analytical technique to collect data on the form for analysis. For example, chemical identity of solid forms can often be determined with solution-state techniques such as $^{13}$C-NMR or $^{1}$H-NMR spectroscopy and such techniques may also be valuable in determining the stoichiometry and presence of "guests" such as water or solvent in a hydrate or solvate, respectively. These spectroscopic techniques may also be used to distinguish, for example, solid forms without water or solvent in the unit cell (often referred to as "anhydrates"), from hydrates or solvates.

Solution-state analytical techniques do not provide information about the solid state as a substance and thus, for example, solid-state techniques may be used to distinguish among solid forms such as anhydrates. Examples of solid-state techniques which may be used to analyze and characterize solid forms, including anhydrates and hydrates, include single crystal x-ray diffraction, x-ray powder diffraction ("XRPD"), solid-state $^{13}$C-NMR, Infrared ("IR") spectroscopy, Raman spectroscopy, and thermal techniques such as Differential Scanning calorimetry (DSC), melting point, and hot stage microscopy.

Polymorphs are a subset of crystalline forms that share the same chemical structure but differ in how the molecules are packed in a solid. When attempting to distinguish polymorphs based on analytical data, one looks for data which characterize the form. For example, when there are two polymorphs of a compound (e.g., Form I and Form II), one can use x-ray powder diffraction peaks to characterize the forms when one finds a peak in a Form I pattern at angles where no such peak is present in the Form II pattern. In such a case, that single peak for Form I distinguishes it from Form II and may further act to characterize Form I. When more forms are present, then the same analysis is also done for the other polymorphs. Thus, to characterize Form I against the other polymorphs, one would look for peaks in Form I at angles where such peaks are not present in the x-ray powder diffraction patterns of the other polymorphs. The collection of peaks, or indeed a single peak, which distinguishes Form I from the other known polymorphs is a collection of peaks which may be used to characterize Form I. If, for example, two peaks characterize a polymorph then those two peaks can be used to identify the presence of that polymorph and hence characterize the polymorph. Those of ordinary skill in the art will recognize that there are often multiple ways, including multiple ways using the same analytical technique, to characterize polymorphic polymorphs. For example, one may find that three x-ray powder diffraction peaks characterize a polymorph. Additional peaks could also be used, but are not necessary, to characterize the polymorph up to and including an entire diffraction pattern. Although all the peaks within an entire diffractogram may be used to characterize a crystalline form, one may instead, and typically does as disclosed herein, use a subset of that data to characterize such a crystalline form depending on the circumstances.

When analyzing data to distinguish an anhydrate from a hydrate, for example, one can rely on the fact that the two solid forms have different chemical structures—one having water in the unit cell and the other not. Thus, this feature alone may be used to distinguish the forms of the compound and it may not be necessary to identify peaks in the anhydrate, for example, which are not present in the hydrate or vice versa.

X-ray powder diffraction patterns are some of the most commonly used solid-state analytical techniques used to characterize solid forms. An x-ray powder diffraction pattern is an x-y graph with ° 2θ (diffraction angle) on the x-axis and intensity on the y-axis. The peaks within this plot may be used to characterize a crystalline solid form. The data is often represented by the position of the peaks on the x-axis rather than the intensity of peaks on the y-axis because peak intensity can be particularly sensitive to sample orientation (see Pharmaceutical Analysis, Lee & Web, pp. 255-257 (2003)). Thus, intensity is not typically used by those skilled in the art to characterize solid forms.

As with any data measurement, there is variability in x-ray powder diffraction data. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions may yield slightly different diffractograms. Factors such as particle size, moisture content, solvent content, and orientation may all affect how a sample diffracts x-rays. Another source of variability comes from instrument parameters. Different x-ray instruments operate using different parameters and these may lead to slightly different diffraction patterns from the same crystalline solid form. Likewise, different software packages process x-ray data differently and this also leads to variability. These and other sources of variability are known to those of ordinary skill in the pharmaceutical arts.

Due to such sources of variability, it is common to recite x-ray diffraction peaks using the word "about" prior to the peak value in ° 2θ which presents the data to within 0.1 or 0.2° 2θ of the stated peak value depending on the circumstances. The x-ray powder diffraction data corresponding to the solid forms of glycopyrrolate including glycopyrrolate tosylate of the disclosure were collected on instruments which were routinely calibrated and operated by skilled scientists. Accordingly, the variability associated with these data would be expected to be closer to ±0.1° 2θ than to ±0.2° 2θ and indeed likely less than 0.1 with the instruments used herein. However, to take into account that instruments used elsewhere by those of ordinary skill in the art may not be so maintained, for example, all x-ray powder diffraction peaks cited herein have been reported with a variability on the order of ±0.2° 2θ and are intended to be reported with such a variability whenever disclosed herein and are reported in the specification to one significant figure after the decimal even though analytical output may suggest higher precision on its face.

Single-crystal x-ray diffraction provides three-dimensional structural information about the positions of atoms and bonds in a crystal. It is not always possible or feasible, however, to obtain such a structure from a crystal, due to, for example, insufficient crystal size or difficulty in preparing crystals of sufficient quality for single-crystal x-ray diffraction.

X-ray powder diffraction data may also be used, in some circumstances, to determine the crystallographic unit cell of the crystalline structure. The method by which this is done is called "indexing." Indexing is the process of determining the size and shape of the crystallographic unit cell consistent with the peak positions in a suitable x-ray powder diffraction pattern. Indexing provides solutions for the three unit cell lengths (a, b, c), three unit cell angles (α, β, γ), and three Miller index labels (h, k, l) for each peak. The lengths are typically reported in Angstrom units and the angles in degree units. The Miller index labels are unitless integers. Successful indexing indicates that the sample is composed of one crystalline phase and is therefore not a mixture of crystalline phases.

IR spectroscopy is another technique that may be used to characterize solid forms together with or separately from x-ray powder diffraction. In an IR spectrum, absorbed light is plotted on the x-axis of a graph in the units of "wavenumber" (cm$^{-1}$), with intensity on the y-axis. Variation in the position of IR peaks also exists and may be due to sample conditions as well as data collection and processing. The typical variability in IR spectra reported herein is on the order of plus or minus 2.0 cm$^{-1}$. Thus, the use of the word "about" when referencing IR peaks is meant to include this variability and all IR peaks disclosed herein are intended to be reported with such variability.

Thermal methods are another typical technique to characterize solid forms. Different polymorphs of the same compound often melt at different temperatures. Thus, the melting point of a polymorph, as measured by methods such as capillary melting point, DSC, and hot stage microscopy, alone or in combination with techniques such as x-ray powder diffraction, IR spectroscopy, or both, may be used to characterize polymorphs or other solid forms.

As with any analytical technique, melting point determinations are also subject to variability. Common sources of variability, in addition to instrumental variability, are due to colligative properties such as the presence of other solid forms or other impurities within a sample whose melting point is being measured.

As used herein, the term "glycopyrrolate" refers to the glycopyrronium cation of the same salt. In other words, as used herein, glycopyrrolate and glycopyrronium are used interchangeably. For example, glycopyrrolate tosylate and glycopyrronium tosylate refer to the same salt.

The present invention provides the tosylate salt of glycopyrrolate or a solvate thereof, including the solution and various solid forms thereof, the process of preparing glycopyrrolate tosylate, and the therapeutic use of glycopyrrolate tosylate.

By "glycopyrrolate tosylate," it is meant a tosylate salt of glycopyrrolate or a tosylate salt of glycopyrronium having the chemical name of 3-[(cyclopentylhydroxyphenylacetyl) oxy]-1,1-dimethyl-pyrrolidinium tosylate, also known as "3-(2-cyclopentyl-2-hydroxy-2-phenylacetoxy)-1,1-dimethylpyrrolidinium 4-methylbenzenesulfonate," and a structure as shown below:

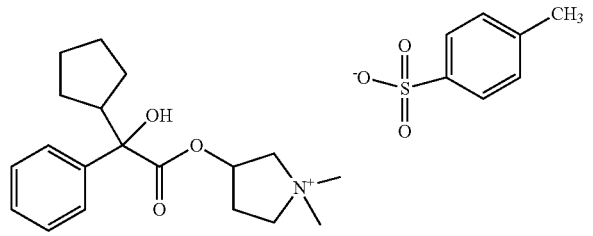

Furthermore, the term "glycopyrrolate tosylate," as used herein, unless otherwise specified explicitly or implicitly, such as a glycopyrrolate tosylate resulting from a glycopyrrolate starting material with specific diastereomers (e.g., glycopyrrolate bromide used herein which was a mixture of R,S and S,R diastereomers), includes any one of the four diastereomers listed below as well as any mixture of two, three, or four of the diastereomers:

(R)-3-((S)-2-cyclopentyl-2-hydroxy-2-phenylacetoxy)-1,1-dimethylpyrrolidinium 4-methylbenzenesulfonate;
(S)-3-((R)-2-cyclopentyl-2-hydroxy-2-phenylacetoxy)-1,1-dimethylpyrrolidinium 4-methylbenzenesulfonate;
(R)-3-((R)-2-cyclopentyl-2-hydroxy-2-phenylacetoxy)-1,1-dimethylpyrrolidinium 4-methylbenzenesulfonate; and
(S)-3-((S)-2-cyclopentyl-2-hydroxy-2-phenylacetoxy)-1,1-dimethylpyrrolidinium 4-methylbenzenesulfonate.

In one embodiment, "glycopyrrolate tosylate" is (R)-3-((S)-2-cyclopentyl-2-hydroxy-2-phenylacetoxy)-1,1-dimethylpyrrolidinium 4-methylbenzenesulfonate. In another embodiment, the "glycopyrrolate tosylate" is (S)-3-((R)-2-cyclopentyl-2-hydroxy-2-phenylacetoxy)-1,1-dimethylpyrrolidinium 4-methylbenzenesulfonate. In another embodiment, the "glycopyrrolate tosylate" is (R)-3-((R)-2-cyclopentyl-2-hydroxy-2-phenylacetoxy)-1,1-dimethylpyrrolidinium 4-methylbenzenesulfonate. In another embodiment, the "glycopyrrolate tosylate" is (S)-3-((S)-2-cyclopentyl-2-hydroxy-2-phenylacetoxy)-1,1-dimethylpyrrolidinium 4-methylbenzenesulfonate. In yet another embodiment, the "glycopyrrolate tosylate" is a racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate. In yet another embodiment, the "glycopyrrolate tosylate" is a racemic mixture of (R)-3-((R)-2-cyclopentyl-2-hydroxy-2-phenylacetoxy)-1,1-dimethylpyrrolidinium 4-methylbenzenesulfonate and (S)-3-((S)-2-cyclopentyl-2-hydroxy-2-phenylacetoxy)-1,1-dimethylpyrrolidinium 4-methylbenzenesulfonate. The solvate, such as hydrate, of "glycopyrrolate tosylate", can be a solvate, e.g., a hydrate, of any one of the four diastereomers listed above or any mixture of two, three, or four of the diastereomers. When referencing "threo" glycopyrrolate tosylate, those of ordinary skill will recognize that it refers to a mixture of R,S and S, R diastereomers. Thus, threo glycopyrrolate tosylate refers to a racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate.

It is to be understood that the invention further includes isotopic substitution. For example, deuterated glycopyrrolates are included within the definition of glycopyrrolate.

In one embodiment of the disclosure, a salt of glycopyrrolate is provided wherein the anion is selected from benzoate, edisylate, oxalate, hydrogen sulfate, and tosylate including hydrates and solvates thereof. In a further embodiment, a solid salt of glycopyrrolate is provided wherein the anion is selected from benzoate, edisylate, oxalate, hydrogen sulfate, and tosylate including polymorphs, hydrates, solvates, the corresponding amorphous forms of each salt, and co-crystals thereof.

Figure 12:
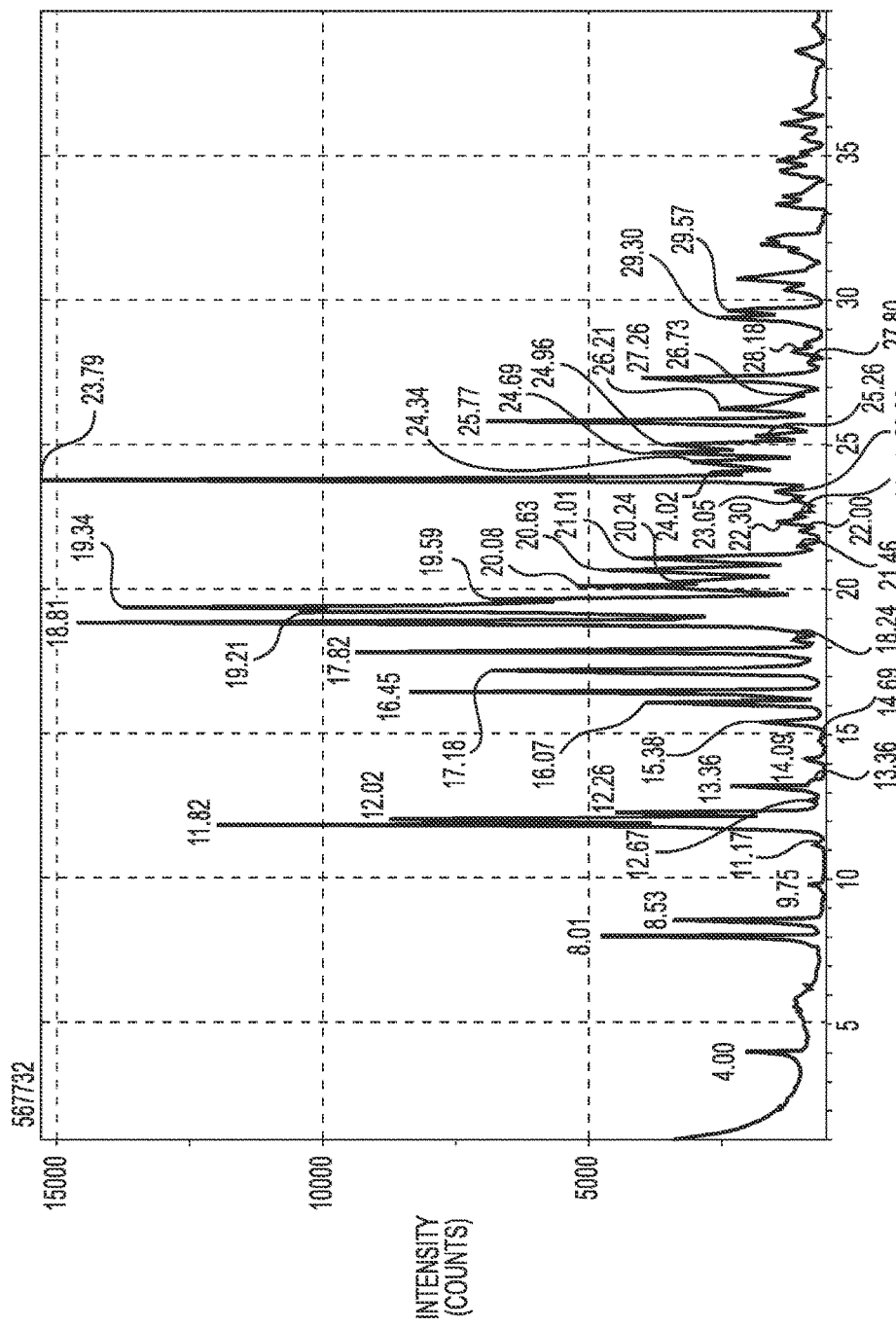
FIG. 12 is the x-ray powder diffraction for crystalline glycopyrrolate benzoate.
Figure 13:
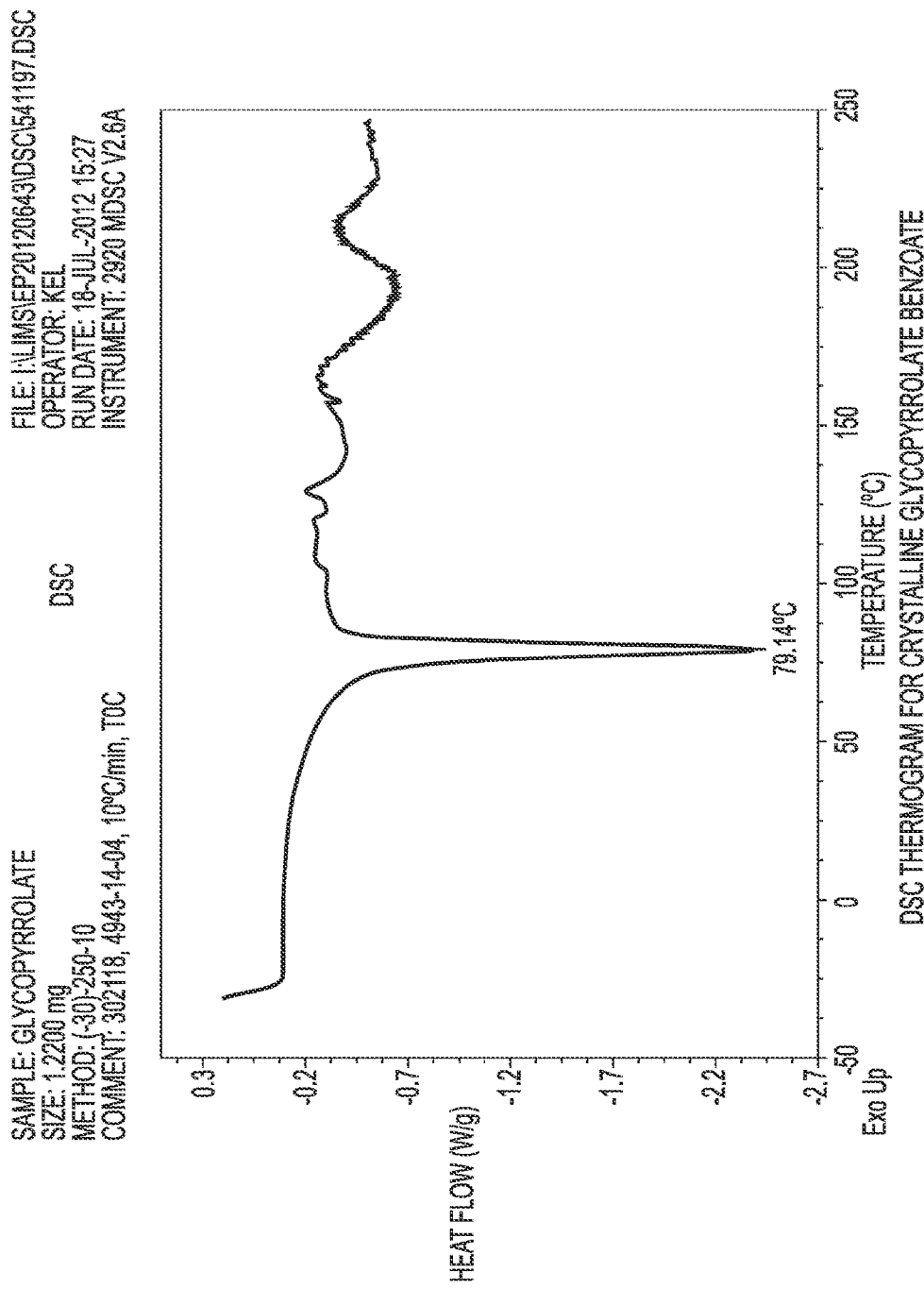
FIG. 13 is the DSC thermogram for crystalline glycopyrrolate benzoate.

In a further embodiment, a crystalline salt of glycopyrrolate benzoate is provided. An x-ray powder diffraction pattern substantially the same as the pattern of FIG. 12 may be used to characterize one embodiment of crystalline glycopyrrolate benzoate. A smaller subset of the peaks may be used to characterize crystalline glycopyrrolate benzoate. For example, any one or more of the peaks, for example, at about 8.0, 11.8, 16.1, 17.8, 18.8, 20.1, or 23.8°2θ may be used to characterize crystalline glycopyrrolate benzoate. For example, the peaks at about 8.0°2θ and 16.0°2θ may be used to characterize glycopyrrolate benzoate. In another embodiment, a DSC endotherm at about 79° C. as shown in FIG. 13 may be used to characterize crystalline glycopyrrolate benzoate. Combinations of x-ray data and DSC data may also be used to characterize glycopyrrolate benzoate. For example, one or more of the peaks at about 8.0, 11.8, 16.1, 17.8, 18.8, 20.1, or 23.8°2θ, such as the peaks at about 8.0°2θ and 18.8°2θ together with a DSC endotherm at about 79° C. may be used to characterize glycopyrrolate benzoate.

Figure 14:
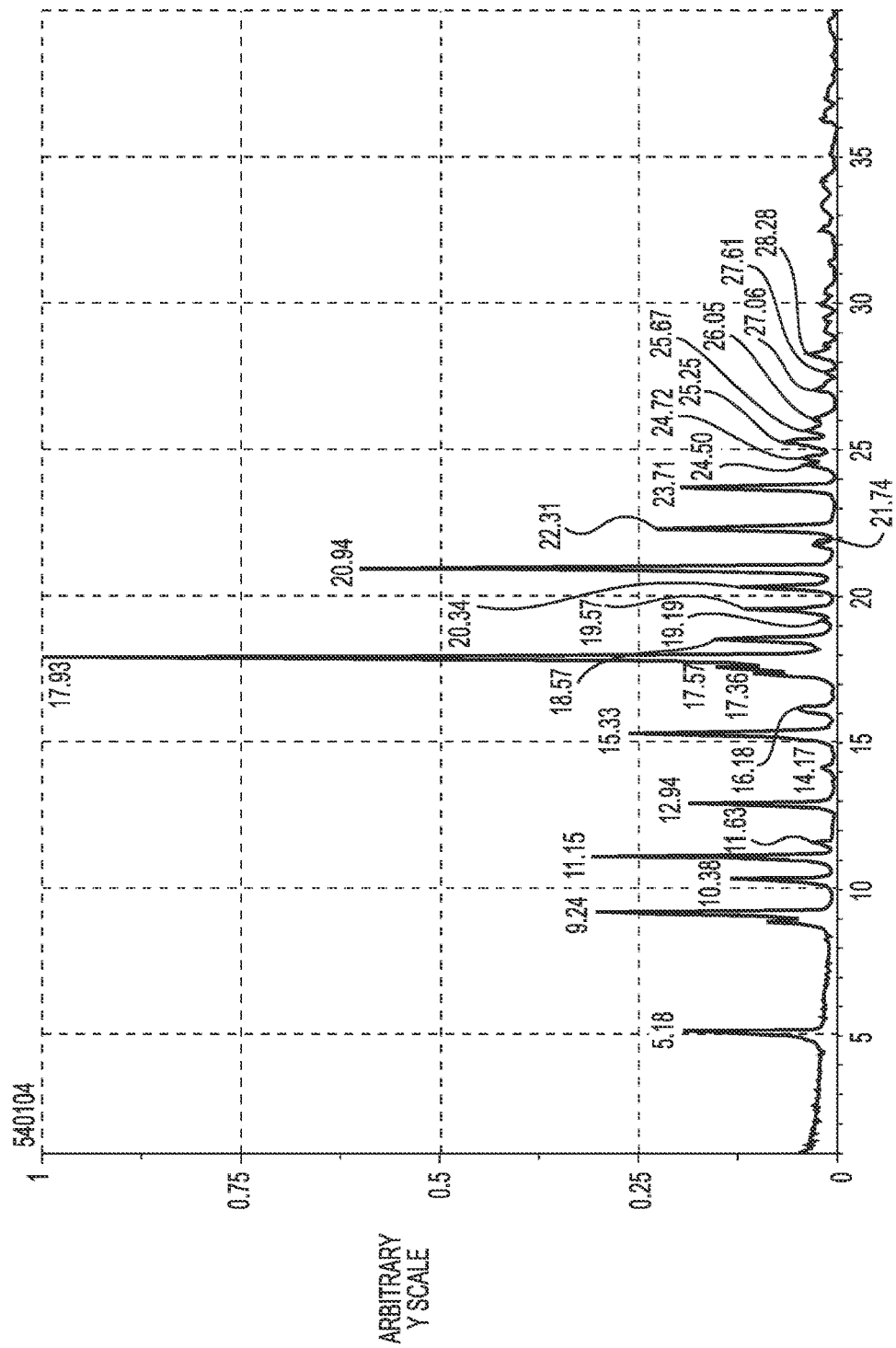
FIG. 14 is the x-ray powder diffraction for crystalline di-glycopyrrolate edisylate.
Figure 15:
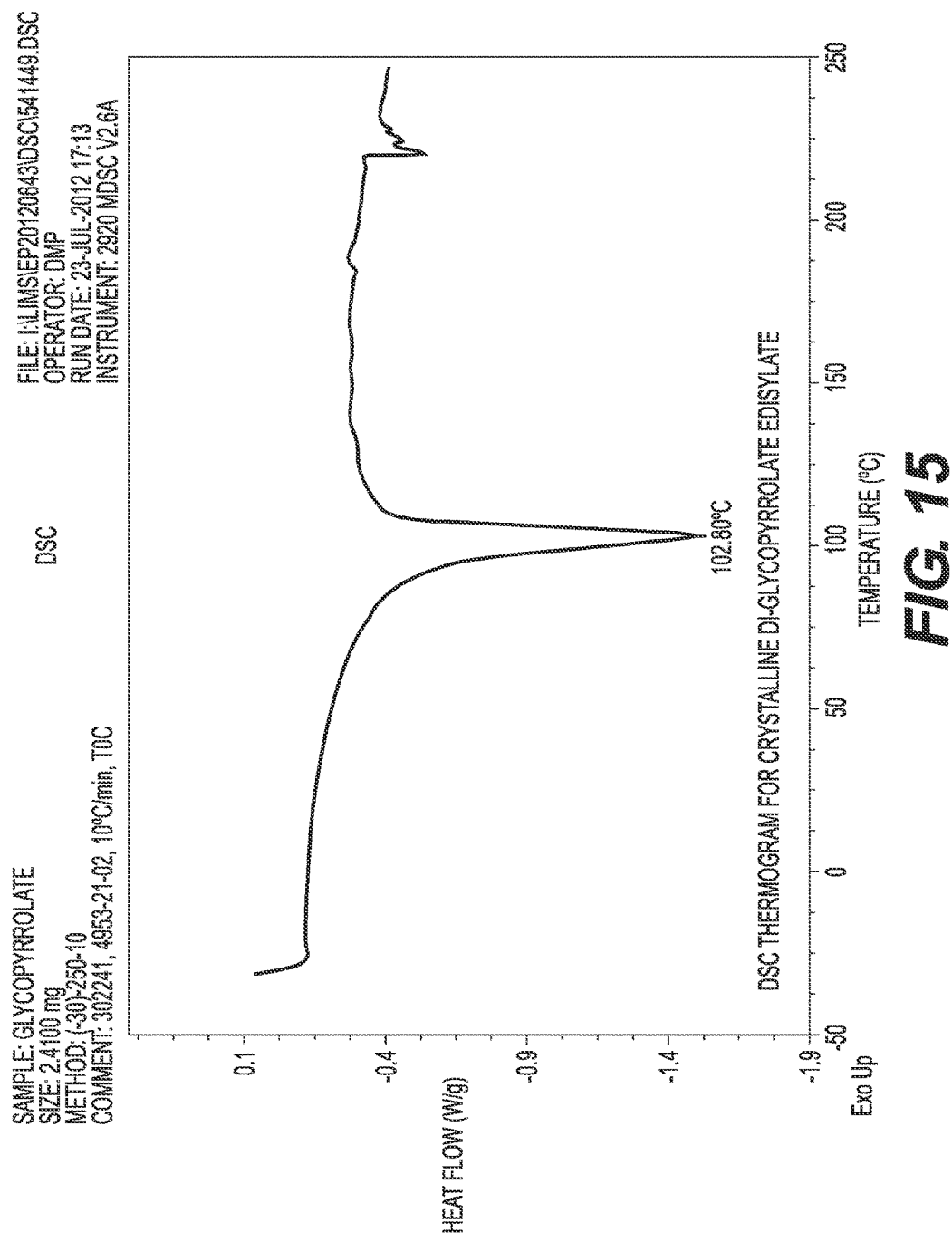
FIG. 15 is DSC thermogram for crystalline di-glycopyrrolate edisylate.

In an additional embodiment, a crystalline salt of di-glycopyrrolate edisylate is provided. An x-ray powder diffraction pattern substantially the same as the pattern of FIG. 14 may be used to characterize one embodiment of crystalline di-glycopyrrolate edisylate. A smaller subset of the peaks may be used to characterize crystalline di-glycopyrrolate edisylate. For example, any one or more of the peaks, for example, at about 5.2, 9.2, 10.4, 11.2, 12.9, 15.3, 17.9, 18.6, 20.9, 22.3, or 23.7°2θ may be used to characterize crystalline di-glycopyrrolate edisylate. For example, the peaks at about 11.2 and 17.9°2θ may be used to characterize di-glycopyrrolate edisylate. In another embodiment, a DSC endotherm at about 103° C. as shown in FIG. 15 may be used to characterize crystalline di-glycopyrrolate edisylate. Combinations of x-ray data and DSC data may also be used to characterize di-glycopyrrolate edisylate. For example, in addition, one or more of the peaks at about 5.2, 9.2, 10.4, 11.2, 12.9, 15.3, 17.9, 18.6, 20.9, 22.3, or 23.7°2θ, such as the peaks at about 11.2 and 17.9°2θ together with a DSC endotherm at about 103° C. may be used to characterize di-glycopyrrolate edisylate.

Figure 16:
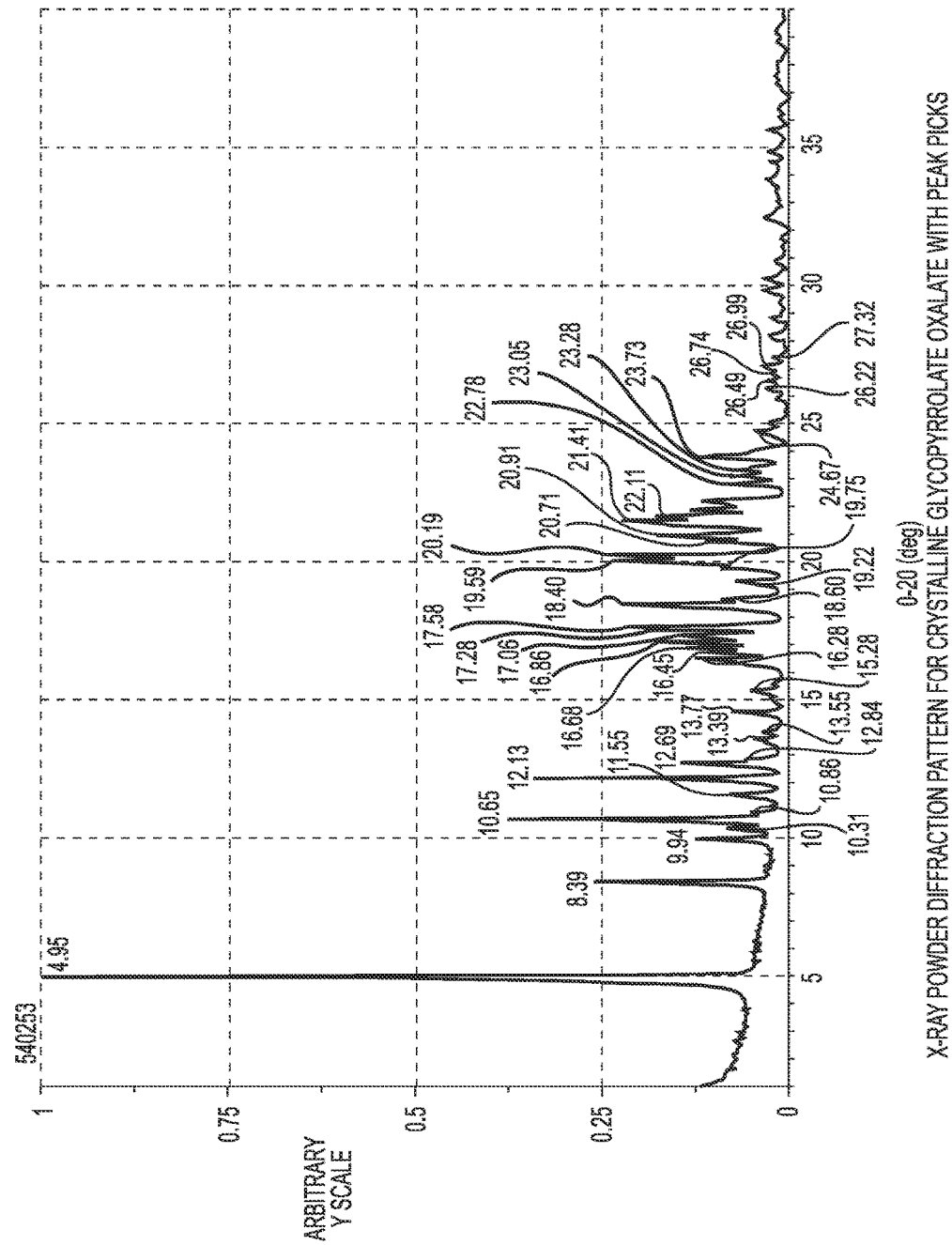
FIG. 16 is the x-ray powder diffraction for crystalline glycopyrrolate oxalate.

In a further embodiment, a crystalline salt of glycopyrrolate oxalate is provided. An x-ray powder diffraction pattern substantially the same as the pattern of FIG. 16 may be used to characterize one embodiment of crystalline glycopyrrolate oxalate. A smaller subset of the peaks may be used to characterize crystalline glycopyrrolate oxalate. For example, any one or more of the peaks, for example, at about 5.0, 8.4, 10.7, or 12.1°2θ may be used to characterize crystalline glycopyrrolate oxalate. For example, the peaks at about 5.0 and 8.4°2θ may be used to characterize glycopyrrolate oxalate.

Figure 17:
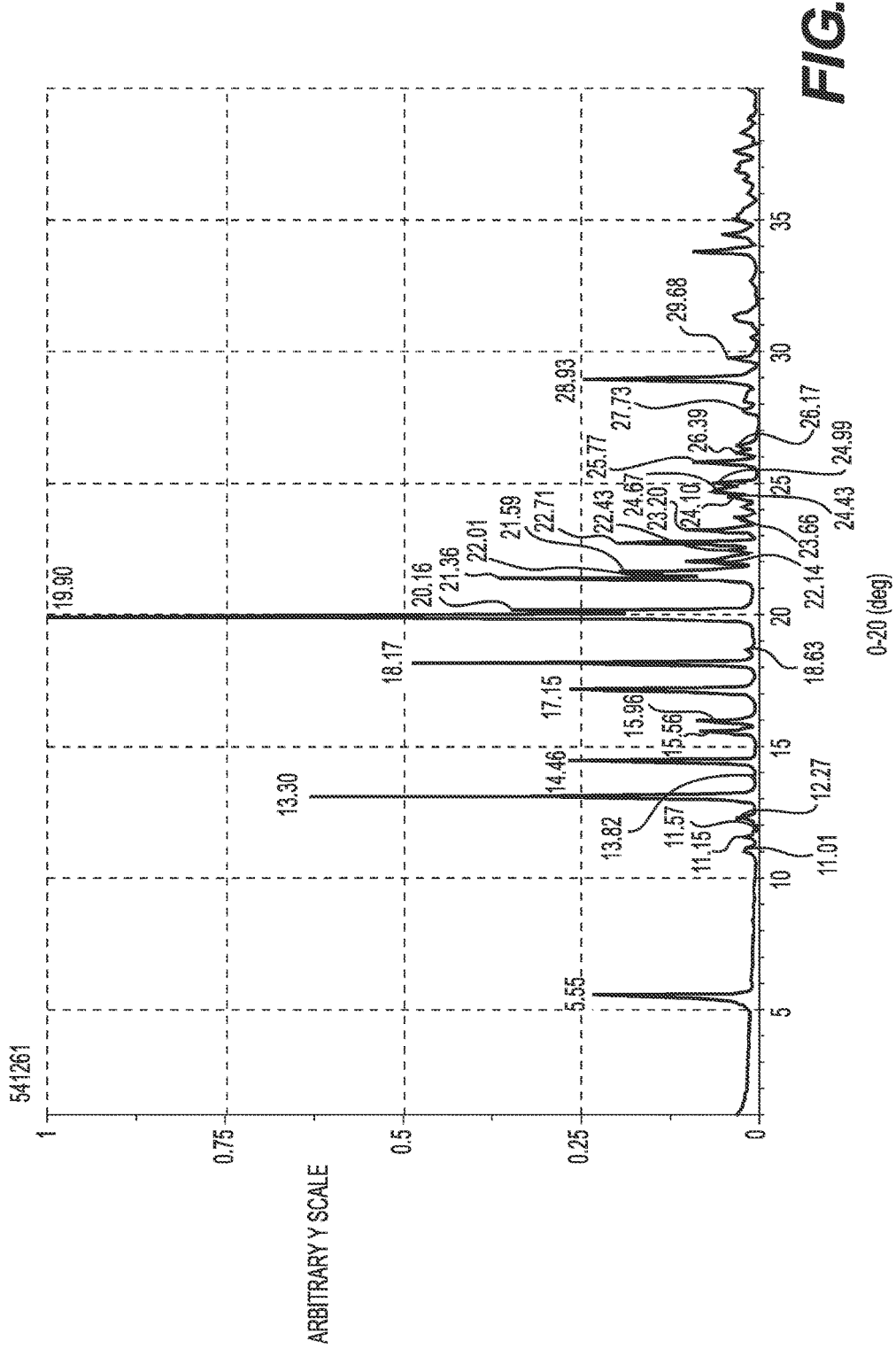
FIG. 17 is the x-ray powder diffraction for crystalline glycopyrrolate hydrogen sulfate.
Figure 18:
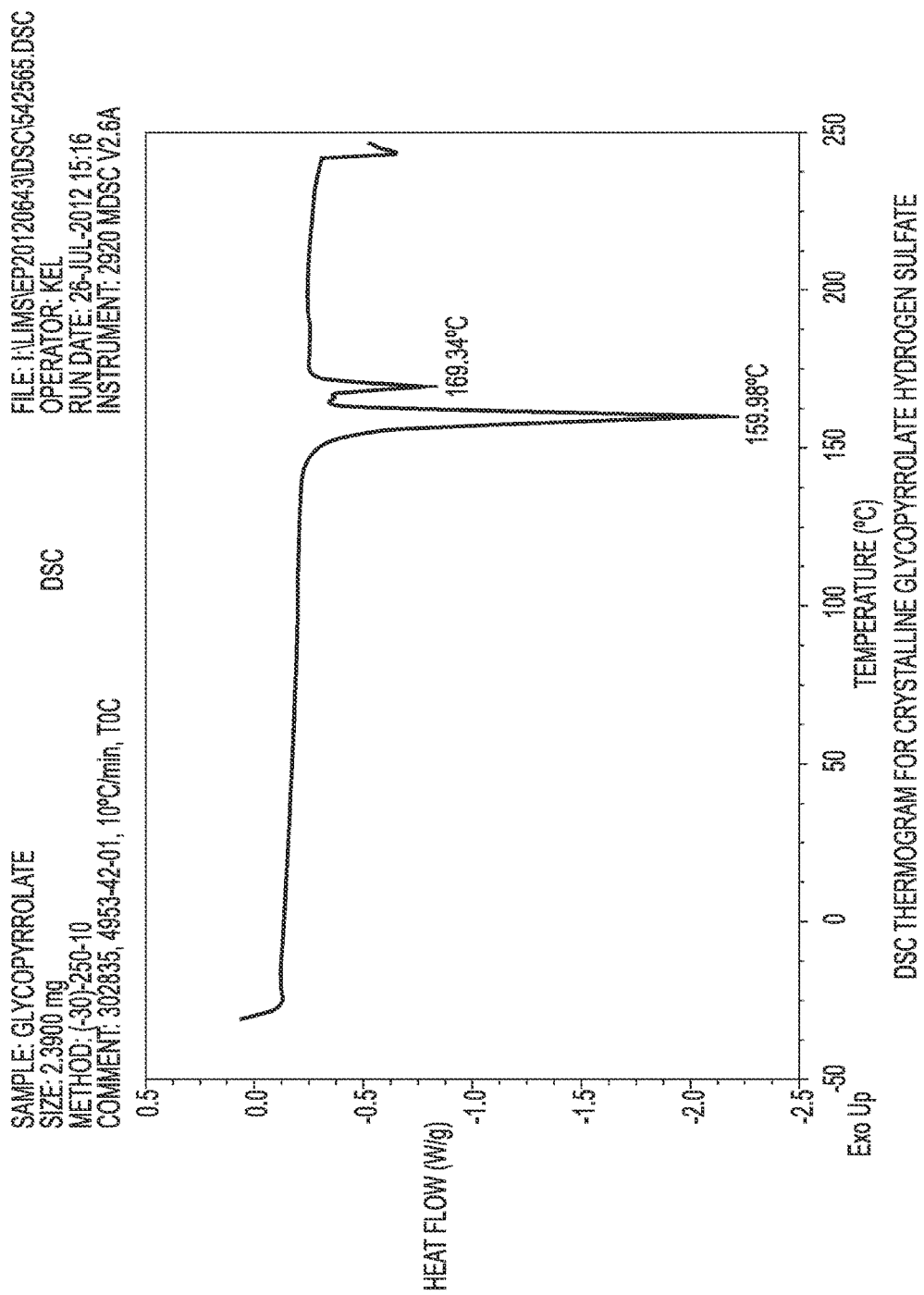
FIG. 18 is the DSC thermogram for crystalline glycopyrrolate hydrogen sulfate.

In an additional embodiment, a crystalline salt of glycopyrrolate hydrogen sulfate is provided. An x-ray powder diffraction pattern substantially the same as the pattern of FIG. 17 may be used to characterize one embodiment of crystalline glycopyrrolate hydrogen sulfate. A smaller subset of the peaks may be used to characterize crystalline glycopyrrolate hydrogen sulfate. For example, any one or more of the peaks, for example, at about 5.6, 13.1, 14.5, 17.2, 18.2, 19.9, 20.2, 21.4, 21.6, 22.7, or 28.9°2θ may be used to characterize crystalline glycopyrrolate hydrogen sulfate. For example, the peaks at about 5.6 and 13.1°2θ may be used to characterize crystalline glycopyrrolate sulfate. In another embodiment, a DSC endotherm at about 160° C. and/or a second endotherm at about 169° C. as shown in FIG. 18 may be used to characterize crystalline glycopyrrolate hydrogen sulfate. Combinations of x-ray data and DSC data may also be used to characterize glycopyrrolate hydrogen sulfate. For example, in addition, one or more of the peaks at about 5.6, 13.1, 14.5, 17.2, 18.2, 19.9, 20.2, 21.4, 21.6, 22.7, or 28.9, such as the peaks at about 5.6 and 13.1°2θ, together with a DSC endotherm at about 160° C. or a second endotherm at about 169° C. or both may be used to characterize glycopyrrolate hydrogen sulfate.

Figure 22:
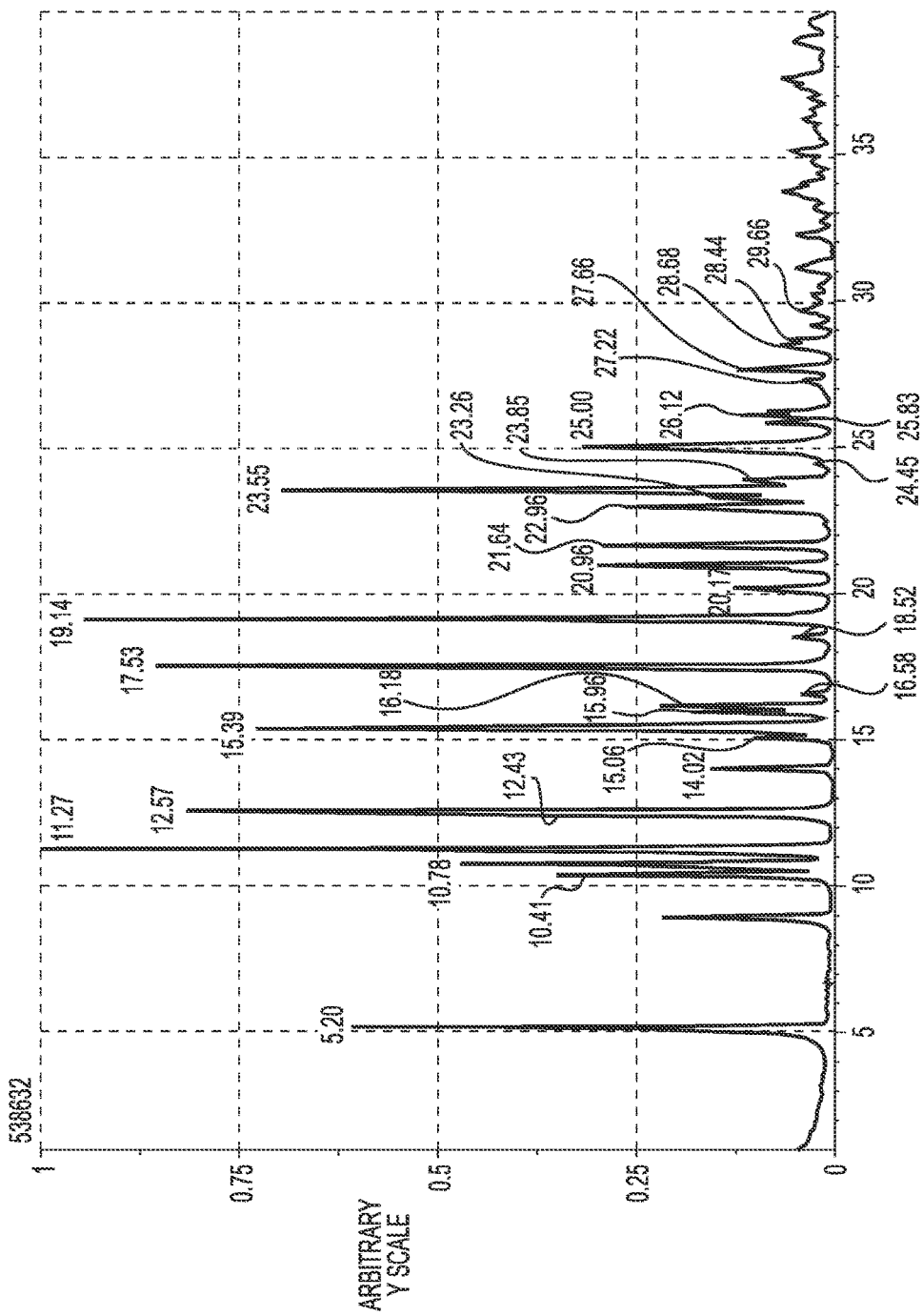
FIG. 22 is the x-ray powder diffraction pattern for glycopyrrolate acetate.

In a further embodiment, a crystalline salt of glycopyrrolate acetate is provided. An x-ray powder diffraction pattern substantially the same as the pattern of FIG. 22 may be used to characterize one embodiment of crystalline glycopyrrolate acetate. A smaller subset of the peaks may be used to characterize crystalline glycopyrrolate acetate. For example, any one or more of the peaks, for example, at about 5.2, 10.4, 10.8, 11.3, 12.6, 15.4, 17.5, 19.1, or 23.6°2θ may be used to characterize crystalline glycopyrrolate acetate. For example, the peaks at about 5.2 and 11.3°2θ may be used to characterize glycopyrrolate acetate.

In another embodiment crystalline glycopyrrolate tosylate monohydrate is provided, also referred to herein as Form D glycopyrrolate tosylate or Form D or crystalline glycopyrronium tosylate monohydrate. Exemplary preparations of Form D glycopyrrolate tosylate include Examples 8 and 9 herein. The ORTEP drawing of Form D glycopyrrolate tosylate, based on its crystal structure, is set forth in FIG. 1. The chemical structure of Form D glycopyrrolate tosylate is set forth below as Formula I:

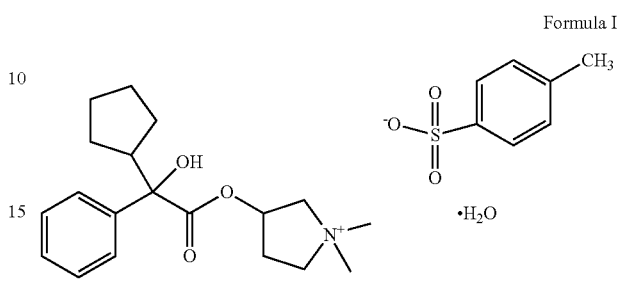

Formula I

The XRPD pattern corresponding to Form D glycopyrrolate tosylate is represented by FIG. 1. The crystal structure of the monoclinic Form D glycopyrrolate tosylate is set forth herein with the crystal data and acquisition parameter provided in Table 1.

TABLE 1

Crystal Data and Data Collection Parameters for Glycopyrrolate Tosylate Form D

| | |
|---|---|
| formula | $C_{26}H_{37}NO_7S$ |
| formula weight | 507.65 |
| space group P2$_1$/n (No. 14) | |
| a | 8.8715(5) Å |
| b | 11.5849(7) Å |
| c | 25.5323(14) Å |
| β | 96.9 deg |
| V | 2604.9(3) Å$^3$ |
| Z | 4 |
| d$_{calc}$, g cm$^{-3}$ | 1.294 |
| crystal dimensions, mm | 0.23 × 0.20 × 0.18 |
| temperature, K | 150. |
| radiation (wavelength, Å) | Cu K$_\alpha$ (1.54184) |
| monochromator | confocal optics |
| linear abs coef, mm$^{-1}$ | 1.479 |
| absorption correction applied | empirical$^a$ |
| transmission factors: min, max | 0.592, 0.766 |
| diffractometer | Rigaku RAPID-II |
| h, k, l range | 0 to 10 0 to 13 −31 to 30 |
| 2θ range, deg | 3.49-140.48 |
| mosaicity, deg | 0.76 |
| programs used | SHELXTL |
| F$_{000}$ | 1088.0 |
| weighting | |
| $1/[\sigma^2(F_o^2) + (0.1231P)^2 + 0.8250P]$ | |
| where $P = (F_o^2 + 2F_c^2)/3$ | |
| data collected | 24514 |
| unique data | 4024 |
| R$_{int}$ | 0.086 |
| data used in refinement | 4024 |
| cutoff used in R-factor calculations | $F_o^2 > 2.0\sigma(F_o^2)$ |
| data with I > 2.0σ(I) | 3812 |
| number of variables | 331 |
| largest shift/esd in final cycle | 0.00 |
| R(F$_o$) | 0.064 |
| R$_w$(F$_o^2$) | 0.185 |
| goodness of fit | 1.098 |

$^a$Otwinowski, Z.; Minor, W. Methods Enzymol. 1997, 276, 307.
$^b$Flack, H. D. Acta Cryst., 1983, A39, 876.
$^c$Hooft, R. W. W., Straver, L. H., and Spek, A. L. J. Appl. Cryst., 2008, 41, 96-103.

Form D glycopyrrolate tosylate was found to be monoclinic with space group P2$_1$/n. At 150K, the calculated density was found to be 1.294 grams per cubic centimeter. To two significant figures after the decimal, the unit cell dimensions were determined to be: a equals about 8.87 Å; b equals about 11.58 A; and c equals about 25.53 A, with corresponding unit cell angles of α=90.00°, β=96.9°, and γ=90.00°. The Form D unit cell was found to be racemic with both R,S and S,R diastereomers of glycopyrrolate in the unit cell.

Figure 2:
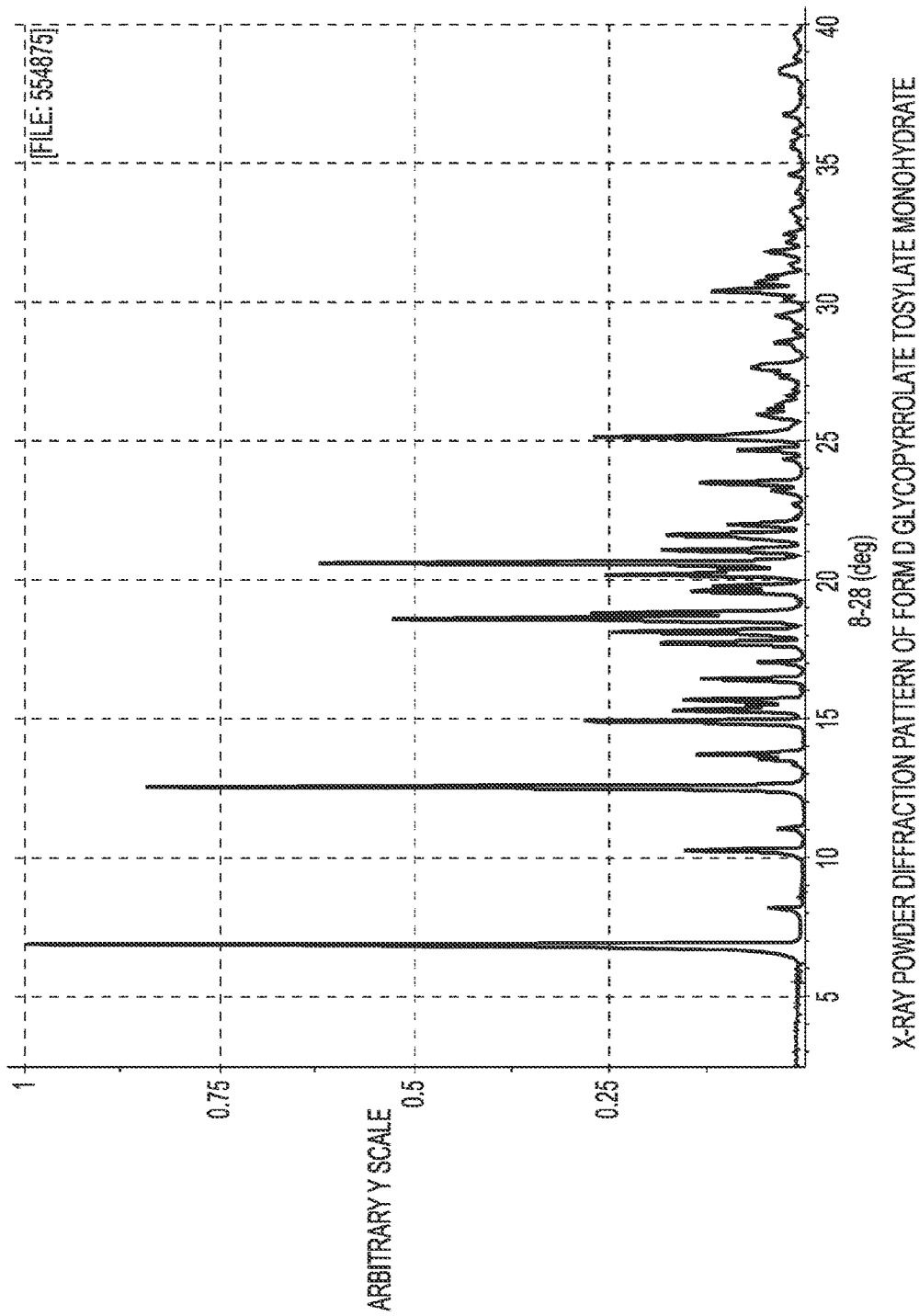
FIG. 2 is an x-ray powder diffraction pattern of Form D glycopyrrolate tosylate monohydrate.

A pattern substantially the same as the pattern of FIG. 2 may be used to characterize Form D glycopyrrolate tosylate. A smaller subset of the peaks identified in FIG. 2 may instead be used to characterize Form D glycopyrrolate tosylate. For example, any one or more of peaks at about 6.9, 10.3, 12.6, 13.7, 14.9, 15.3, 15.7, 16.4, 17.7, 18.2, or 20.6° 2θ may be used to characterize Form D glycopyrrolate tosylate. For example, the single peak at about 6.9 or 10.3 or 12.6, or 20.6° 2θ may be used to characterize Form D glycopyrrolate tosylate. In another example, peaks at about 6.9 and 10.3° 2θ may be used to characterize Form D glycopyrrolate. In a further example, the peaks at about 6.9, 10.3, and 12.6° 2θ may be used to characterize Form D glycopyrrolate tosylate. In still another example, the peaks at about 10.3 and 12.6° 2θ characterize Form D glycopyrrolate tosylate. Table 2 identifies selected peaks from FIG. 2. Intensity is provided for completeness.

TABLE 2

Selected Peaks from FIG. 2

| Diffraction angle °(2θ) | d spacing (Å) | Intensity (%) |
|---|---|---|
| 6.87 ± 0.20 | 12.867 ± 0.385 | 100 |
| 10.26 ± 0.20 | 8.620 ± 0.171 | 16 |
| 12.55 ± 0.20 | 7.052 ± 0.114 | 85 |
| 13.72 ± 0.20 | 6.454 ± 0.095 | 15 |
| 14.91 ± 0.20 | 5.943 ± 0.080 | 29 |
| 15.31 ± 0.20 | 5.788 ± 0.076 | 18 |
| 15.68 ± 0.20 | 5.653 ± 0.073 | 17 |
| 16.43 ± 0.20 | 5.396 ± 0.066 | 14 |
| 17.73 ± 0.20 | 5.002 ± 0.057 | 19 |
| 18.15 ± 0.20 | 4.888 ± 0.054 | 25 |
| 18.60 ± 0.20 | 4.770 ± 0.051 | 53 |
| 18.82 ± 0.20 | 4.716 ± 0.050 | 28 |
| 19.59 ± 0.20 | 4.532 ± 0.046 | 16 |
| 20.21 ± 0.20 | 4.395 ± 0.043 | 26 |
| 20.62 ± 0.20 | 4.307 ± 0.042 | 63 |
| 21.09 ± 0.20 | 4.212 ± 0.040 | 19 |
| 21.63 ± 0.20 | 4.109 ± 0.038 | 19 |
| 23.50 ± 0.20 | 3.786 ± 0.032 | 14 |
| 25.15 ± 0.20 | 3.541 ± 0.028 | 27 |

Further, Form D glycopyrrolate tosylate is distinguishable from Form C glycopyrrolate tosylate and the dehydrated form of Form D glycopyrrolate tosylate by the presence of water in the unit cell of Form D and may be so characterized.

Figure 3:
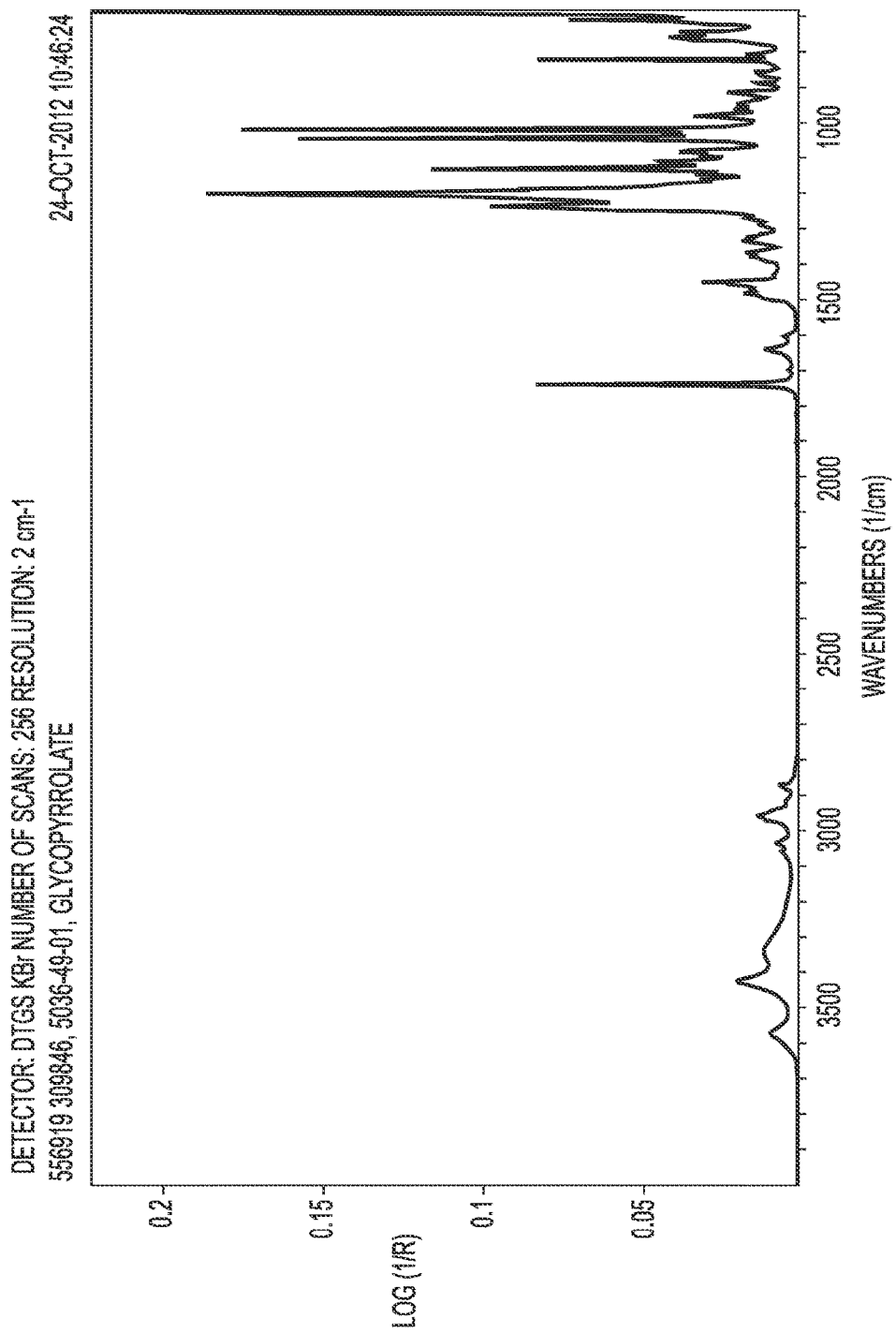
FIG. 3 is an infrared ("IR") spectrum of Form D glycopyrrolate tosylate monohydrate.

Form D glycopyrrolate tosylate may also be characterized by the IR spectrum in FIG. 3. When considering just IR spectroscopy, the entire IR spectrum may be used to characterize Form D glycopyrrolate tosylate or a subset of the spectrum may be so used. For example, any one or more of peaks at about 1734, 1196, 1125, 1036, 1013, and 682 cm$^{-1}$ or others may be used alone or in combination to characterize Form D glycopyrrolate tosylate. Selected peaks from the IR spectrum in FIG. 3 are set forth below in Table 3.

TABLE 3

Selected Peaks in the IR Spectrum of Form D in from FIG. 3 in cm$^{-1}$ 682
703

TABLE 3-continued

Selected Peaks in the IR Spectrum of Form D in from FIG. 3 in cm$^{-1}$ 713
735
750
801
815
850
856
880
908
934
940
954
975
1013
1024
1036
1075
1084
1125
1139
1155
1182
1196
1230
1265
1281
1312
1320
1329
1361
1373
1382
1445
1464
1476
1488
1495
1599
1636
1734
2868
2954
2967
3033
3057
3422
3568

Form D glycopyrrolate tosylate may be characterized by both the IR and XRPD data as set forth herein. For example, Form D glycopyrrolate tosylate may be characterized by one or more XRPD peaks selected from, for example, about 6.9, 10.3, 12.6, 13.7, 14.9, 15.3, 15.7, 16.4, 17.7, 18.2, or 20.6° 2θ and one or more of the IR peaks selected from, for example, about 1734, 1196, 1125, 1036, 1013, and 682 cm$^-$.

Form D may be prepared by several methods. In one method, glycopyrrolate bromide is treated with a metal salt such as silver salt, of tosylate to form a glycopyrrolate salt. In particular Form D glycopyrrolate tosylate may be prepared by treating Ag-tosylate with glycopyrrolate-X in a suitable solvent to form a slurry; removing the solids from the slurry to obtain a solution; lyophilizing the solution to form a solid; dissolving the solid in a crystallization solvent; and removing the crystallization solvent to form Form D glycopyrrolate tosylate, wherein X is a halide. Suitable solvents are those that will afford a slurry when treating Ag-tosylate with glycopyrrolate-X. An example of a suitable solvent is an alcohol such as isopropanol. A crystallization solvent is a solvent, or mixtures thereof, which will dissolve sufficient solid provided after the lyophilizing stage such that when the crystallization solvent is removed, Form D glycopyrrolate is the resulting solid. An example of a crystallization solvent is a mixture of acetonitrile and water. Embodiments include where X is a halide such as iodide or bromide.

In some embodiments, the crystallization solvent is removed by lowering the temperature of the solid obtained after lyophilizing in solution and decanting the solvent. In these and other embodiments, an anti-solvent, such as toluene, is added to the solution containing the dissolved solid.

Form D glycopyrrolate tosylate may also be prepared by treating glycopyrrolate-Y and p-toluenesulfonic acid in a suitable solvent; removal of the solvent to form a solid; re-dissolving the solid in a crystallization solvent to form a solution and removing the crystallization solvent to form Form D glycopyrrolate tosylate wherein Y is an organic anion. An example of Y is acetate.

In some embodiments, an anti-solvent, such as toluene, is added to the solution containing the dissolved solid.

As disclosed in US 20100276329, glycopyrrolate bromide may be used to treat hyperhidrosis such as by using a wipe containing a solution of glycopyrrolate bromide. It is the glycopyrrolate cation (glycopyrronium) of the bromide salt which is the active clinical moiety because glycopyrronium has equivalent binding affinity for the M3 muscarinic acetylcholine receptor in vitro when delivered as either the bromide or another salt such as the tosylate salt. In one study, patients suffering from hyperhidrosis were treated with formulations containing 2% and 4% glycopyrrolate based on a glycopyrrolate bromide preparation. It was observed that axillary sweating was reduced in patients during this study and a dose dependent trend in efficacy responses was also observed. Such dose dependency is consistent with glycopyrrolate's anti-muscarinic activity. Accordingly, glycopyrrolate tosylate may also be used to treat hyperhidrosis in patients such as by administering a topical containing glycopyrrolate tosylate. By topical, what is meant is a material or formulation comprising or containing glycopyrrolate tosylate which may be used to deliver glycopyrrolate tosylate, including a pharmaceutically effective amount of glycopyrrolate tosylate, to a patient. In many embodiments, the glycopyrrolate tosylate is threo glycopyrrolate tosylate. Examples of a topical include, but are not limited to, solutions, ointments, gels, lotions, powders, sprays, creams, cream bases, patches, pastes, washes, dressings, masks, gauzes, bandages, swabs, brushes, or pads. The application of the topical may be controlled by controlling the dose amount or the rate of release. The dose may be controlled by dissolving or dispensing threo glycopyrrolate tosylate, for example, in the appropriate medium. These and other dose controlling formulations may be used to deliver controlled doses such as specific unit doses, metered doses, or multiple doses from the topical.

In one embodiment, the topical is an absorbent pad. In such embodiments, such an absorbent pad may contain another topical such as a solution. As used herein, absorbent pads and nonwoven wipes are interchangeable and have the same meaning. In another embodiment, an absorbent pad containing threo glycopyrrolate tosylate in solution may be used to treat hyperhidrosis. Further, pads or wipes containing one or more of glycopyrrolate benzoate, edisylate, oxalate, or hydrogen sulfate in solution may similarly be used to treat hyperhidrosis in patients. In another embodiment, the pharmaceutically acceptable solution of threo glycopyrrolate tosylate is a topical.

In another embodiment, crystalline glycopyrrolate tosylate anhydrate is disclosed, also referred to herein as Form C glycopyrrolate tosylate or Form C. Exemplary preparations of Form C glycopyrrolate tosylate include Examples 11, 12, and 13 herein.

Figure 4:
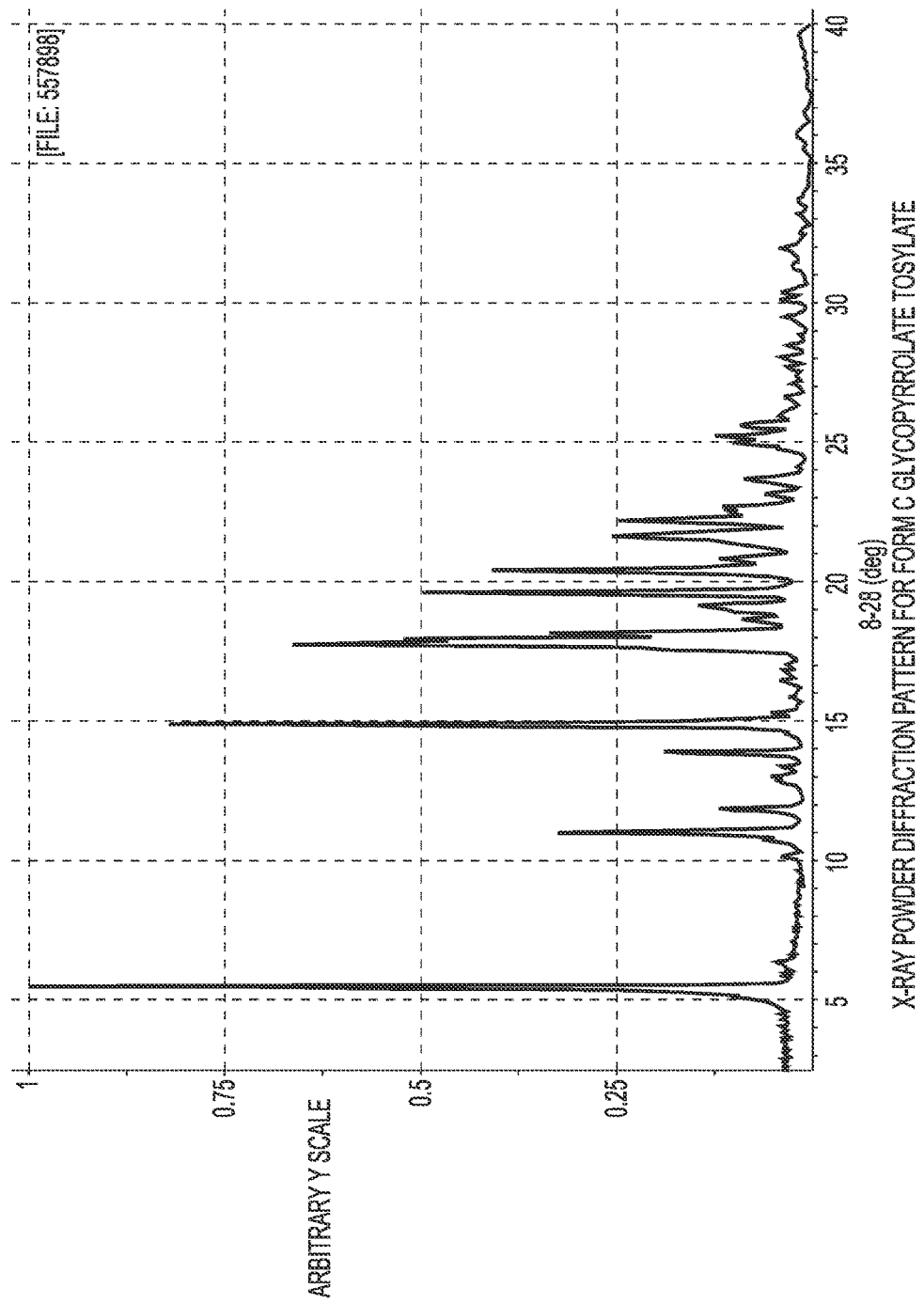
FIG. 4 is the x-ray powder diffraction pattern of Form C glycopyrrolate tosylate.

The x-ray powder diffraction pattern corresponding to Form C glycopyrrolate tosylate is provided in FIG. 4. The infrared spectrum corresponding to Form C glycopyrrolate tosylate is provided in FIG. 5. Form C was indexed to determine unit cell dimensions and the indexing solution is presented as FIG. 6.

An x-ray powder diffraction pattern substantially the same as the pattern of FIG. 4 may be used to characterize Form C glycopyrrolate tosylate. A smaller subset of the peaks identified in FIG. 4 may be used to characterize Form C glycopyrrolate tosylate. For example, any one or more of the peaks at about 5.5, 11.0, 11.8, 13.9, 14.9, 17.8, 19.6, 20.4, 21.6 and 22.1° 2θ may be used to characterize Form C glycopyrrolate tosylate. For example, the single peaks at about 5.5 or 11.0 or 14.9° 2θ may be used to characterize Form C glycopyrrolate tosylate, or any combination of the three. In another example, peaks at about 5.5 and 11.0° 2θ may be used to characterize Form C glycopyrrolate. In a further example, the peaks at about 5.5, 11.0, and 14.9° 2θ may be used to characterize Form C glycopyrrolate tosylate. Table 4 identifies selected peaks from FIG. 4. Further, Form C glycopyrrolate tosylate is distinguishable from Form D glycopyrrolate tosylate since Form C lacks water in the unit cell. Intensity is provided for completeness.

TABLE 4

Selected Peaks from FIG. 4

| Diffraction angle °(2θ) | d spacing (Å) | Intensity (%) |
| --- | --- | --- |
| 5.47 ± 0.20 | 16.168 ± 0.614 | 100 |
| 10.98 ± 0.20 | 8.057 ± 0.149 | 34 |
| 11.82 ± 0.20 | 7.489 ± 0.128 | 13 |
| 13.87 ± 0.20 | 6.384 ± 0.093 | 20 |
| 14.86 ± 0.20 | 5.963 ± 0.081 | 82 |
| 17.75 ± 0.20 | 4.997 ± 0.056 | 67 |
| 17.92 ± 0.20 | 4.951 ± 0.055 | 53 |
| 18.12 ± 0.20 | 4.897 ± 0.054 | 35 |
| 19.60 ± 0.20 | 4.528 ± 0.046 | 51 |
| 20.39 ± 0.20 | 4.356 ± 0.043 | 42 |
| 21.59 ± 0.20 | 4.116 ± 0.038 | 27 |
| 22.14 ± 0.20 | 4.014 ± 0.036 | 26 |

Figure 5:
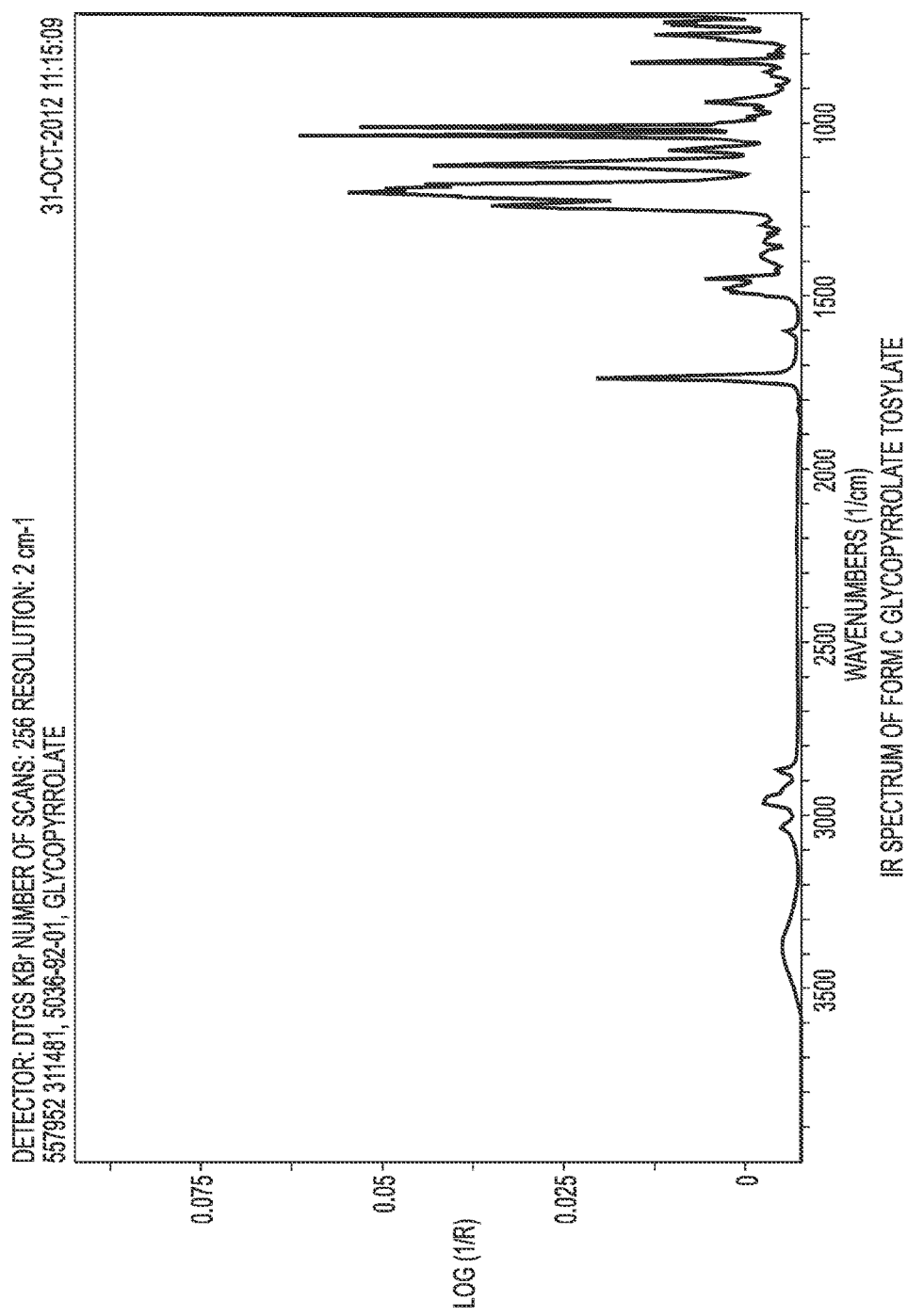
FIG. 5 is the IR spectrum of Form C glycopyrrolate tosylate.
Figure 6:
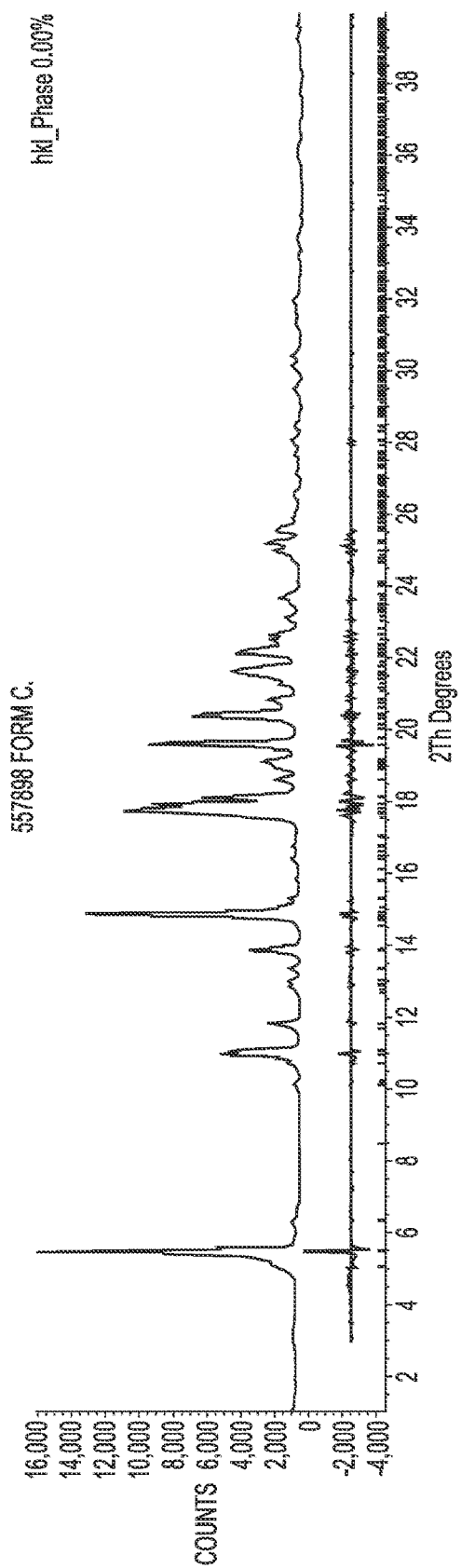
FIG. 6 is the indexing solution for Form C glycopyrrolate tosylate with Pawley refinement.

Form C glycopyrrolate tosylate may also be characterized by the IR spectrum in FIG. 5. When considering just IR spectroscopy, the entire IR spectrum may be used to characterize Form C glycopyrrolate tosylate or a subset of the spectrum may be so used. For example, any one or more of the peaks at about 1733, 1236, 1211, 1198, 1186, 1177, 1120, 1032, 1008, and 682 $cm^{-1}$ or others may be used alone or in combination to characterize Form C glycopyrrolate tosylate. Selected peaks from the IR spectrum in FIG. 5 are set forth below in Table 5.

TABLE 5

Selected Peaks from FIG. 5 in $cm^{-1}$

| |
| --- |
| 682 |
| 706 |
| 714 |
| 742 |
| 755 |
| 786 |
| 801 |
| 821 |
| 849 |

TABLE 5-continued

Selected Peaks from FIG. 5 in cm$^{-1}$ 886
929
938
956
980
1008
1032
1075
1120
1177
1186
1198
1211
1236
1293
1317
1446
1464
1475
1485
1597
1733
2867
2961
3032

Form C glycopyrrolate tosylate may be characterized by both the IR and XRPD data as set forth herein. For example, Form C glycopyrrolate tosylate may be characterized by one or more XRPD peaks selected from, for example, about 5.5, 11.0, 11.8, 13.9, 14.9, 17.8, 19.6, 20.4, 21.6, and 22.1° 2θ and one or more of the IR peaks selected from, for example, 1733, 1236, 1211, 1198, 1186, 1177, 1120, 1032, 1008, and 682 cm$^{-1}$.

Form C may also be characterized by its thermal characteristics. For example, Form C exhibits a melting endotherm at about 168° C. when measured with a Tzero™ pan type configuration at a heating rate of 10° C. per minute from −30° C. to 250° C.

Figure 7:
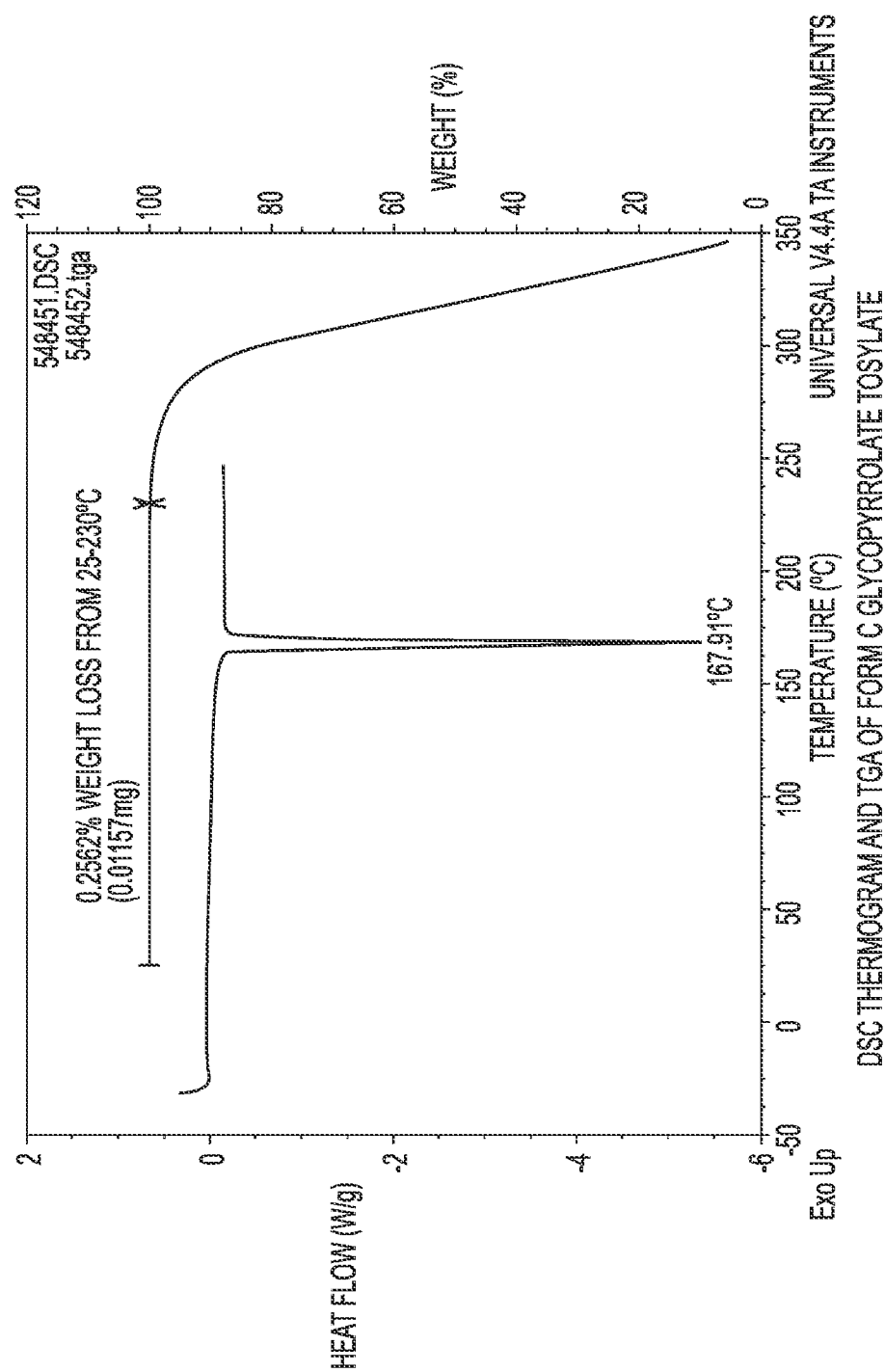
FIG. 7 includes a DSC thermogram and TGA for Form C glycopyrrolate tosylate.

Form C may be characterized by its DSC thermogram alone or in combination with the x-ray powder diffraction data, IR data, or both. For example, Form C glycopyrrolate tosylate may be characterized by a DSC thermogram having an endotherm at about 168° C. and the x-ray powder diffraction pattern of FIG. 4 and the IR spectrum of FIG. 5. However, it is not necessary to use all of these data to characterize Form C when using DSC. For example, the single peak at about 5.5° 2θ and the DSC endotherm at about 168° C. may be used to characterize Form C glycopyrrolate tosylate (see FIG. 7). In another example, the peak at about 168° C. and the IR peak at about 1733 cm$^{-1}$ may be used to characterize Form C glycopyrrolate tosylate. In yet another example, the endotherm at 168° C., the x-ray powder diffraction peak at about 5.5° 2θ, and the IR peak at about 1733 cm$^{-1}$ may be used to characterize Form C glycopyrrolate tosylate.

Form C may be prepared by dehydrating Form D. Alternatively, Form C may be prepared by dissolving a glycopyrrolate salt such as, for example, at elevated temperatures such as about 50° C. Slow cooling of the solution to room temperature followed by vacuum filtration and washing in a suitable organic solvent such as acetone results in the formation of Form C.

Figure 8:
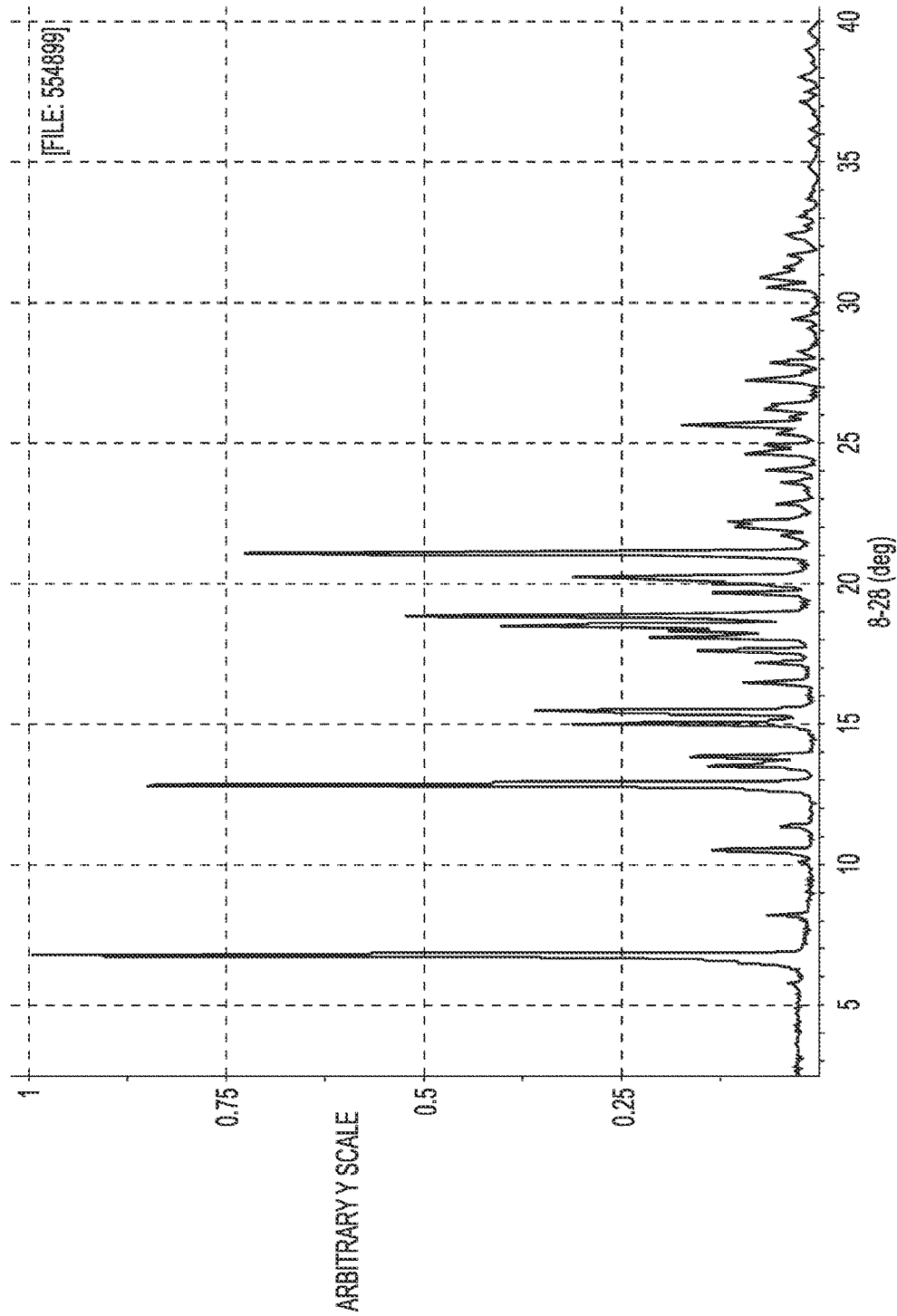
FIG. 8 is the x-ray powder diffraction for dehydrated Form D glycopyrrolate tosylate.
Figure 9:
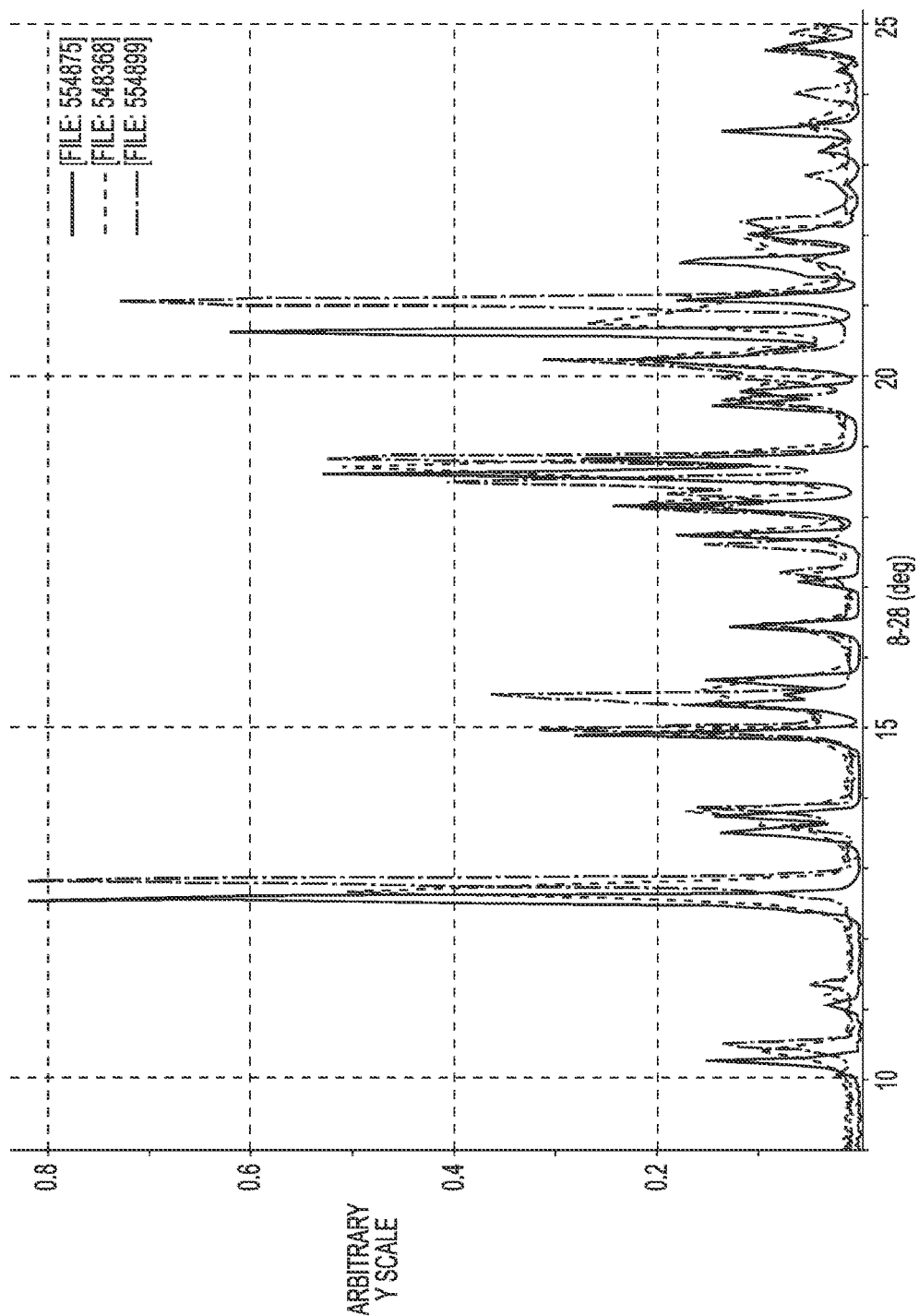
FIG. 9 is an overlay of Form D and dehydrated Form D glycopyrrolate tosylate.

In a further embodiment, dehydrated forms of Form D are provided. An exemplary preparation of dehydrated Form D includes Example 10 herein. In one such embodiment, a dehydrated form of Form D, hereinafter referred to as dehydrated Form D, is provided wherein there is no water in the unit cell. An x-ray powder diffraction pattern of dehydrated Form D is provided in FIG. 8. An overlay of the diffraction pattern showing dehydrated Form D and Form D is provided in FIG. 9.

Figure 10:
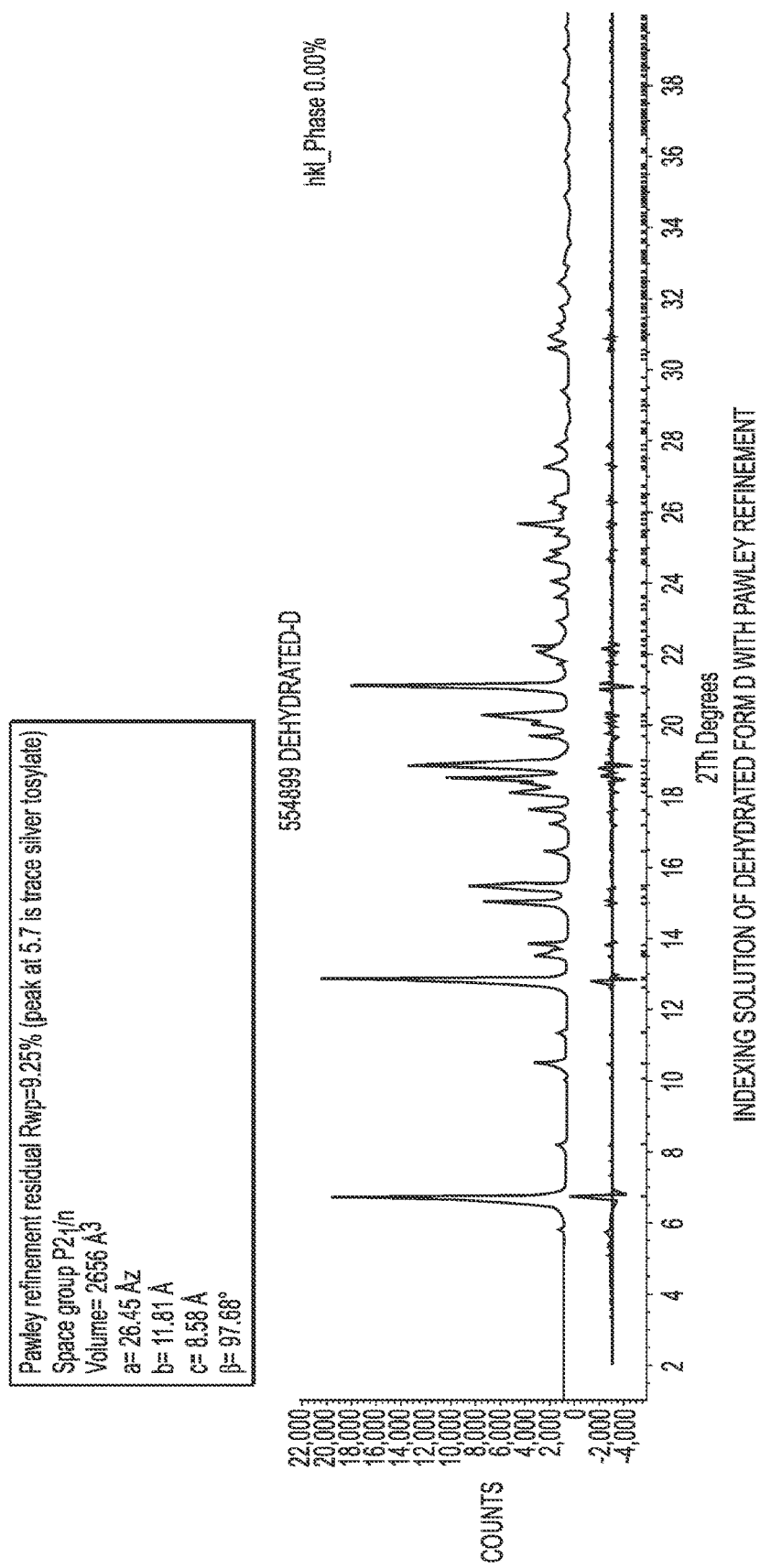
FIG. 10 is the indexing solution for dehydrated Form D glycopyrrolate tosylate with Pawley refinement.
Figure 11:
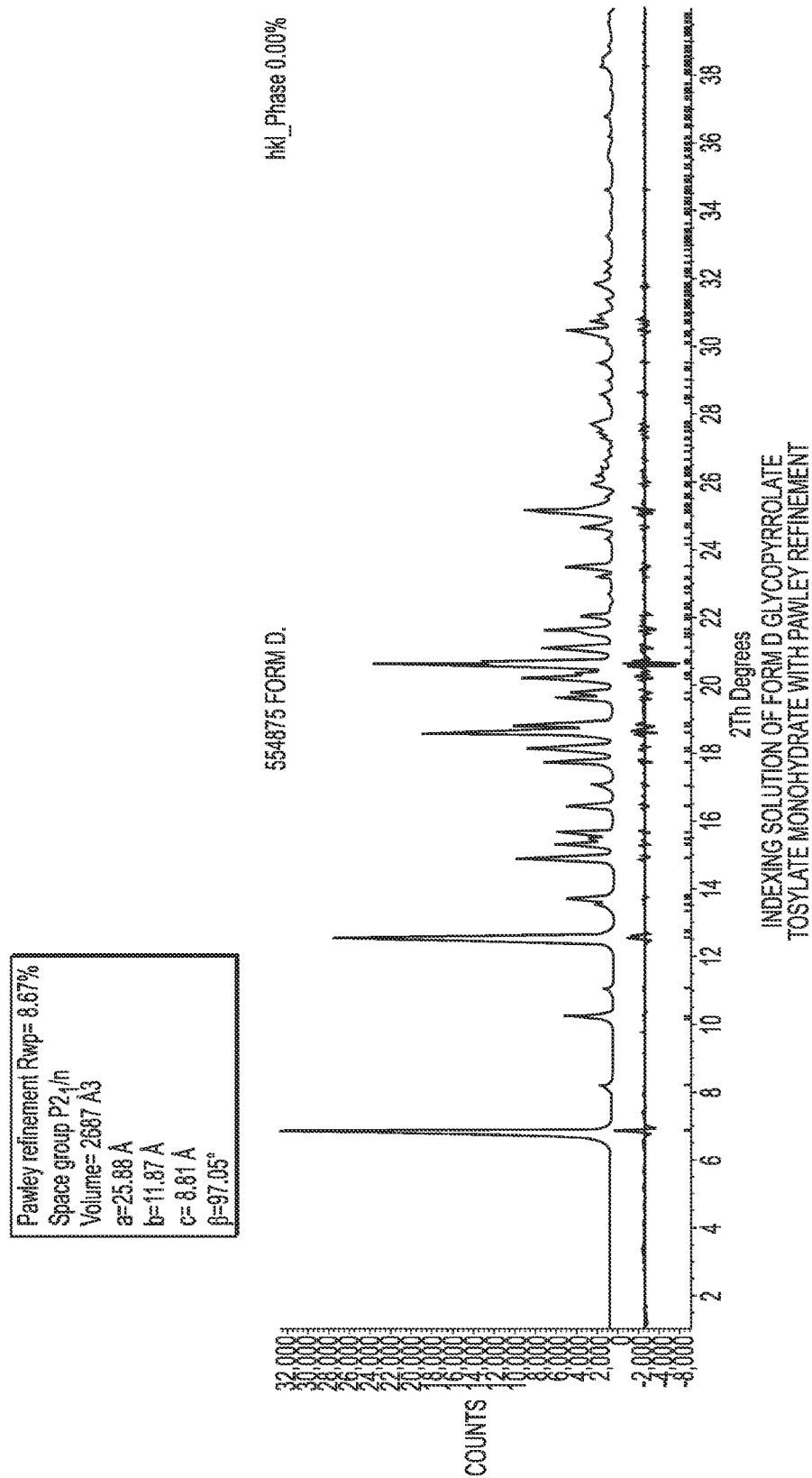
FIG. 11 is the indexing solution for Form D glycopyrrolate tosylate monohydrate with Pawley refinement.

The indexing solution, with a Pawley refinement, to dehydrated Form D is presented in FIG. 10 and indicates a unit cell which is of the same proportions, within experimental variation, as with the indexing solution of Form D, also with a Pawley refinement (FIG. 11) except for a loss of volume, which is consistent with water loss, and which results in a smaller unit cell. The indexing solution from FIG. 11 presents a, b, and c parameters which correspond, respectively, to the c, b, and a parameters of the single crystal study (performed at 150 K) as set forth in Table 1.

The overlay pattern from Form D and dehydrated Form D show that there are some shifts between the two forms and that can also be seen in the comparison of the peak positions for selected Miller indices as set forth in Table 6 below. The differences in the Miller indices between Form D and dehydrated Form D confirm that they are different solid forms.

TABLE 6

Select Miller Indices and Peak Comparisons between Form D and Dehydrated Form D

| h | k | l | Form D (2Θ) | Dehydrated (2Θ) | Δ |
|---|---|---|---|---|---|
| 2 | 0 | 0 | 6.84873 | 6.74897 | −0.09976 |
| 1 | 1 | 0 | 8.16348 | 8.21407 | 0.05059 |
| 2 | 1 | 0 | 10.09605 | 10.08663 | −0.00942 |
| 1 | 0 | −1 | 10.22338 | 10.50517 | 0.28179 |
| 1 | 0 | 1 | 11.02323 | 11.37050 | 0.34727 |
| 0 | 1 | 1 | 12.50656 | 12.83560 | 0.32904 |
| 1 | −1 | −1 | 12.63742 | 12.91262 | 0.2752 |
| 2 | 0 | 2 | 22.15015 | 22.85492 | 0.70477 |
| 1 | 1 | 2 | 22.21449 | 22.92323 | 0.70874 |

Dehydrated Form D is further distinguishable from Form D since it lacks water of crystallization whereas Form D is a monohydrate and from Form C because the peaks of dehydrated Form D (an anhydrate) differ substantially from those in Form C (anhydrate). For example, as Table 6 indicates, dehydrated Form D has a peak at about 6.75° 2θ whereas the closest peak from Form C is at about 6.30° 2θ, a difference of 0.45° 2θ. In addition, the indexing solution for Form C shows the unit cell to be triclinic whereas the unit cell of dehydrated Form D is monoclinic.

In another series of embodiments, variable hydrates, each with different water content in between dehydrated Form D and monohydrate Form D is provided. Such embodiments provide for a continuum of water content in between dehydrated Form D and Form D as illustrated with one example in FIG. 9. One would expect that other materials with an intermediate water content to generally exhibit x-ray powder diffraction pattern yielding peaks which are intermediate between Form D and dehydrated Form D.

Figure 19:
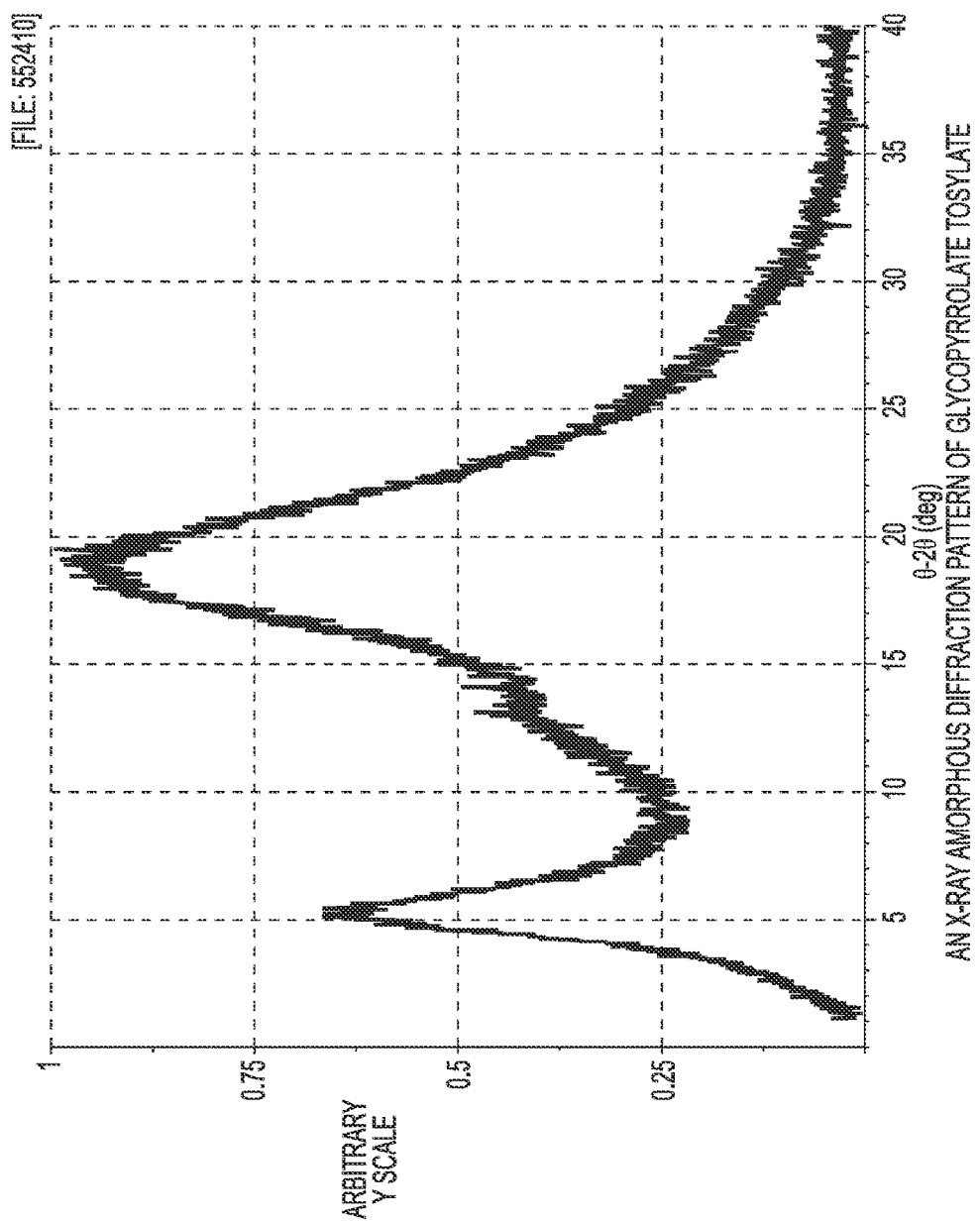
FIG. 19 is an x-ray amorphous diffraction pattern of glycopyrrolate tosylate.

In a further embodiment, the amorphous glycopyrrolate tosylate has an x-ray powder diffraction pattern exhibiting a figure substantially the same as FIG. 19. In another embodiment, the amorphous glycopyrrolate tosylate of the invention has a glass transition temperature onset of about 11.6° C. In yet another embodiment, the amorphous glycopyrrolate tosylate of the invention has an x-ray powder diffraction pattern substantially the same as in FIG. 19 and a glass transition onset temperature of about 11.6° C. In still an additional embodiment, the amorphous glycopyrrolate tosylate of the invention has an x-ray powder diffraction pattern exhibiting an amorphous halo but that is not substantially similar to that of FIG. 19.

Figure 20:
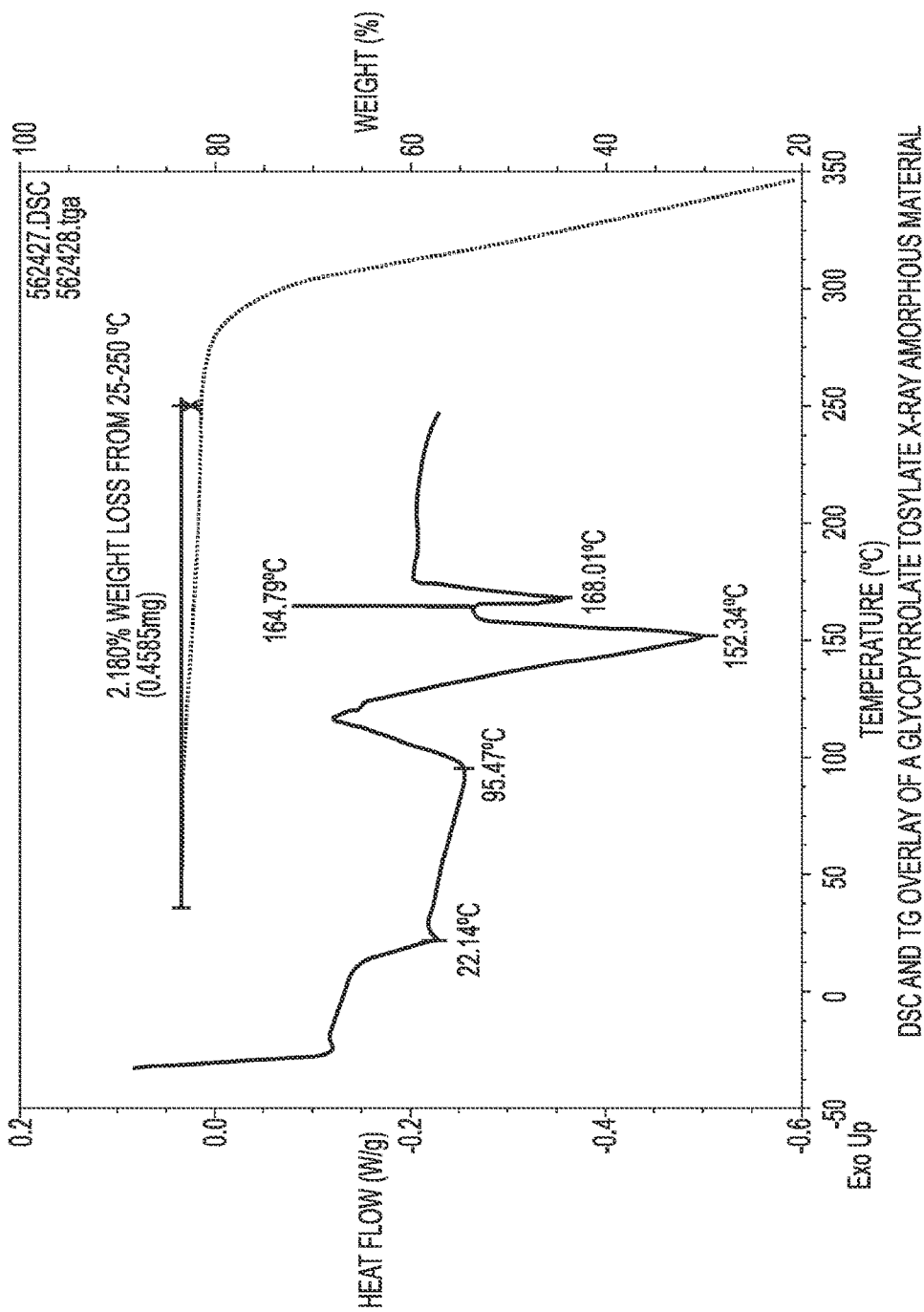
FIG. 20 is a DSC/TGA overlay of an x-ray amorphous glycopyrrolate tosylate.
Figure 21:
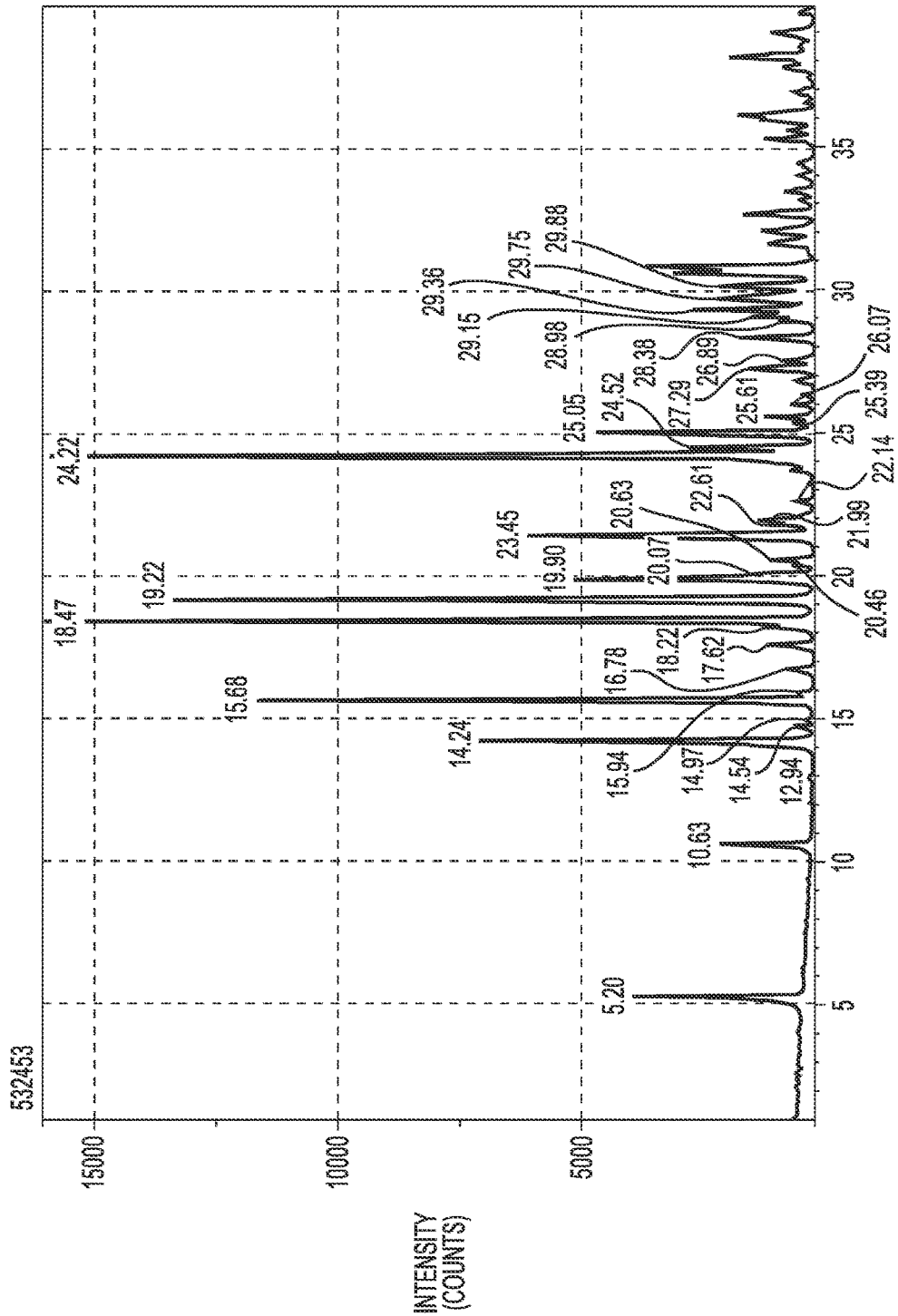
FIG. 21 is the x-ray powder diffraction pattern for glycopyrrolate bromide.
Figure 23:
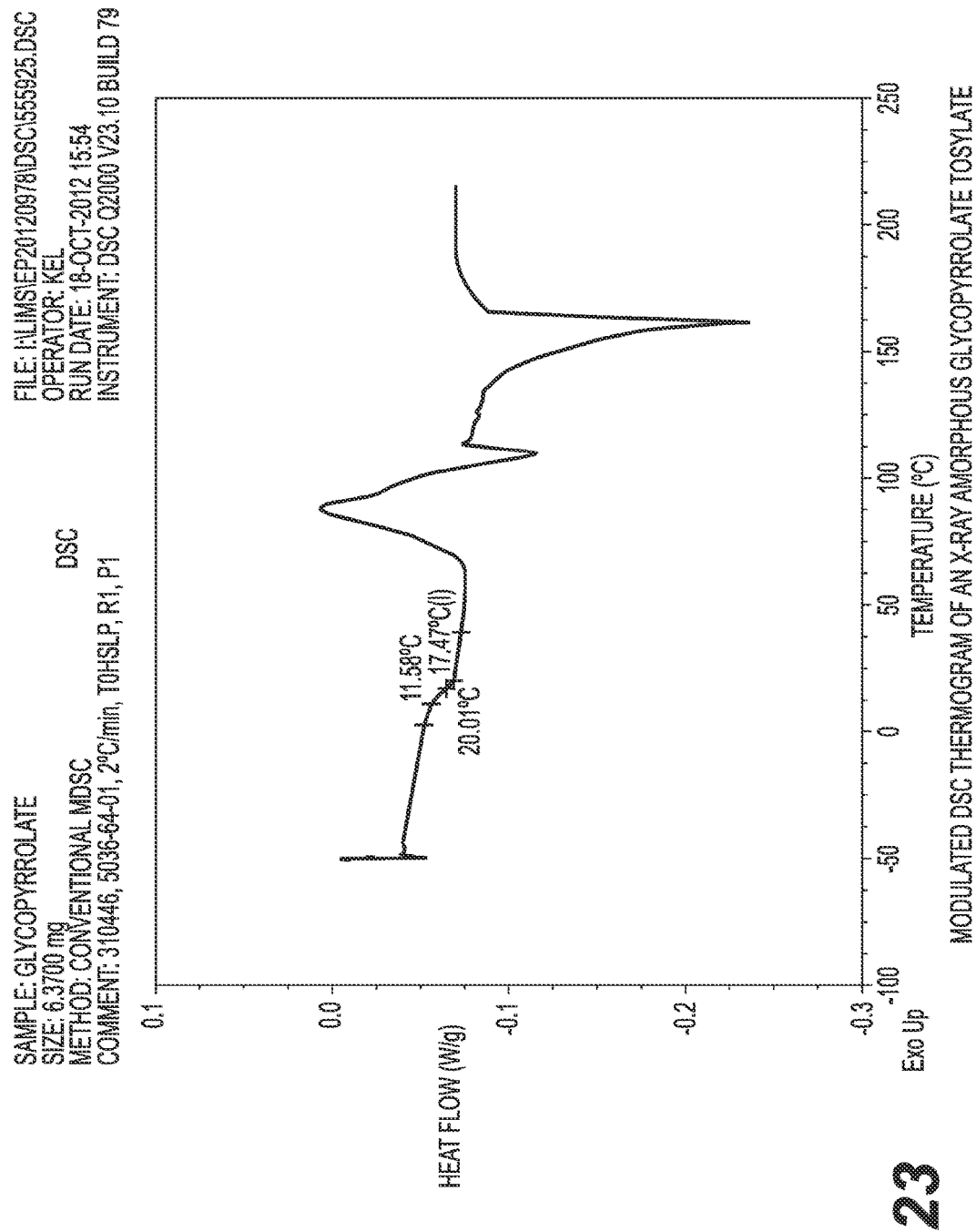
FIG. 23 is the modulated DSC thermogram of an x-ray amorphous glycopyrrolate tosylate.

The amorphous glycopyrrolate tosylate of the invention was observed to be amorphous by X-ray diffraction in that it had contained the "amorphous halo" associated with amorphous solids. Such a material is often called "x-ray amorphous." As used herein, "amorphous" when describing glycopyrrolate tosylate means amorphous as determined by x-ray powder diffraction such as, for example, as shown in FIG. 19. DSC and thermogravimetric data for an x-ray amorphous form are shown in FIG. 20 whereas the modulated DSC thermogram is set forth in FIG. 23.

Amorphous glycopyrrolate tosylate was found to be extremely hygroscopic which deliquesced readily when exposed to standard atmospheric conditions. In addition, the extremely low glass transition renders the amorphous form of glycopyrrolate challenging to formulate successfully. However, applicants have been able to raise the glass transition temperature, and reduce the likelihood of deliquescence by preparing solid dispersions of glycopyrrolate tosylate.

Solid dispersions can be prepared in a number of different methods known in the art including lyophilization and spray drying. The solid dispersions herein were all created by lyophilization. The solid dispersions prepared herein are set forth in the Examples and may be prepared by combining a solution of glycopyrrolate tosylate with a solution of an excipient in one or more solvents where both components are soluble. The solutions may be filtered and are then cooled so that the solutions freeze. After freezing, the solutions are dried, such as in a lyophilizer, so as to form dispersions. The presence of a solid dispersion can be verified by comparing, for example, spectra of the starting materials with the purported dispersion or by observing a glass temperature different than either of the components. A mixture would be evident by a simply linear combination of the peaks of the two starting materials whereas in a dispersion, peak shifts indicate the preparation of a different material, namely, a solid dispersion. A solid dispersion is also evident by the presence of a single glass transition temperature.

A solid dispersion comprising glycopyrrolate tosylate and excipients including monosaccharides, disaccharides, and pharmaceutically acceptable polymers containing cyclic ether moieties may be formed under suitable conditions such as by lyophilization. In some embodiments, such solid dispersions have a glass transition temperature of at least about 25° C. including at least about 40° C. and at least about 60° C. In these and other embodiments, the weight ratio of sucrose to glycopyrrolate tosylate is about 9:1. In other embodiments, the cyclic ethers are six-membered rings, such as in hypromellose acetate succinate (HPMCAS) and such solid dispersions have a glass transition temperature of at least about 25° C. including at least about 40° C. and at least about 60° C. In these and other embodiments, the weight ratio of HPMCAS to glycopyrrolate tosylate is about 1:1.

A solid dispersion comprising glycopyrrolate tosylate and excipients including pharmaceutically acceptable polymers containing polyethylene glycol moieties such as a polyvinyl alcohol-polyethylene glycol graft copolymer, such as Kollicoat® IR, or a polyvinyl caprolactam-polyvinyl acetate-polyethylene glycol graft copolymer, such as Soluplus®, may be formed under suitable conditions such as by lyophilization. In some embodiments, such solid dispersions have a glass transition temperature of at least about 30° C. including at least about 40° C.

A solid dispersion comprising glycopyrrolate tosylate and excipients including pharmaceutically acceptable polymers containing vinyl pyrrolidone moieties such as polyvinyl pyrrolidone or vinyl pyrrolidone-vinyl acetate copolymer may be formed under suitable conditions such as by lyophilization. In some embodiments, such solid dispersions have a glass transition temperature of at least about 25° C. including at least about 35° C. and further including about 60° C. Examples of polyvinyl pyrrolidone polymers used herein include PVP K29/32 and PVP K90. Examples of a vinyl pyrrolidone-vinyl acetate copolymer used herein include Kollidon® VA 64.

As used herein, the term "a pharmaceutically acceptable polymer" means a polymer approved for use in humans in pharmaceutical formulations including those polymers not yet approved but for whom approval is pending.

Figure 24:
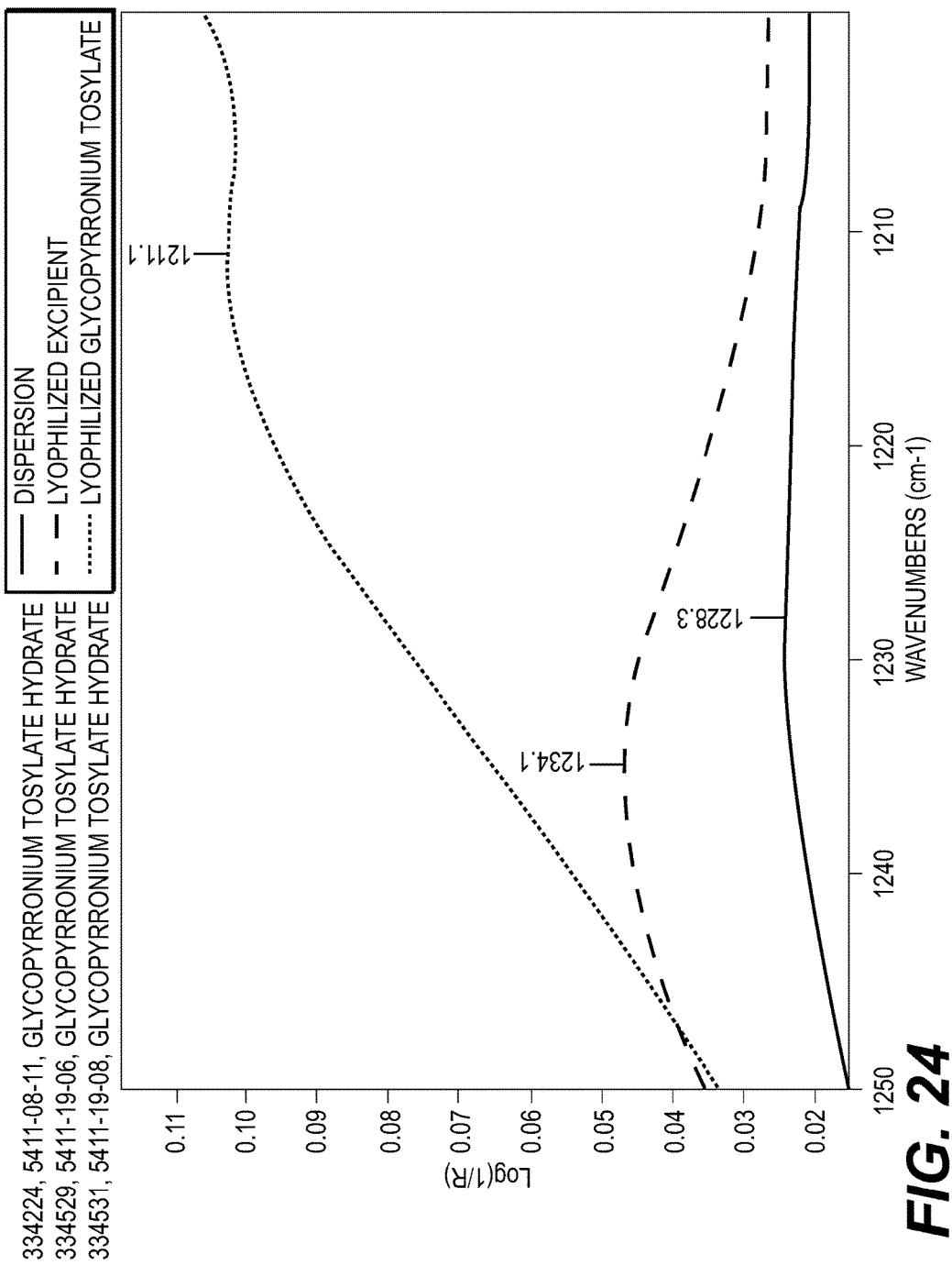
FIG. 24 is an overlay of a portion of the infrared spectrum of a solid dispersion of HPMCAS:glycopyrrolate tosylate (1:1) and its respective components.
Figure 25:
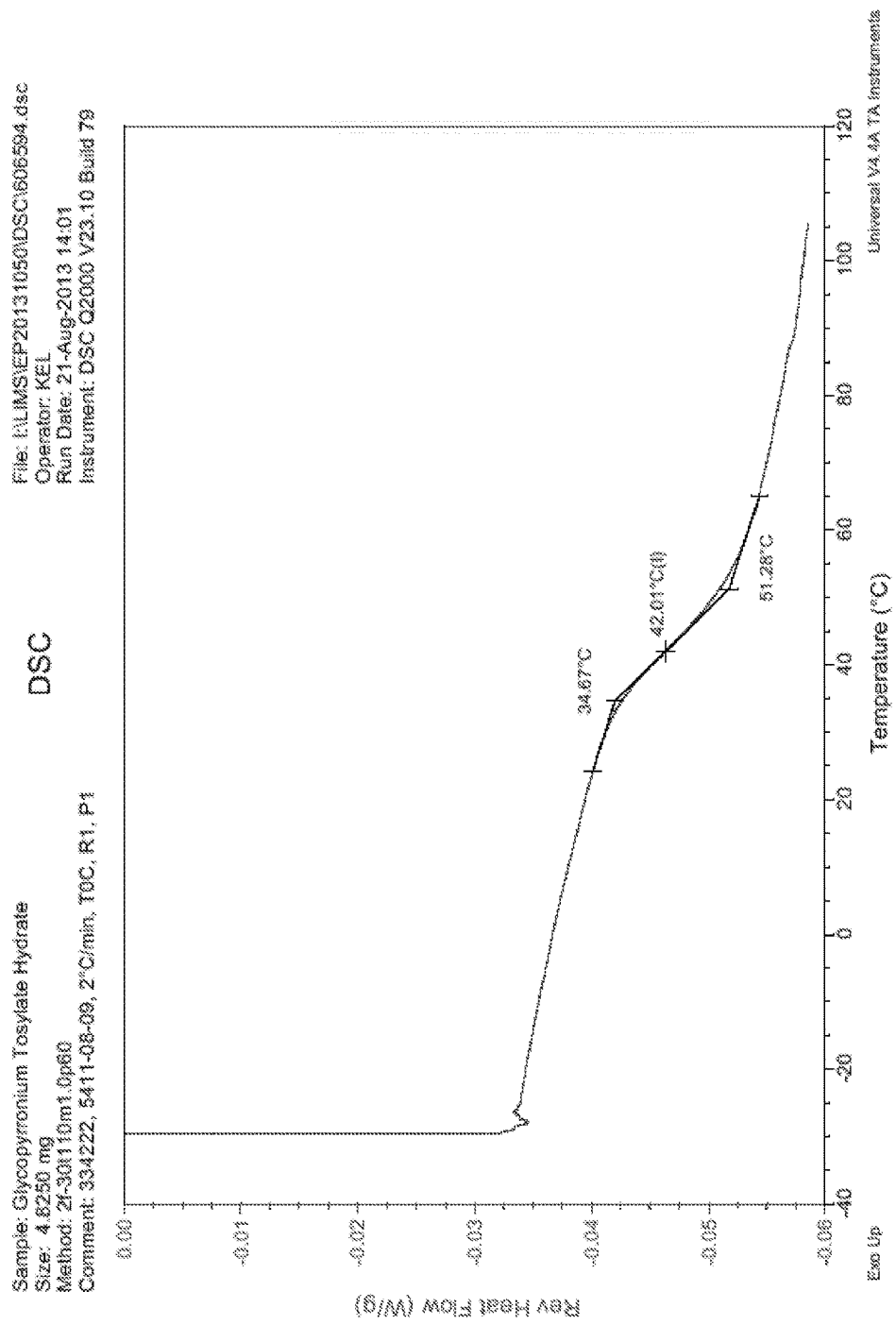
FIG. 25 is the modulated DSC thermogram of a solid dispersion of HPMCAS:glycopyrrolate tosylate (1:1).

HPMCAS may be used to form a solid dispersion with glycopyrrolate tosylate in, for example, a ratio of about 1 to 1 of HPMCAS to glycopyrrolate by weight. An example of such a preparation can be found in Example 19. FIG. 24 is an overlay infrared spectrum of a region of the spectrum showing differences between the dispersion and the component parts. For example, there is a peak at about 1211 $cm^{-1}$ in the glycopyrrolate tosylate spectrum and a peak at about 1235 $cm^{-1}$ in the HPMCAS spectrum. By comparison, in the solid dispersion spectrum, a single peak appears at about 1228 $cm^{-1}$ indicating the material is not a physical mixture. This is confirmed with FIG. 25 which shows a single glass transition temperature (also sometimes referred to as Tg) at about 42° C.

The solid 1:1 dispersion of HPMCAS and glycopyrrolate tosylate may be characterized by either its infrared spectrum, glass transition temperature or both. For example, a 1:1 solid dispersion of HPMCAS:glycopyrrolate tosylate may be characterized by a peak at about 1228 $cm^{-1}$, a glass transition temperature of about 42° C., or both.

Figure 26:
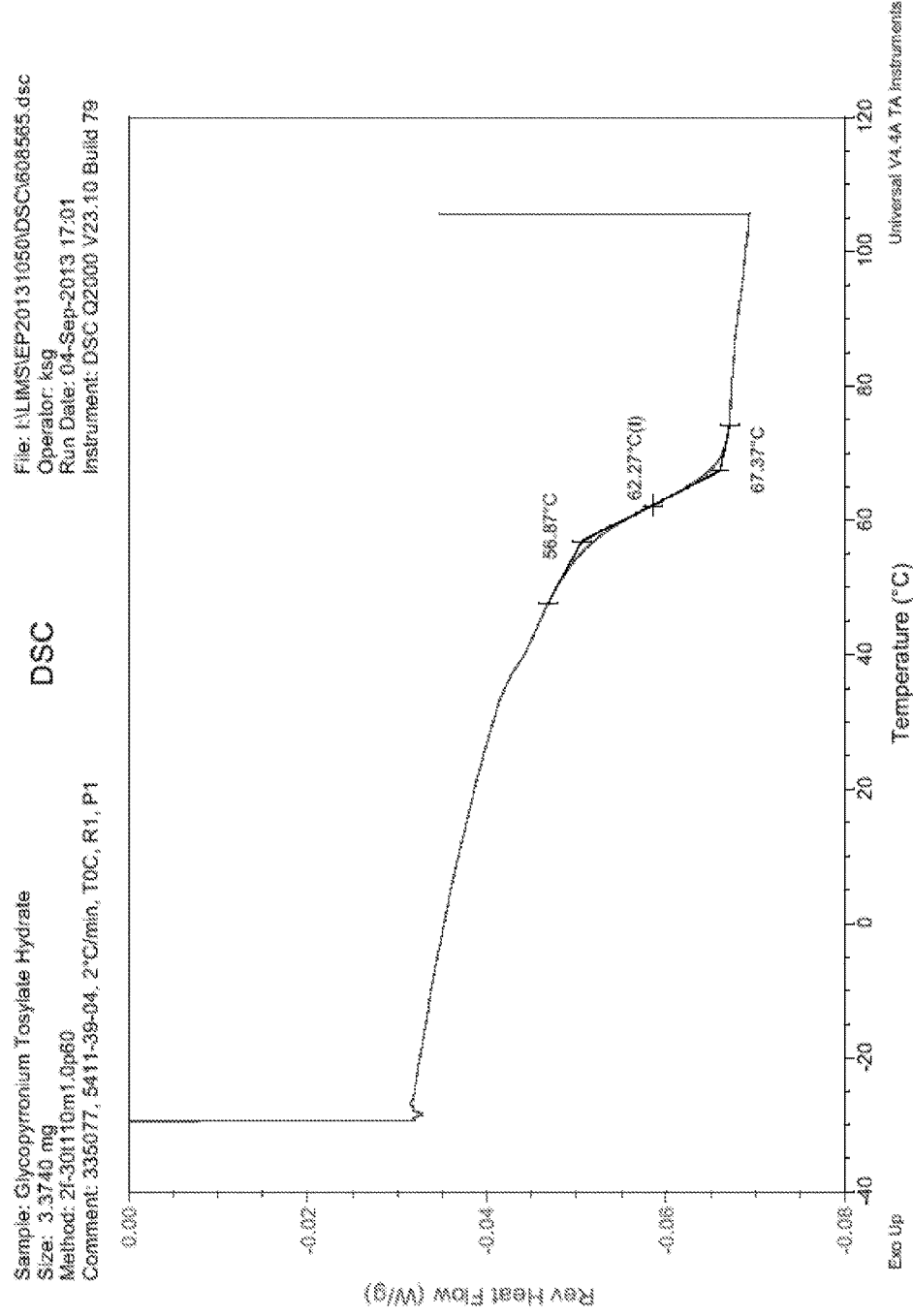
FIG. 26 is the modulated DSC thermogram of a solid dispersion of sucrose:glycopyrrolate tosylate (9:1).

Sucrose may be used to form a solid dispersion with glycopyrrolate tosylate in, for example, a ratio of about 9 to 1 of sucrose to glycopyrrolate by weight. An example of such a preparation can be found in Example 20. FIG. 26 shows a single glass transition temperature at about 62° C. confirming the presence of a solid dispersion. This glass transition temperature may be used to characterize the dispersion.

Figure 27A:
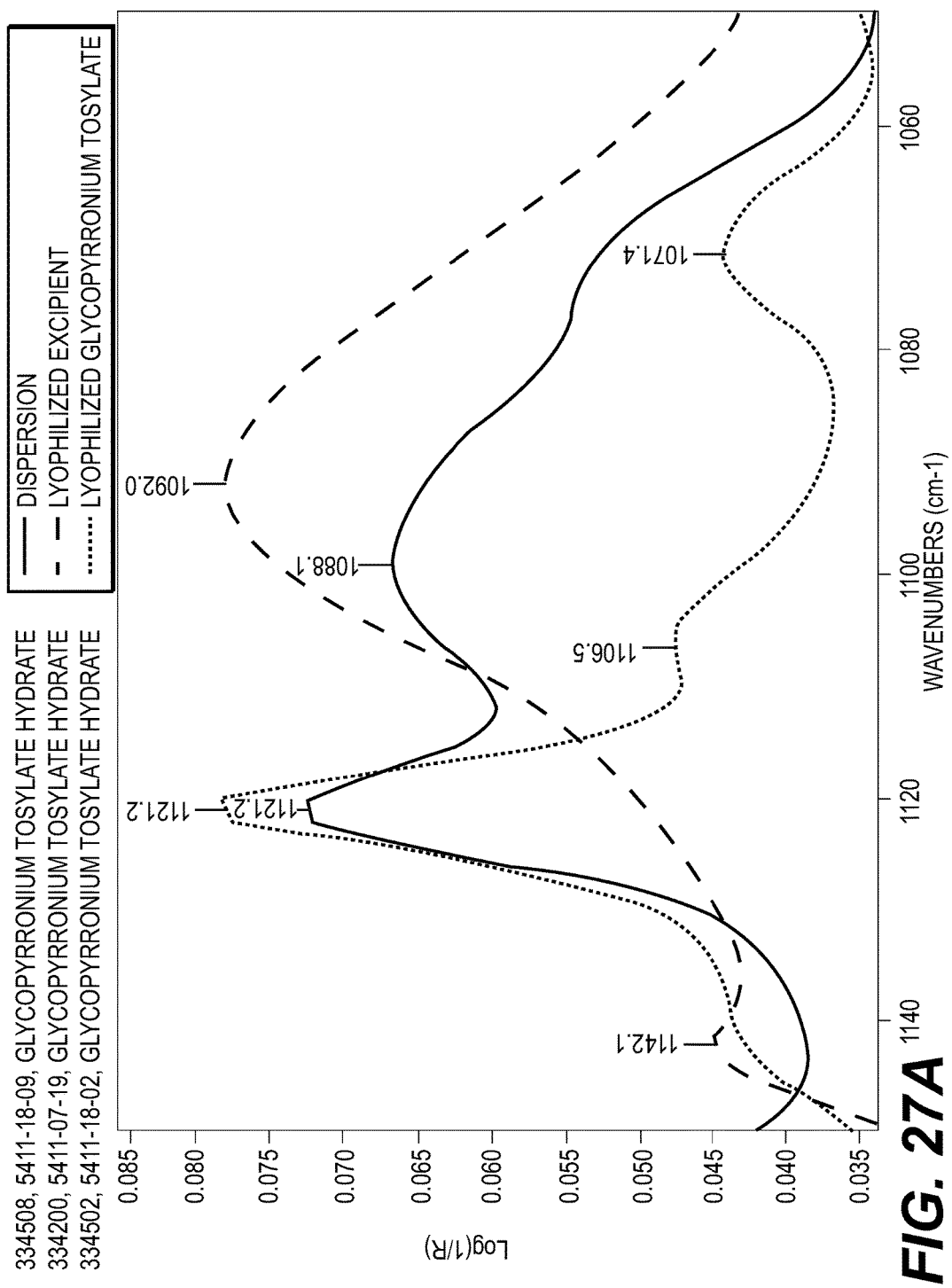
FIG. 27a is an overlay of a portion of the infrared spectrum of a solid dispersion of Kollicoat® IR:glycopyrrolate tosylate (1:1) and its respective components.
Figure 27B:
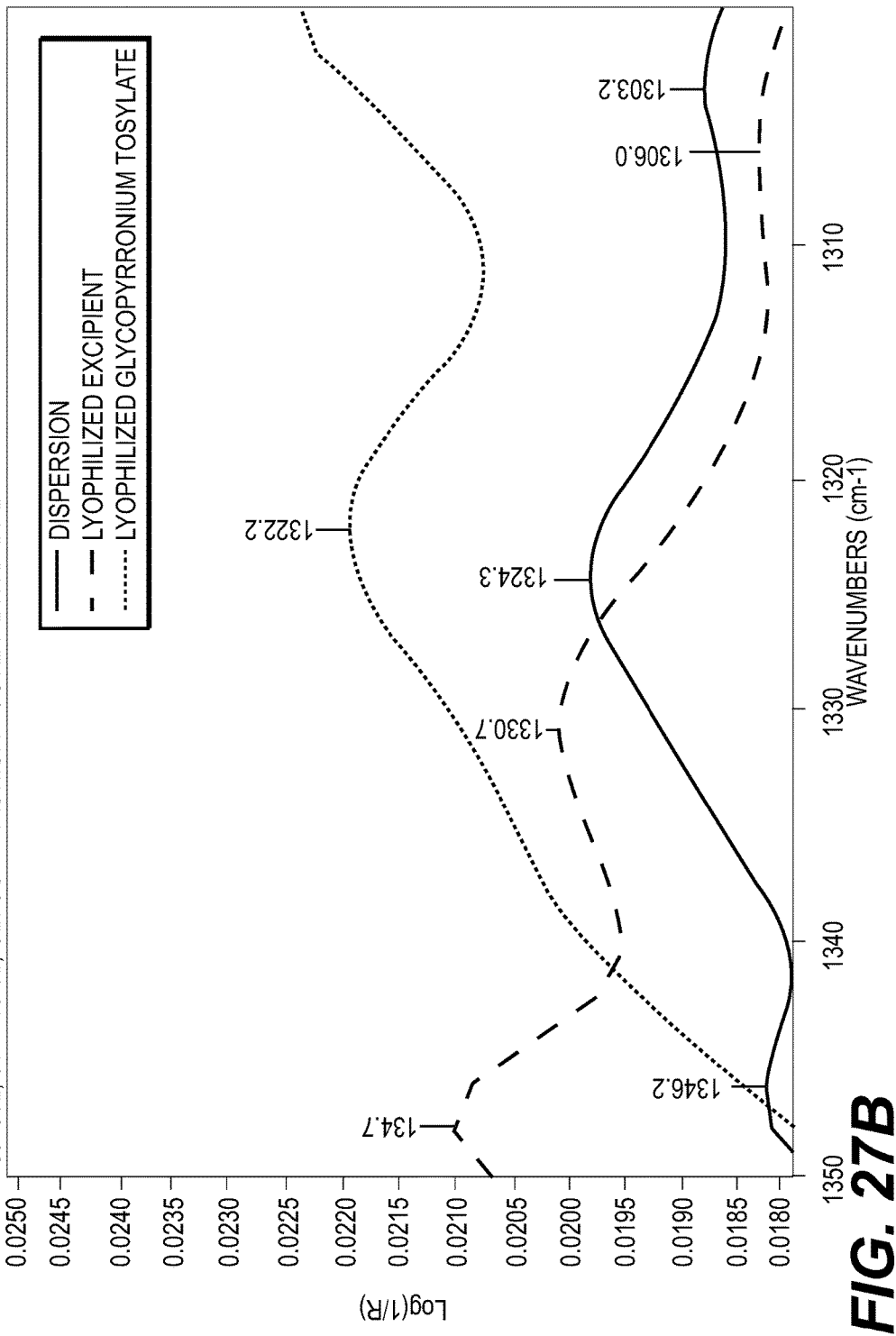
FIG. 27b is an overlay of a portion of the infrared spectrum of a solid dispersion of Kollicoat® IR:glycopyrrolate tosylate (1:1) and its respective components.
Figure 28:
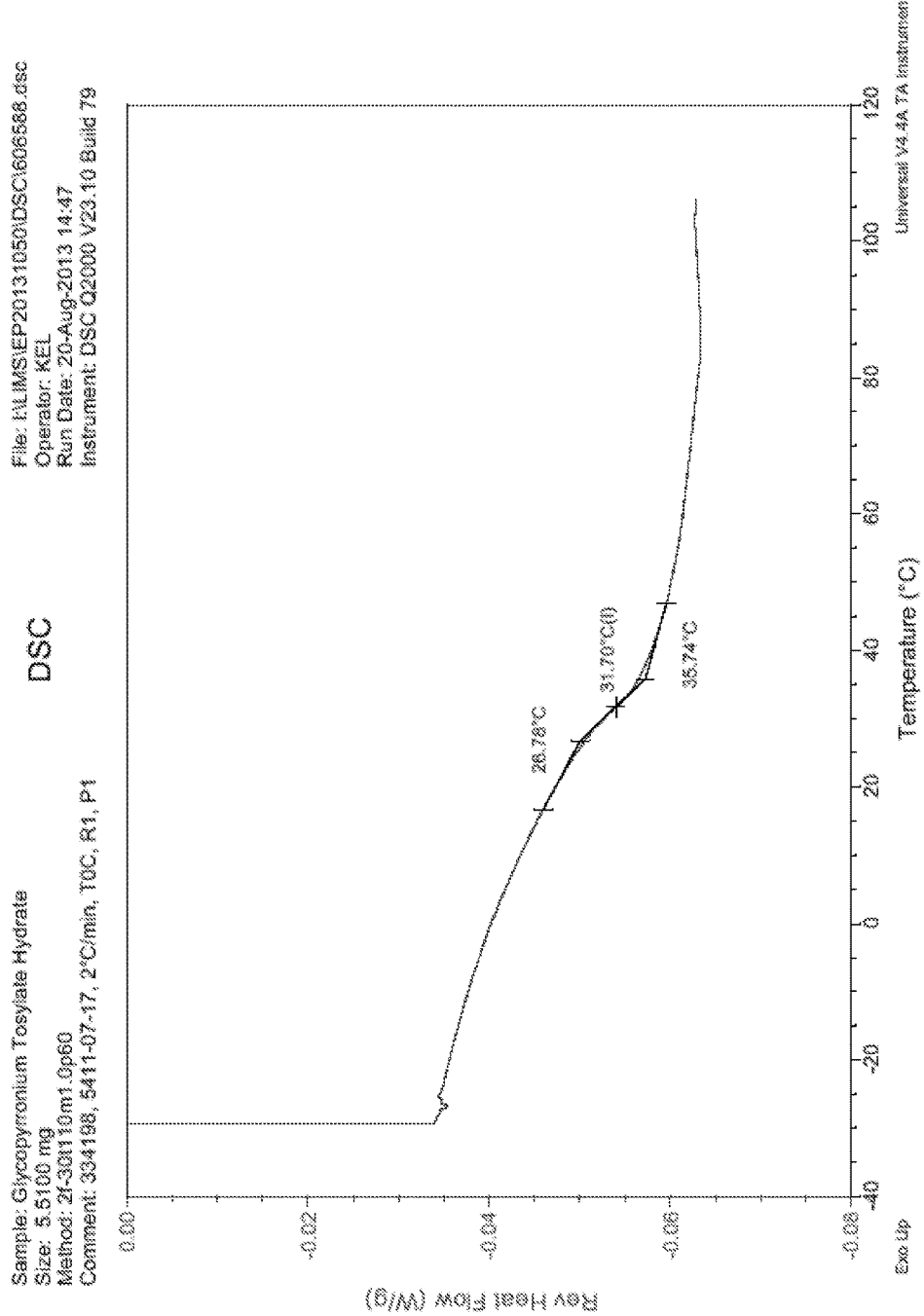
FIG. 28 is the modulated DSC thermogram of a solid dispersion of Kollicoat® IR:glycopyrrolate tosylate (1:1).
Figure 29:
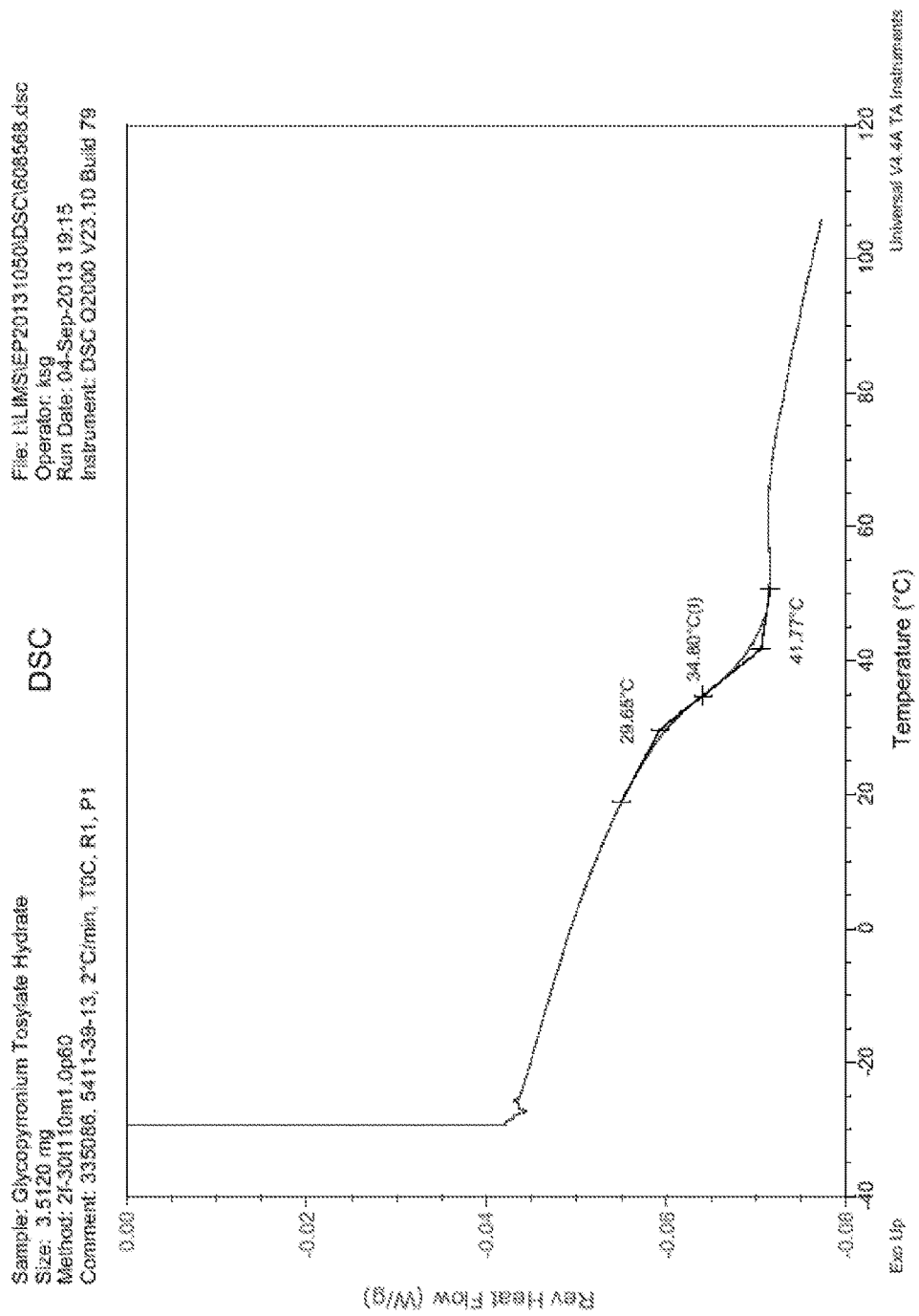
FIG. 29 is the modulated DSC thermogram of a solid dispersion of Kollicoat® IR:glycopyrrolate tosylate (9:1).

A polyvinyl alcohol-polyethylene glycol copolymer may be used to form a solid dispersion with glycopyrrolate tosylate, in, for example, ratios of between about 1:1 and 9:1. An example of the 1:1 dispersion preparation can be found in Example 21 and a 9:1 dispersion in Example 22. FIGS. 27a and 27b are overlay infrared spectra of two regions of the spectrum showing differences between the 1:1 dispersion and the component parts. For example, there are peaks at about 1107 $cm^{-1}$ and 1322 $cm^{-1}$ in the glycopyrrolate tosylate spectrum and peaks at about 1092 $cm^{-1}$ and 1331 $cm^{-1}$ in the polyvinyl alcohol-polyethylene glycol copolymer spectrum. By comparison, in the solid dispersion spectrum, a single peak now appears at about 1099 $cm^{-1}$ and 1324 $cm^{-1}$ respectively indicating the material is not a physical mixture. This is confirmed with FIG. 28 which shows a single glass transition temperature (Tg) at about 32° C. FIG. 29 shows a single glass transition temperature of the 9:1 dispersion to be at about 35° C.

The 1:1 solid dispersion of a polyvinyl alcohol-polyethylene glycol copolymer and glycopyrrolate tosylate may be characterized by its infrared spectrum, glass transition temperature, or both. For example, one or more peaks in the infrared spectrum of the dispersion at about 1099 cm$^{-1}$ and 1324 cm$^{-1}$, a glass transition temperature at about 32° C., or a combination thereof may be used to characterize the solid dispersion. The 9:1 solid dispersion may be characterized by a glass transition temperature at about 35° C.

Figure 30A:
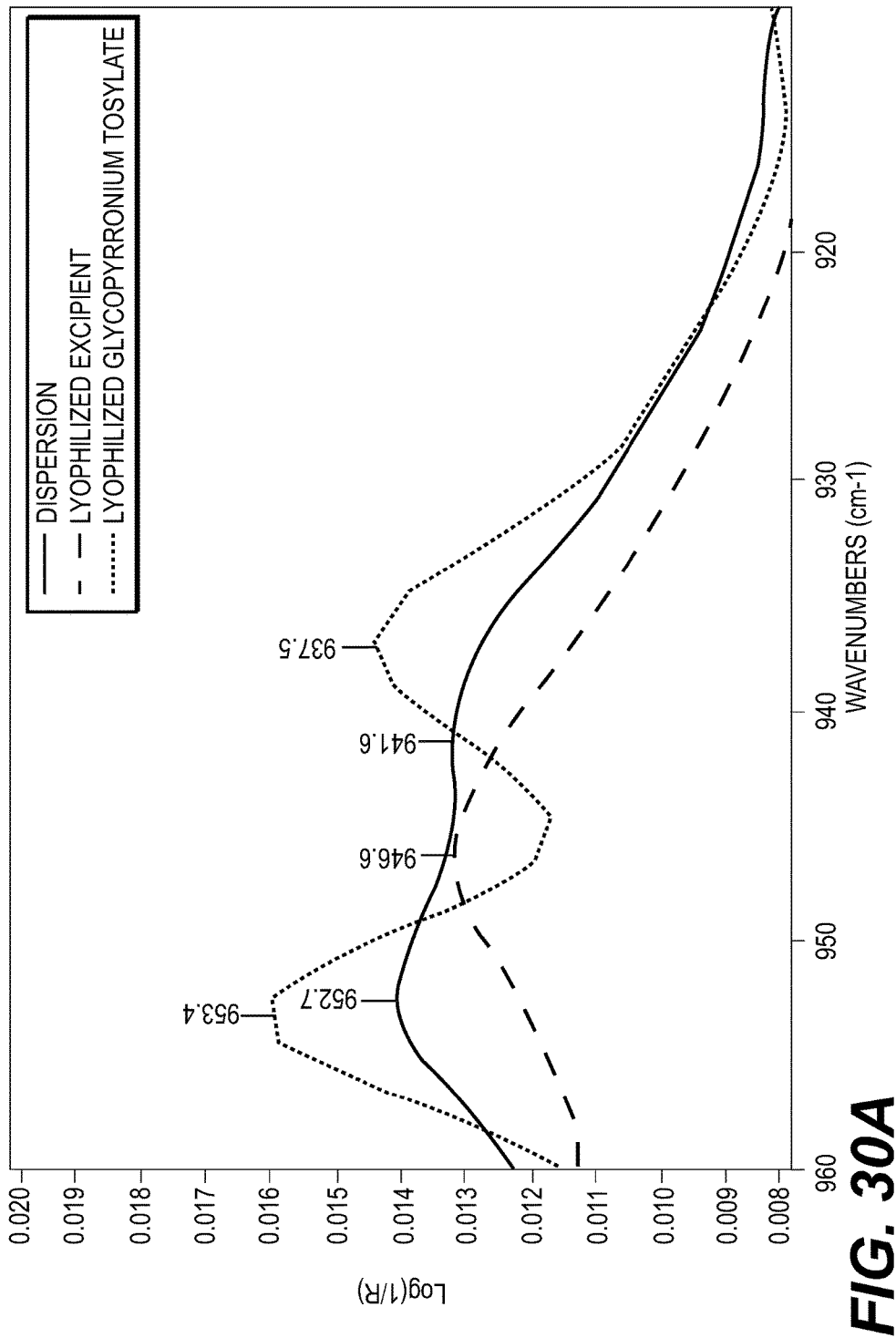
FIG. 30a is an overlay of a portion of the infrared spectrum of a solid dispersion of Soluplus®:glycopyrrolate tosylate (1:1) and its respective components.
Figure 30B:
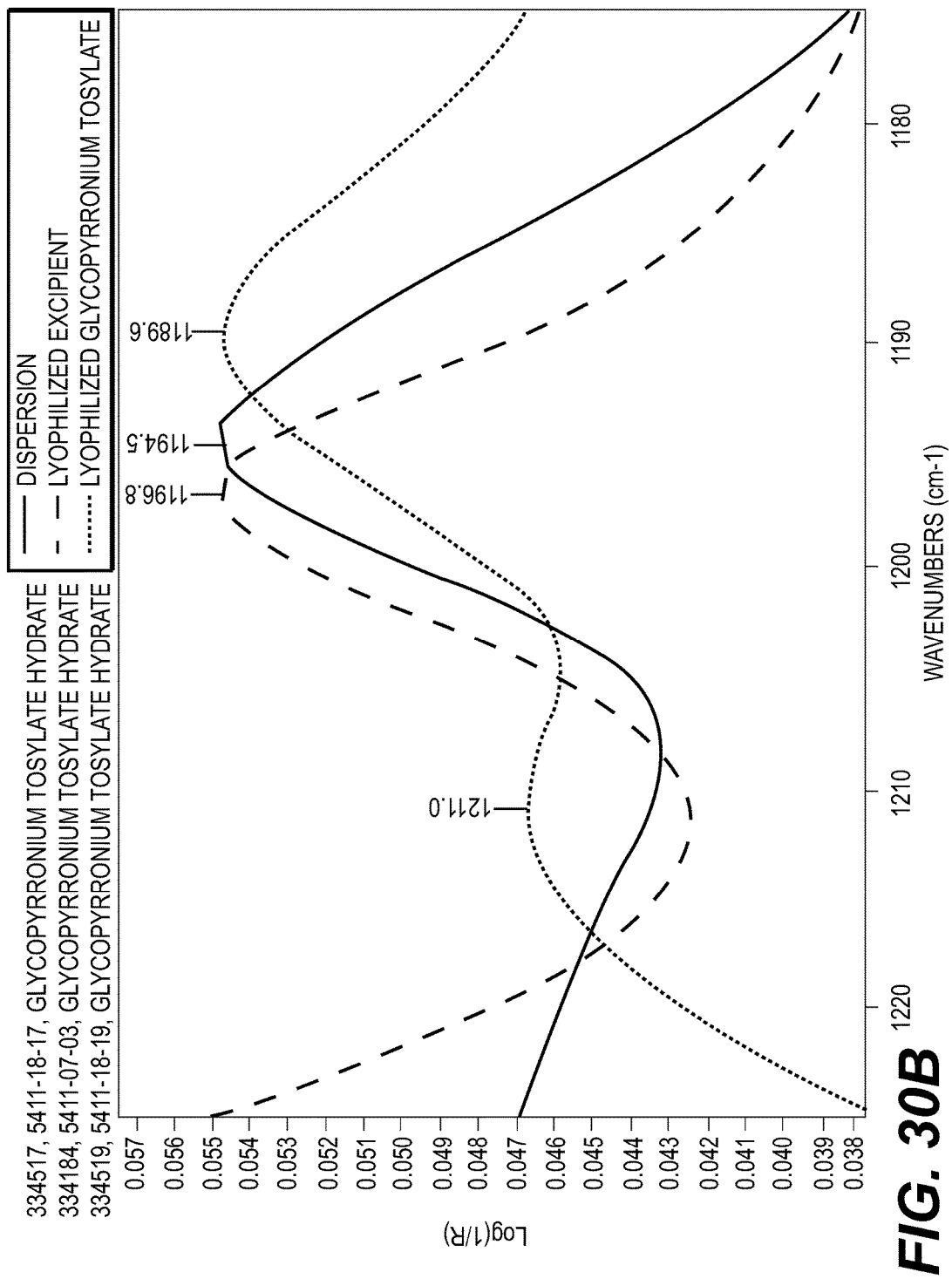
FIG. 30b is an overlay of a portion of the infrared spectrum of a solid dispersion of Soluplus®:glycopyrrolate tosylate (1:1) and its respective components.
Figure 30C:
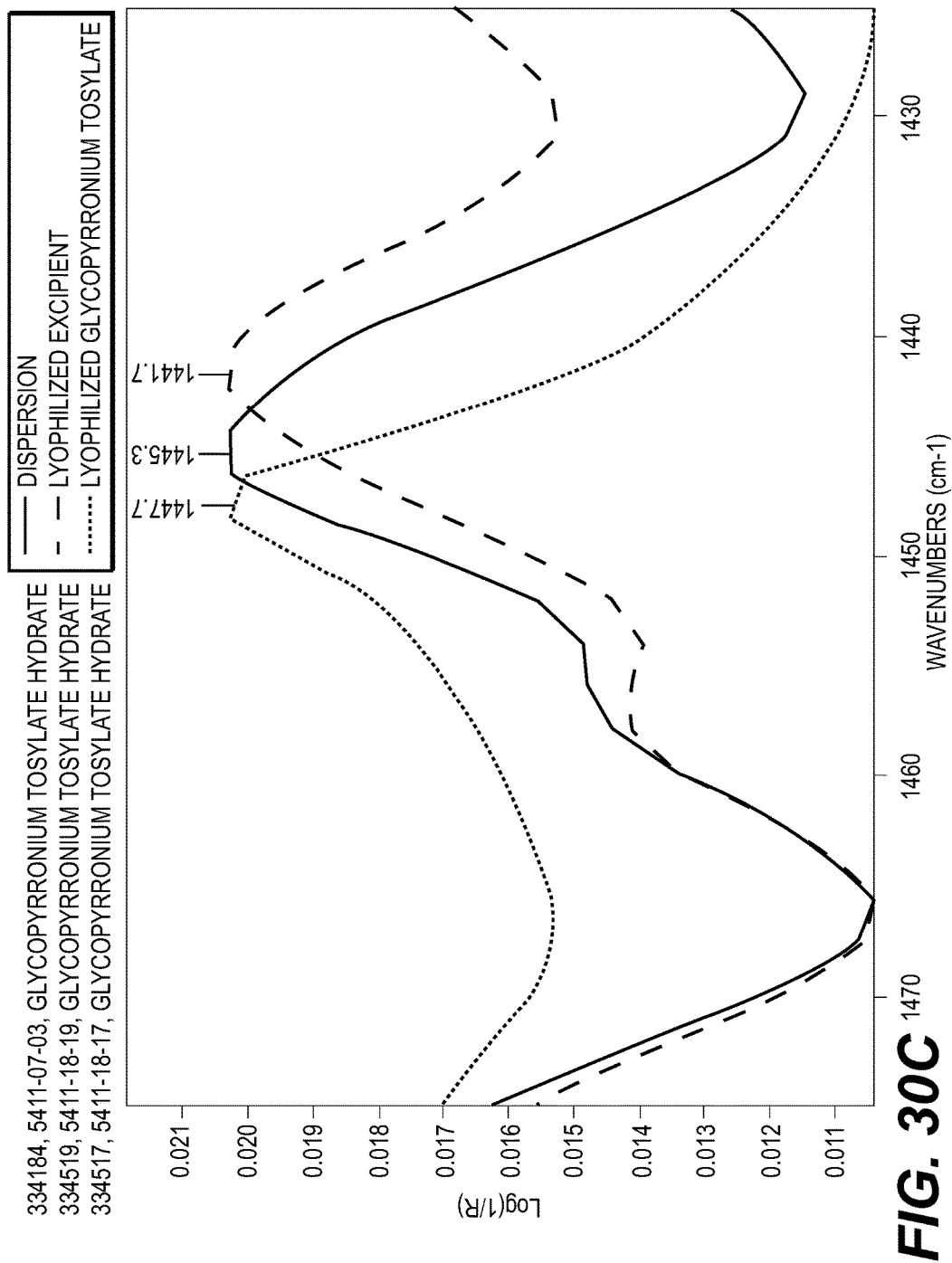
FIG. 30c is an overlay of a portion of the infrared spectrum of a solid dispersion of Soluplus®:glycopyrrolate tosylate (1:1) and its respective components.
Figure 31:
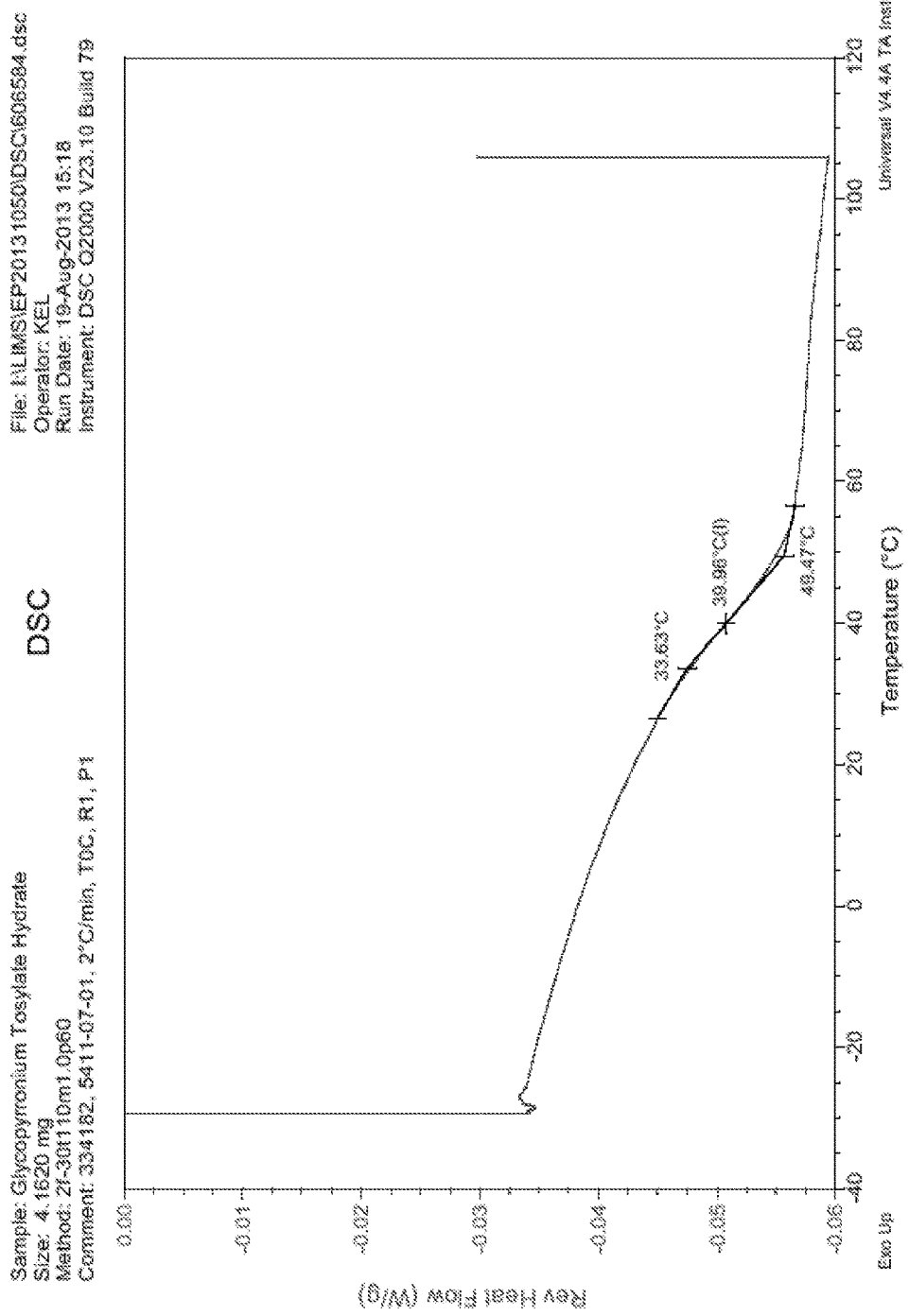
FIG. 31 is the modulated DSC thermogram of a solid dispersion of Soluplus®:glycopyrrolate tosylate (1:1).

A polyvinyl caprolactam-polyvinyl acetate-polyethylene glycol graft copolymer may be used to form a solid dispersion with glycopyrrolate tosylate in, for example, a ratio of about 1 to 1 of the polymer to glycopyrrolate by weight. An example of such a preparation can be found in Example 23. FIGS. 30a, 30b, and 30c are overlay infrared spectra of regions of the spectrum showing differences between the dispersion and the component parts. For example, there are peaks at about 938 cm$^{-1}$, about 1190 cm$^{-1}$, and about 1448 cm$^{-1}$ in the glycopyrrolate tosylate spectrum and peaks at about $^1$ and 947 cm$^{-1}$, about 1197 cm$^{-1}$, and about 1442 cm$^{-1}$ in the polyvinyl caprolactam-polyvinyl acetate-polyethylene glycol graft copolymer spectrum. By comparison, in the solid dispersion spectrum, a single peak appears at about 942 cm$^{-1}$, about 1195 cm$^{-1}$, and about 1445 cm$^{-1}$ respectively indicating the material is not a physical mixture. This is confirmed with FIG. 31 which shows a single glass transition temperature at about 40° C.

The solid 1:1 dispersion of a polyvinyl caprolactam-polyvinyl acetate-polyethylene glycol graft copolymer and glycopyrrolate tosylate may be characterized by either its infrared spectrum, glass transition temperature or both. For example, a 1:1 solid dispersion of a polyvinyl caprolactam-polyvinyl acetate-polyethylene glycol graft copolymer:glycopyrrolate tosylate may be characterized by one or more peaks at about 942 cm$^{-1}$, about 1195 cm$^{-1}$, or about 1445 cm$^{-1}$, a glass transition temperature of about 40° C., or a combination thereof.

Figure 32A:
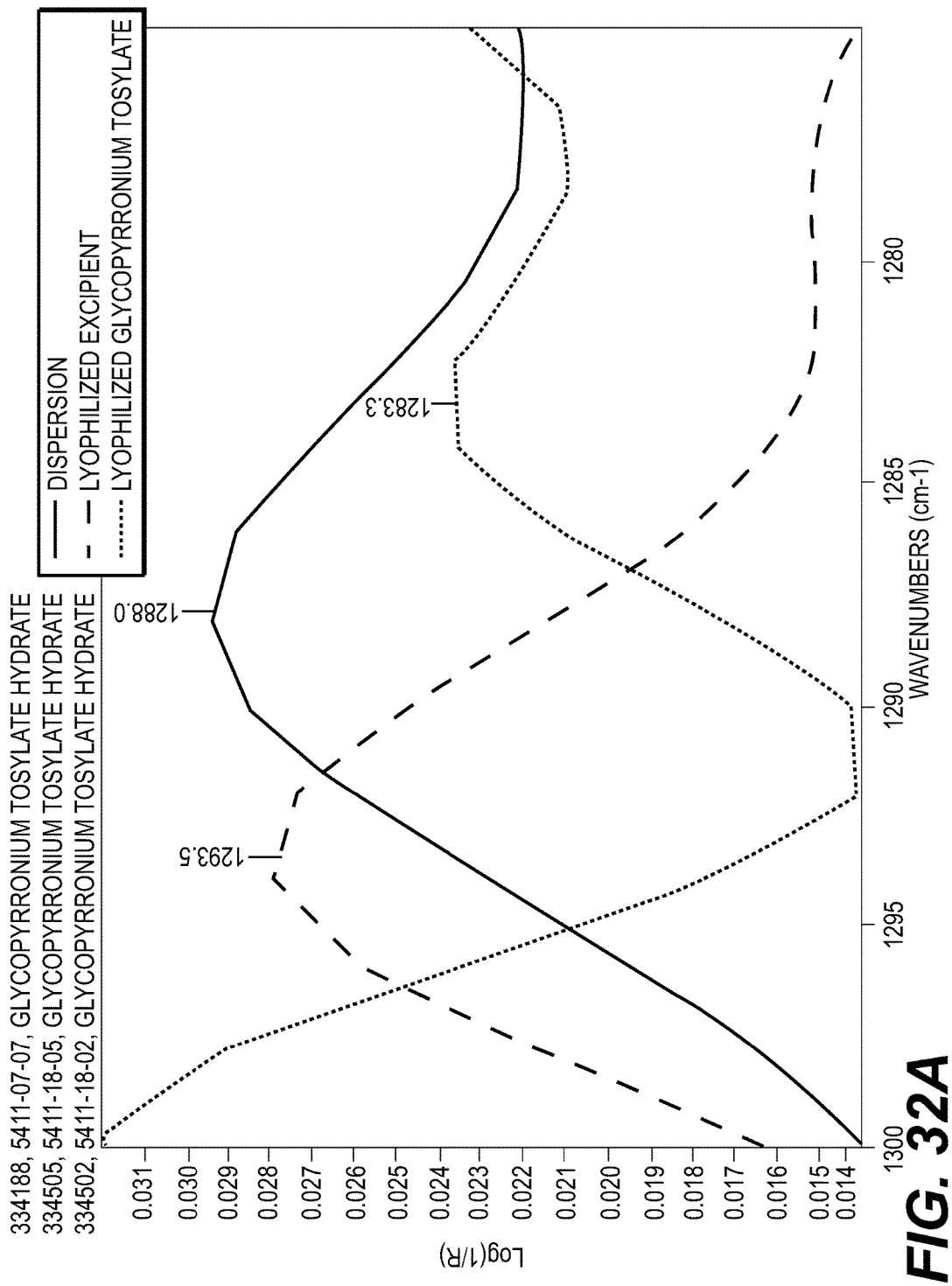
FIG. 32a is an overlay of a portion of the infrared spectrum of a solid dispersion of PVP K29/32:glycopyrrolate tosylate (1:1) and its respective components.
Figure 32B:
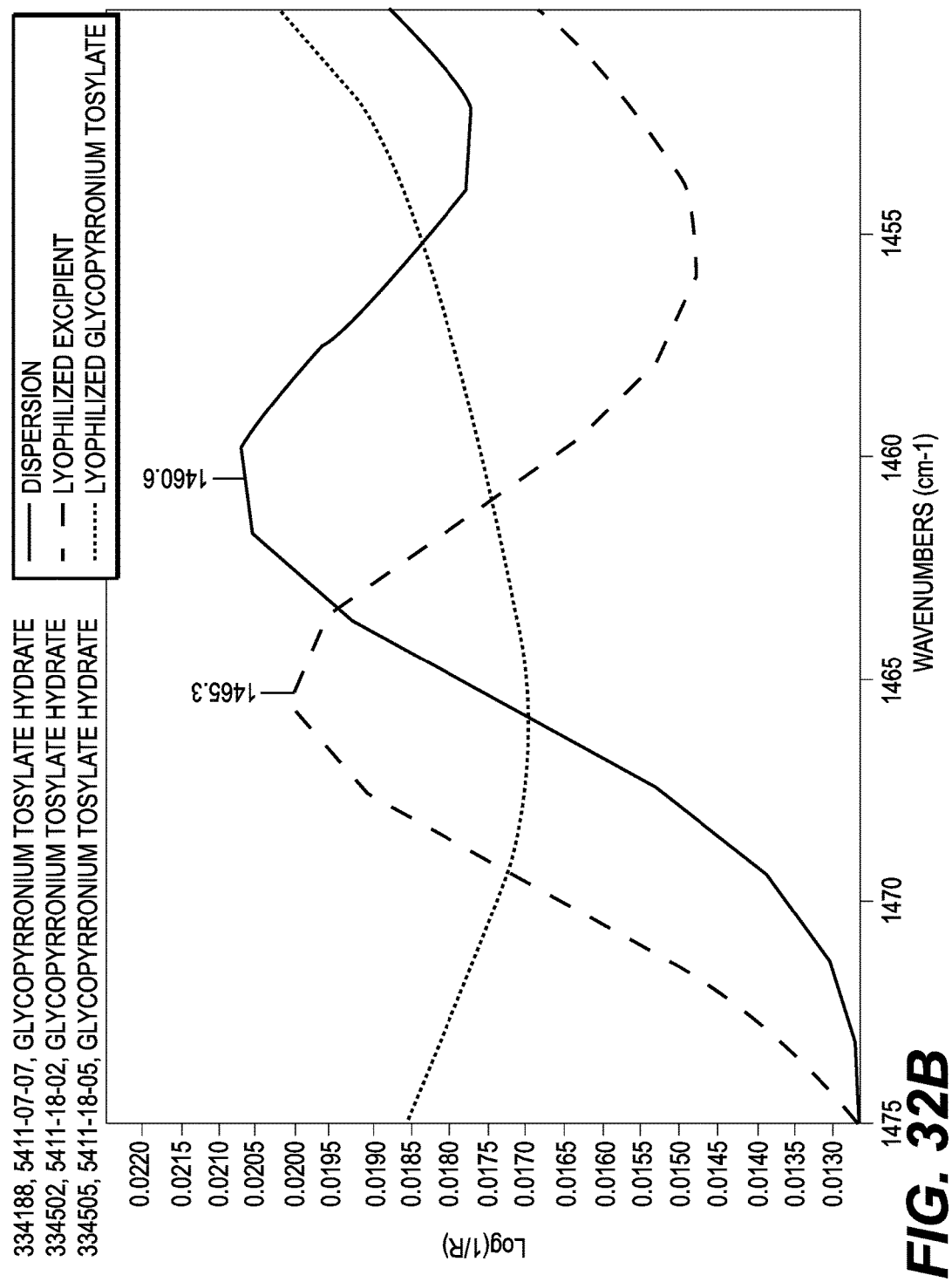
FIG. 32b is an overlay of a portion of the infrared spectrum of a solid dispersion of PVP K29/32:glycopyrrolate tosylate (1:1) and its respective components.
Figure 32C:
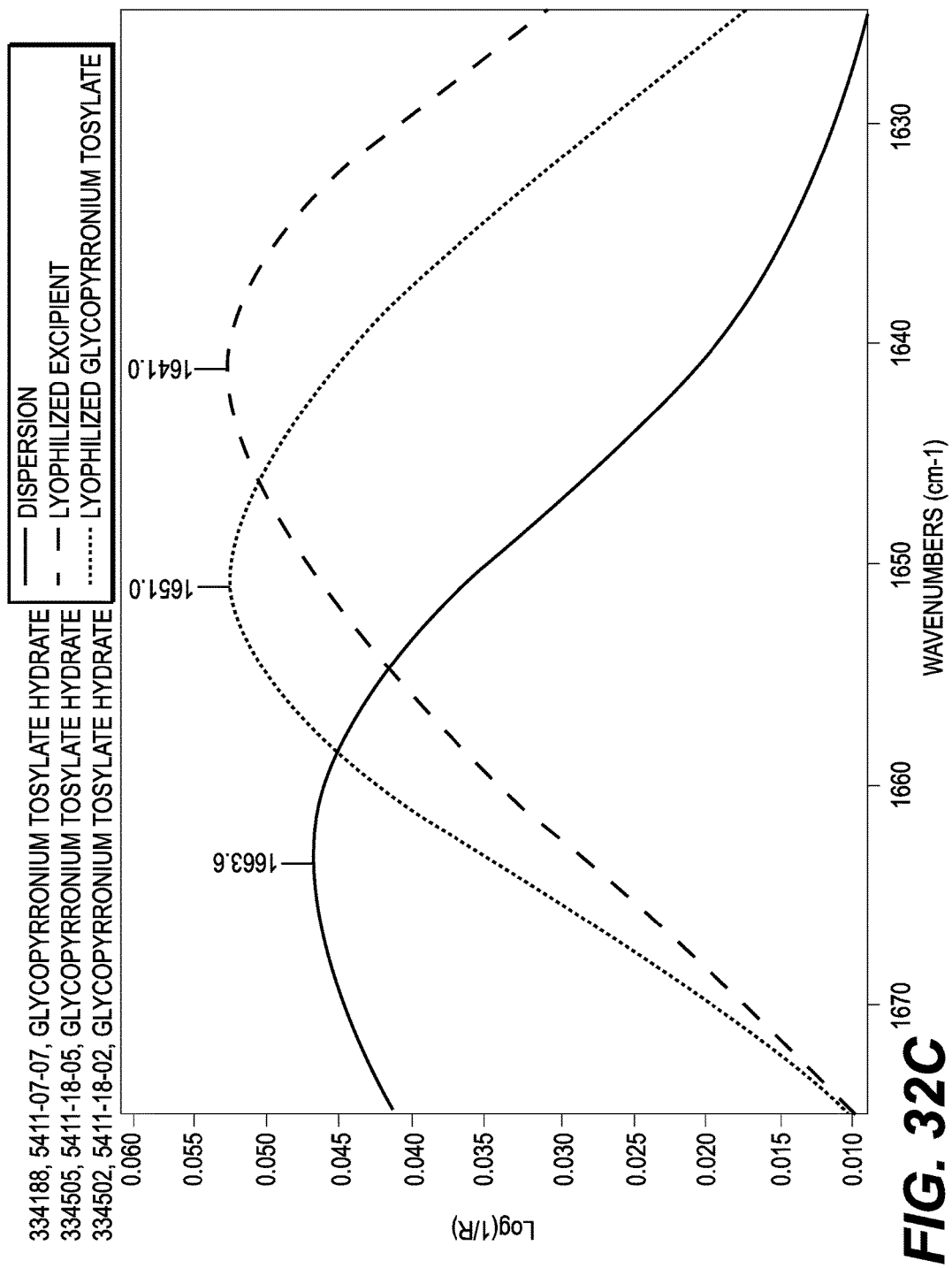
FIG. 32c is an overlay of a portion of the infrared spectrum of a solid dispersion of PVP K29/32:glycopyrrolate tosylate (1:1) and its respective components.
Figure 33:
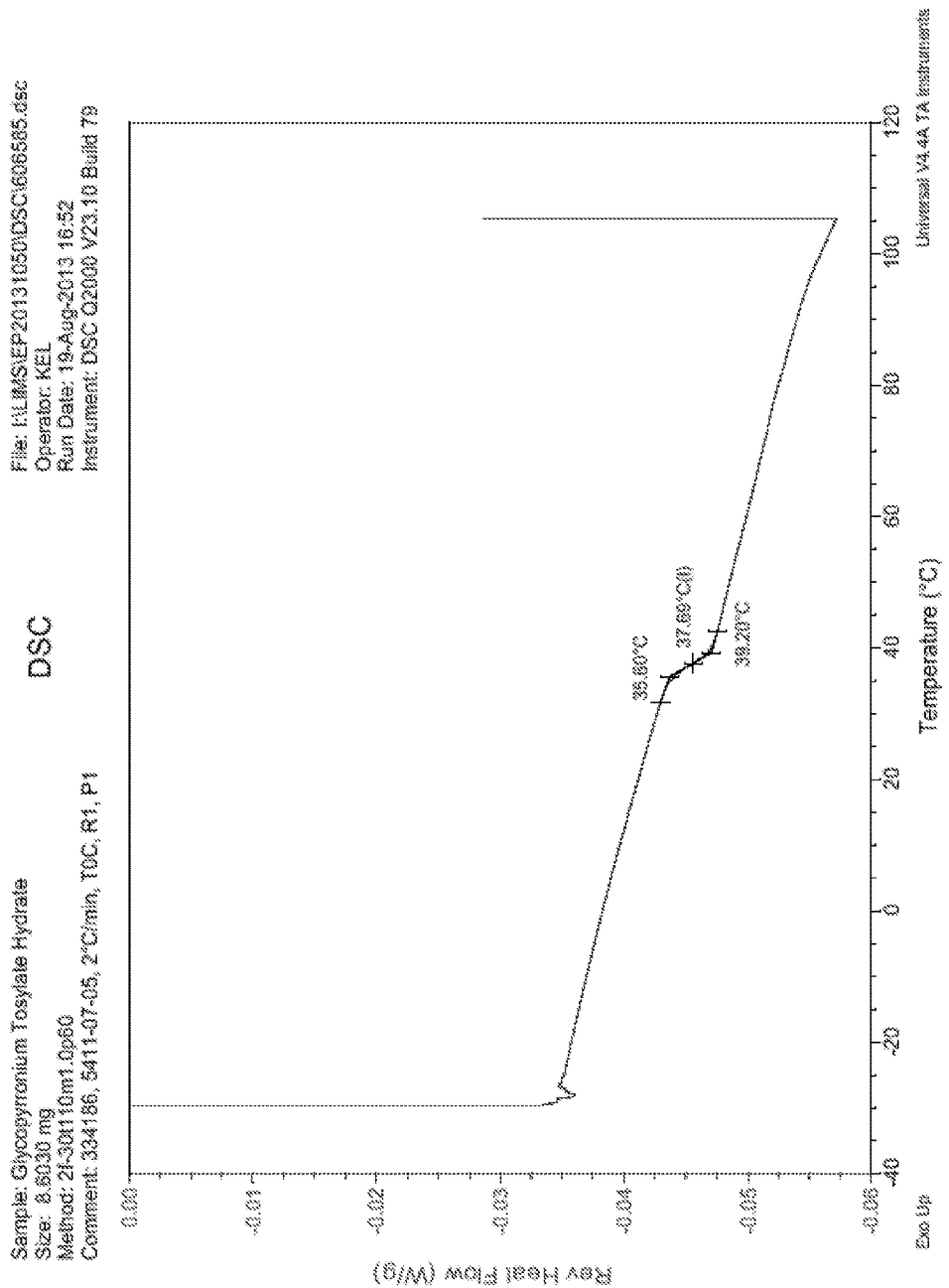
FIG. 33 is the modulated DSC thermogram of a solid dispersion of PVP K29/32:glycopyrrolate tosylate (1:1).
Figure 34:
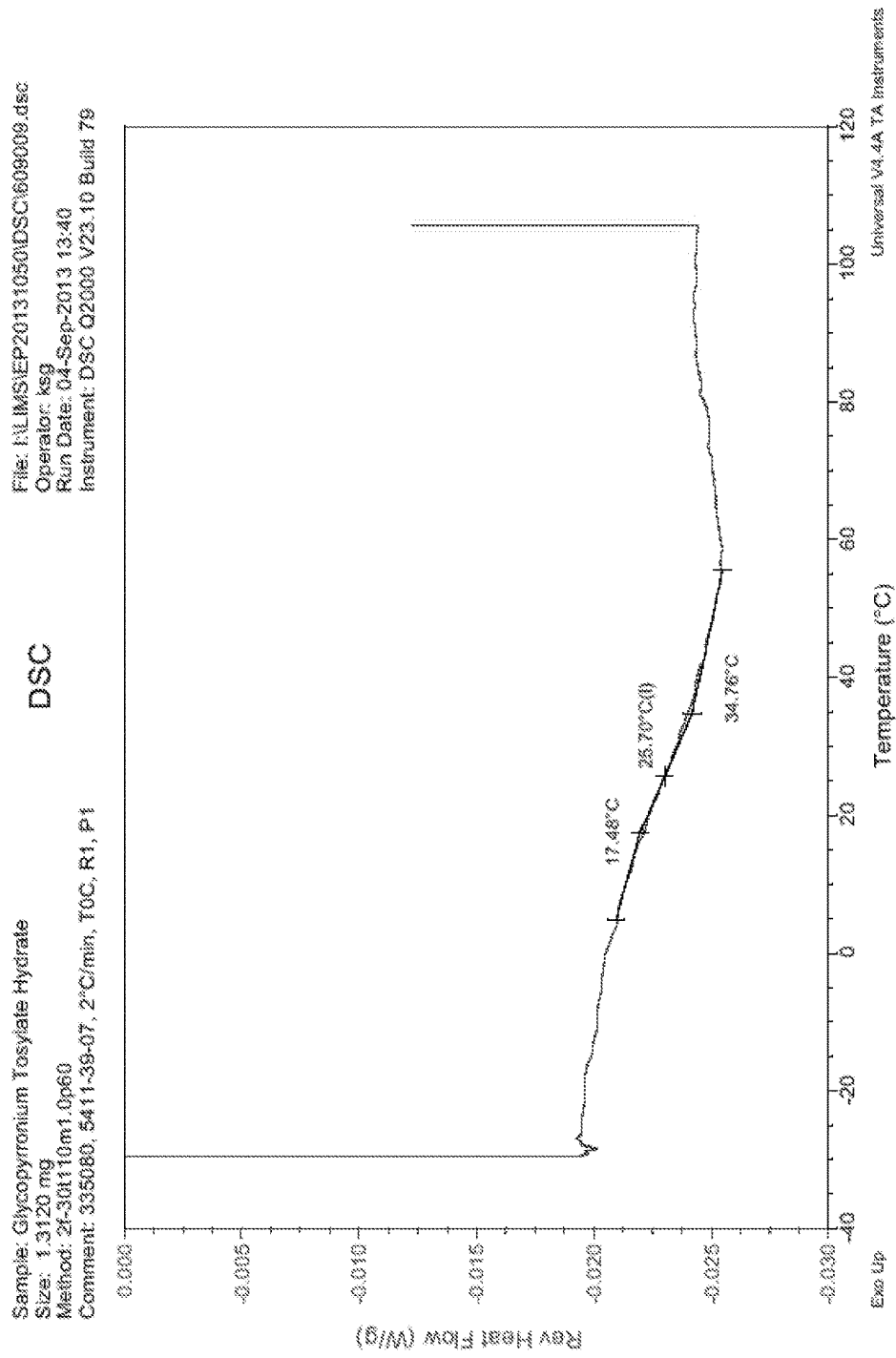
FIG. 34 is the modulated DSC thermogram of a solid dispersion of PVP K29/32:glycopyrrolate tosylate (8:1).

A polyvinyl pyrrolidone polymer may be used to form a solid dispersion with glycopyrrolate tosylate in, for example, a ratio of about 1 to 1 of the polymer to glycopyrrolate by weight or a ratio of about 8 to 1 by weight. An example of such a preparation can be found in Examples 24, 25 and 26. FIGS. 32a, 32b, and 32c are overlay infrared spectra of regions of the spectrum showing differences between the dispersion and the component parts for Example 24. For example, there are peaks at about 1283 cm$^{-1}$ and 1651 cm$^{-1}$ in the glycopyrrolate tosylate spectrum and peaks at about 1294 cm$^{-1}$, about 1465 cm$^{-1}$, and about 1641 cm$^{-1}$ in the polyvinyl pyrrolidone spectrum of Example 24. By comparison, in the solid dispersion spectrum, peaks occur at about 1288 cm$^{-1}$, about 1461 cm$^{-1}$, and about 1664 cm$^{-1}$ respectively indicating the material is not a physical mixture. Further, the dispersion exhibits a peak at about 1438 cm$^{-1}$, which has no counterpart peaks in either the polymer or the glycopyrrolate tosylate. In addition, FIG. 33 indicates a solid dispersion showing a single glass transition temperature at about 38° C. for the dispersion of Example 24. The 8:1 dispersion of Example 25 shows a single glass transition temperature of about 26° C. as seen in FIG. 34.

The 1:1 solid dispersion using the polyvinyl pyrrolidone of Example 24 may be characterized by its infrared spectrum, glass transition temperature, or both. For example, it may be characterized by one or more peaks in the infrared spectrum at 1288 cm$^{-1}$, about 1461 cm$^{-1}$, about 1664 cm$^{-1}$, or about 1438 cm$^{-1}$, a glass transition temperature of about 38° C., or a combination thereof. The 8:1 solid dispersion using the polymer of Example 25 may be characterized by a glass transition temperature of about 26° C.

Figure 32D:
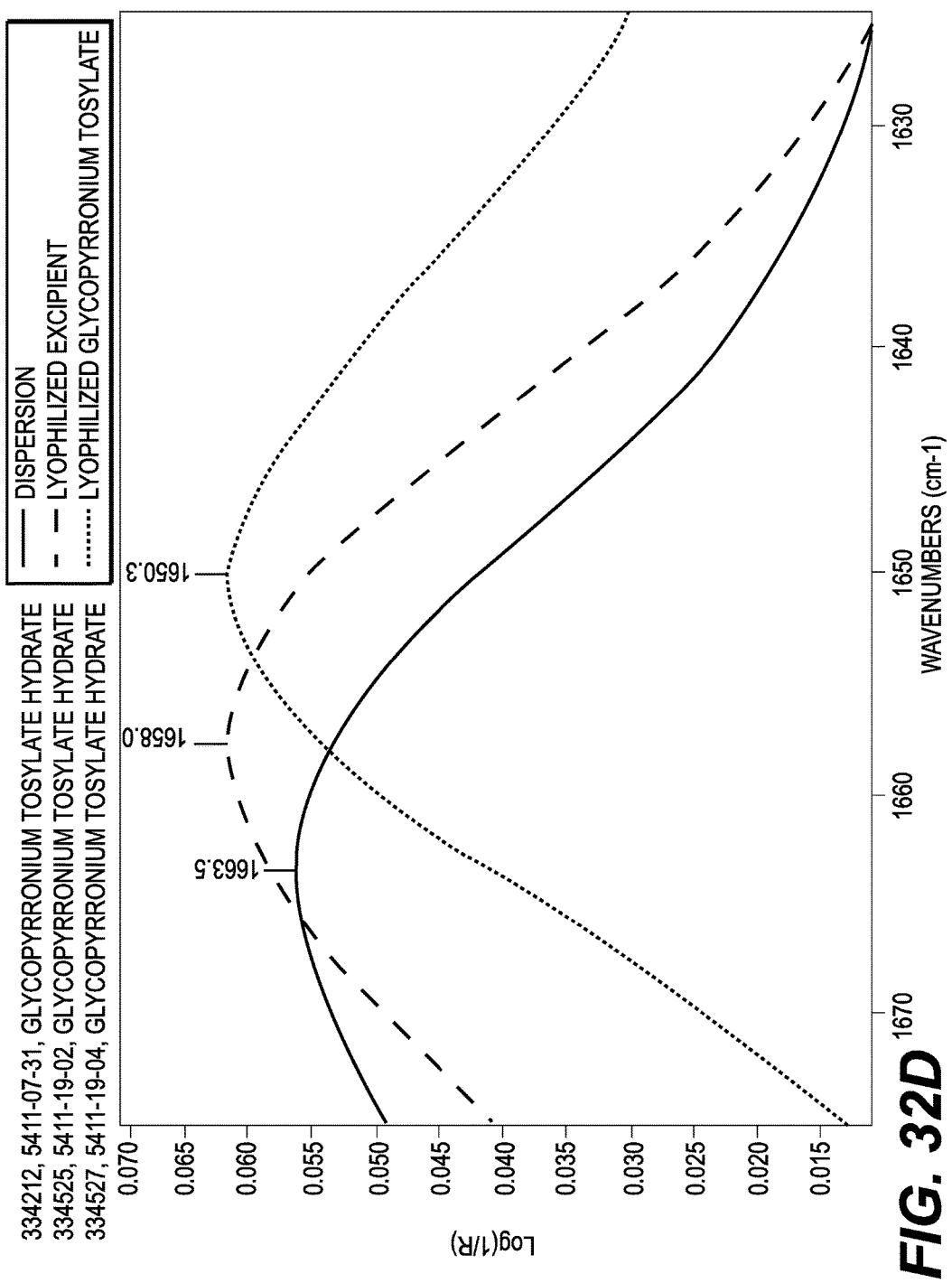
FIG. 32d is an overlay of a portion of the infrared spectrum of a solid dispersion of PVP K90:glycopyrrolate tosylate (1:1) and its respective components
Figure 35:
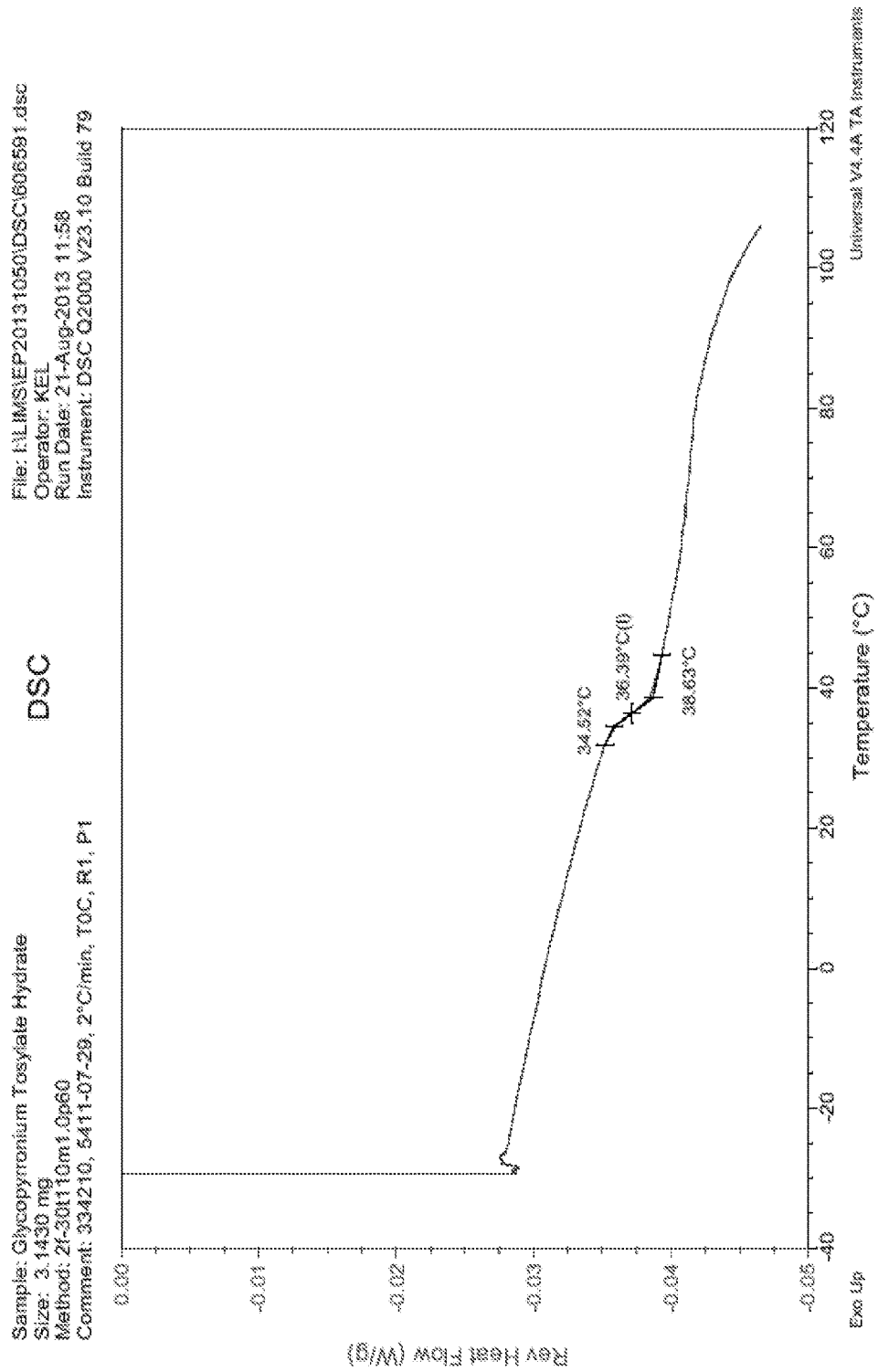
FIG. 35 is the modulated DSC thermogram of a solid dispersion of PVP K90:glycopyrrolate tosylate (1:1).

The polyvinyl pyrrolidone of Example 26 was used to prepare an approximately 1 to 1 solid dispersion of polyvinyl pyrrolidone to glycopyrrolate tosylate. FIG. 32d is an overlay infrared spectrum of a region of the spectrum showing differences between the dispersion and the component parts. For example, there is a peak at about 1650 cm$^{-1}$ in the glycopyrrolate tosylate spectrum and a peak at about 1658 cm$^{-1}$ in the polyvinyl pyrrolidone spectrum. By comparison, in the solid dispersion spectrum, a single peak appears at about 1664 cm$^{-1}$ indicating the material is not a physical mixture. This is confirmed with FIG. 35 which shows a single glass transition temperature at about 36° C.

The solid 1:1 dispersion of a polyvinyl pyrrolidone polymer of Example 26 and glycopyrrolate tosylate may be characterized by either its infrared spectrum, glass transition temperature or both. For example, the solid dispersion may be characterized by a peak at about 1664 cm$^{-1}$ a glass transition temperature of about 36° C., or both.

Figure 36A:
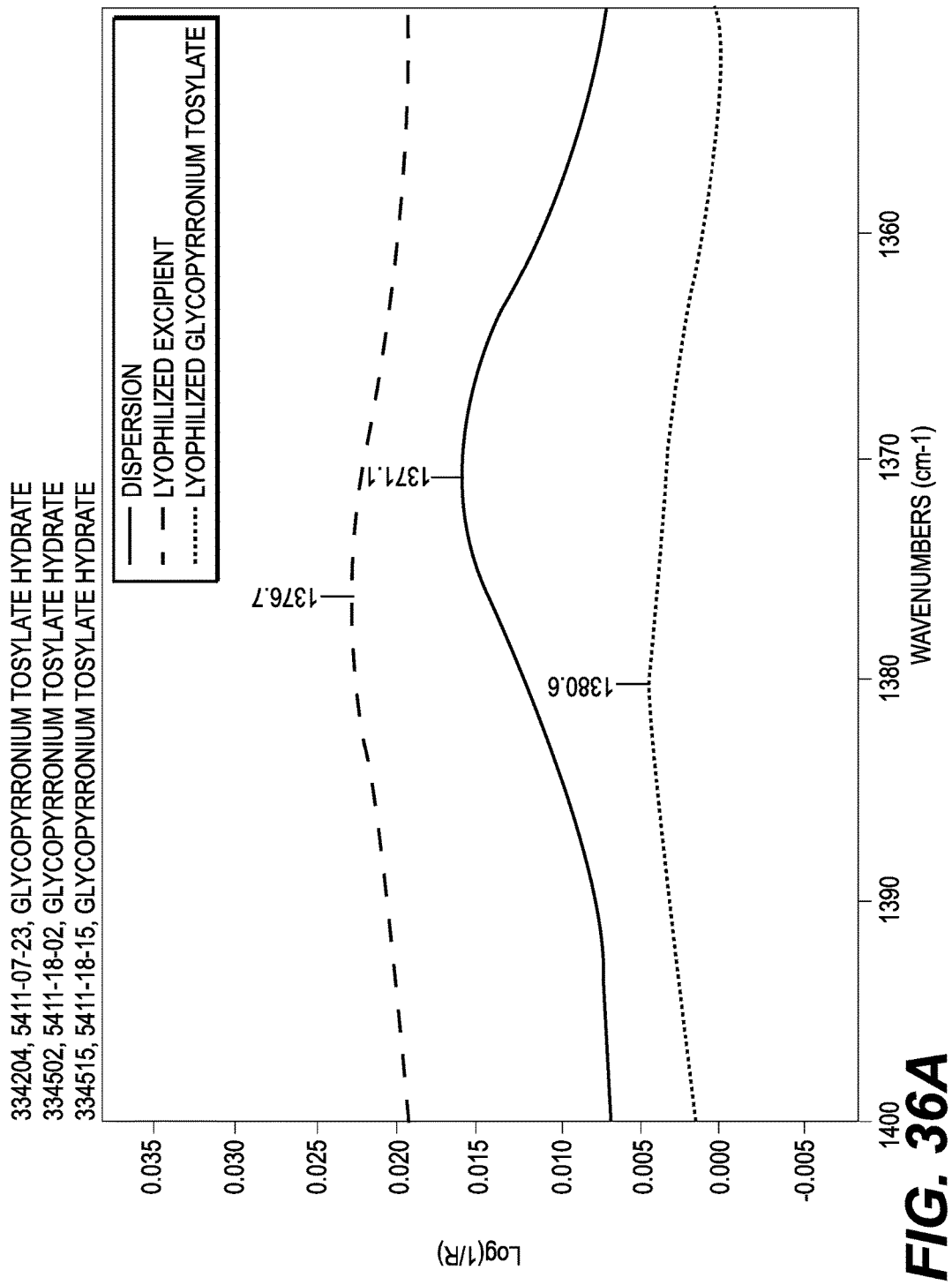
FIG. 36a is an overlay of a portion of the infrared spectrum of a solid dispersion of Kollidon® VA 64:glycopyrrolate tosylate (1:1) and its respective components.
Figure 36B:
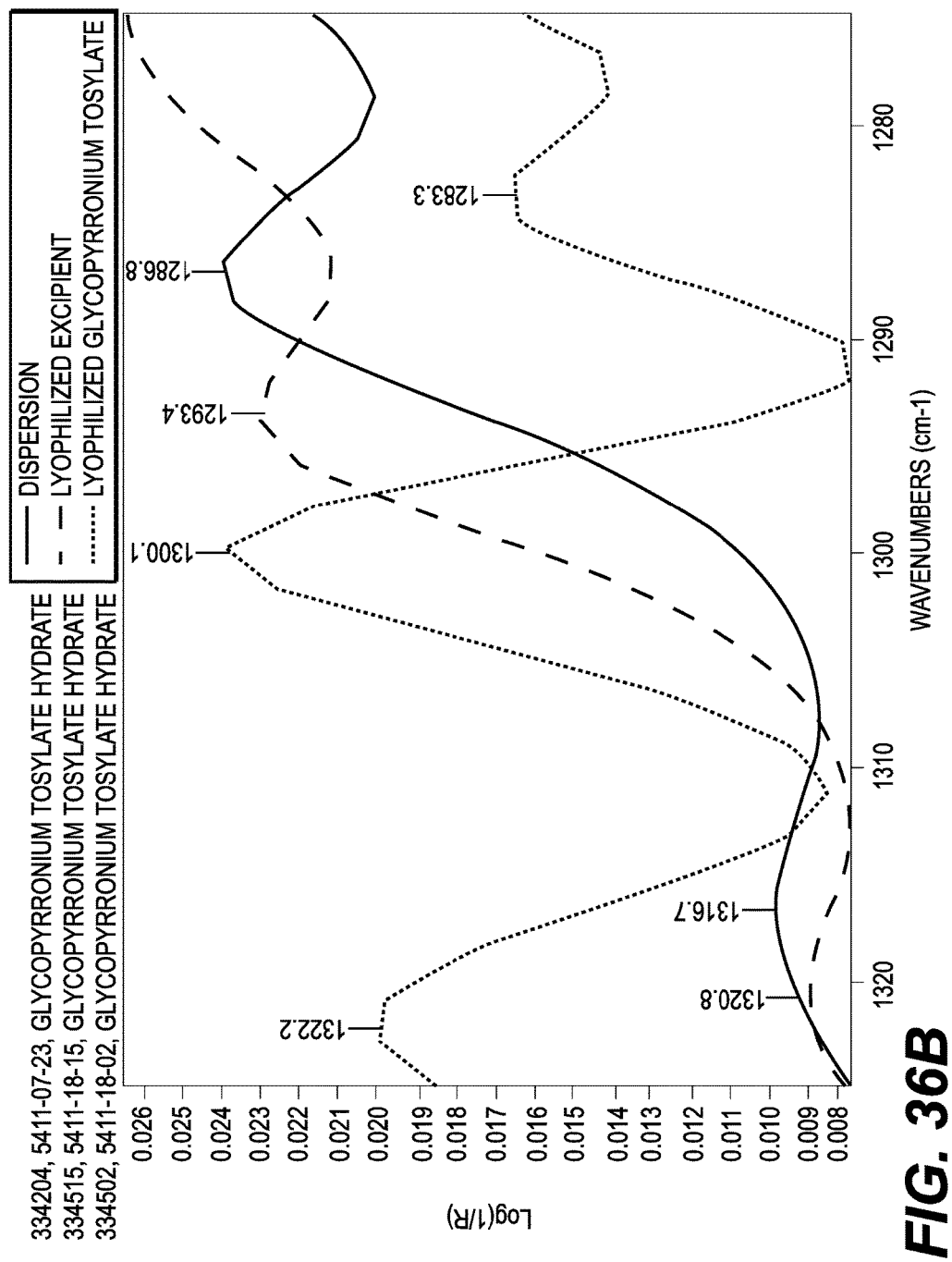
FIG. 36b is an overlay of a portion of the infrared spectrum of a solid dispersion of Kollidon® VA 64:glycopyrrolate tosylate (1:1) and its respective components.
Figure 36C:
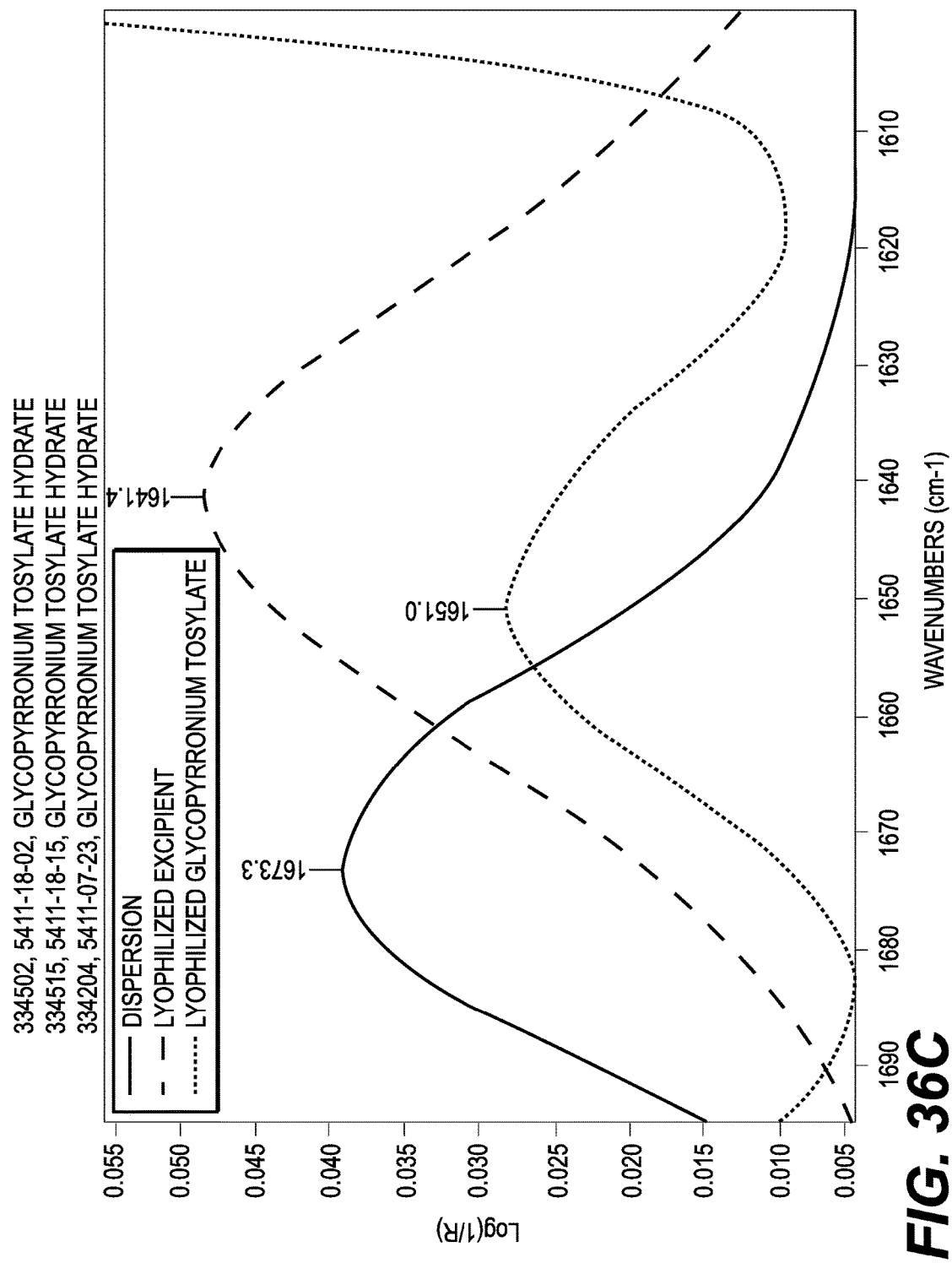
FIG. 36c is an overlay of a portion of the infrared spectrum of a solid dispersion of Kollidon® VA 64:glycopyrrolate tosylate (1:1) and its respective components.
Figure 37:
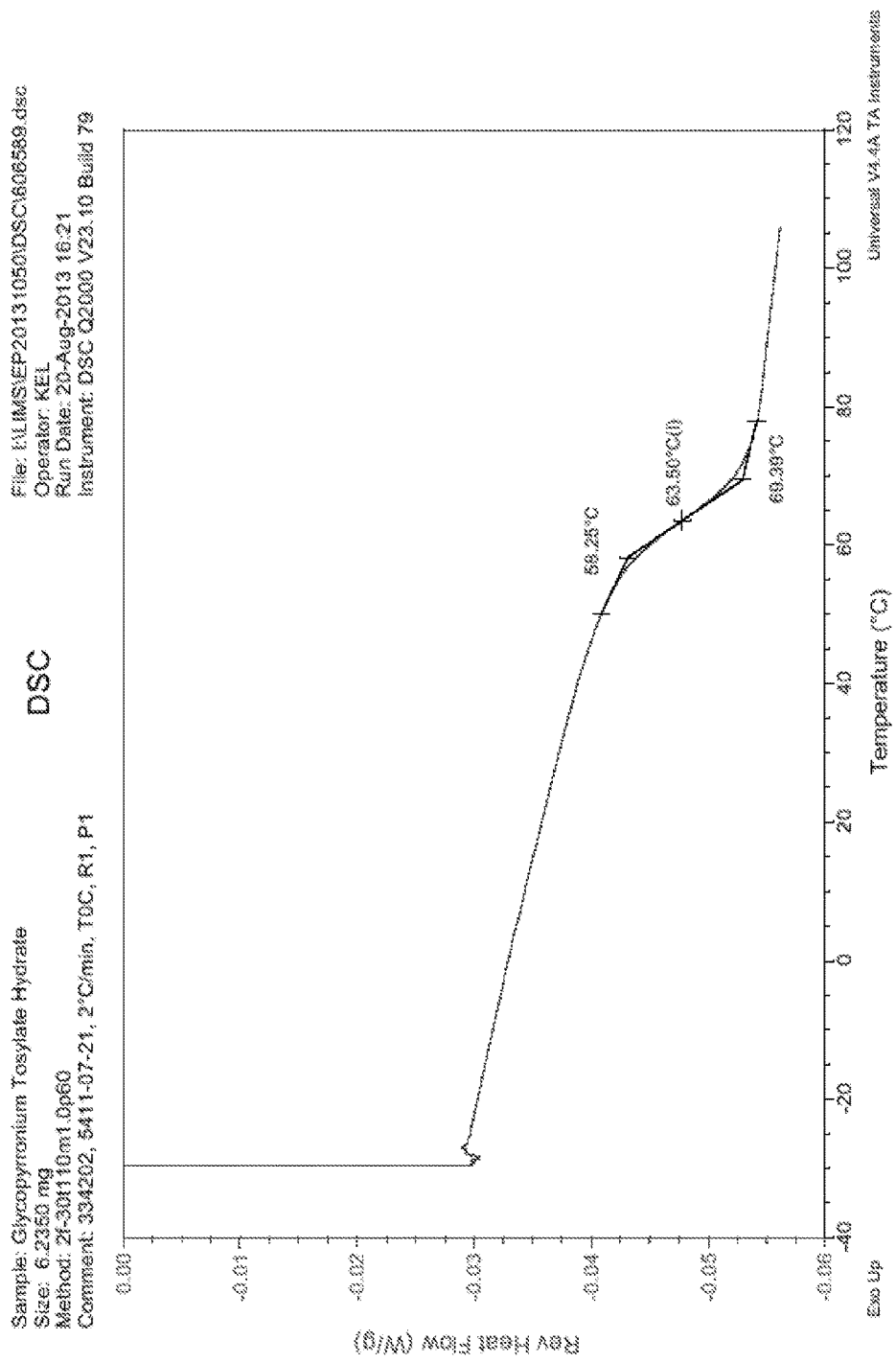
FIG. 37 is the modulated DSC thermogram of a solid dispersion of Kollidon® VA 64:glycopyrrolate tosylate (1:1).

A vinyl pyrrolidone-vinyl acetate copolymer may be used to form a solid dispersion with glycopyrrolate tosylate in, for example, a ratio of about 1 to 1 of a compound of the copolymer to glycopyrrolate by weight. An example of such a preparation can be found in Example 27. FIGS. 36a, 36b, and 36c are overlay infrared spectra of regions of the spectrum showing differences between the dispersion and the component parts. For example, there are peaks at about 1381 cm$^{-1}$, 1300 cm$^{-1}$, 1283 cm$^{-1}$, and 1651 cm$^{-1}$ in the glycopyrrolate tosylate spectrum and peaks at about 1377 cm$^{-1}$, 1293 cm$^{-1}$, and 1641 cm$^{-1}$ in the copolymer spectrum. By comparison, in the solid dispersion spectrum, a single peak appears at about 1371 cm$^{-1}$, 1287 cm$^{-1}$, and 1673 cm$^{-1}$ respectively, indicating the material is not a physical mixture. This is confirmed with FIG. 37 which shows a glass transition temperature at about 64° C.

The solid 1:1 dispersion of a compound of a vinyl pyrrolidone-vinyl acetate copolymer and glycopyrrolate tosylate may be characterized by either its infrared spectrum, glass transition temperature or both. For example, a 1:1 solid dispersion of vinyl pyrrolidone-vinyl acetate copolymer glycopyrrolate tosylate may be characterized by one or more peaks at about 1371 cm$^{-1}$, 1287, and 1673 cm$^{-1}$, a glass transition temperature of about 64° C., or a combination thereof.

Threo glycopyrrolate tosylate may be prepared by treating racemic cyclopentylmandelic acid with racemic 1-methyl-pyrrolidin-3-ol and 1,1' carbonyldiimidazole in a suitable solvent, such as an organic solvent, to form glycopyrrolate base; treating the glycopyrrolate base in a suitable solvent, such as an alcohol, with a resolving acid to form a salt of threo glycopyrrolate; treating the salt of the threo glycopyrrolate salt with a suitable base in a suitable solvent, such as a mixture of organic solvents and water, to form a threo glycopyrrolate base; and treating the threo glycopyrrolate base with p-toluenesulfonic acid methyl ester, also known as methyl tosylate or methyl 4-benzenesulfonate in a suitable solvent, such as an organic solvent, to form threo glycopyrrolate tosylate. Subsequent treatment as disclosed herein may then be used to prepare, for example, Forms C, D, dehydrated D, or amorphous glycopyrrolate tosylate. In the case of Form D, such further treatment may include recrystallization in water. Care should be given when working with tosylate compounds since it is known in the art that aryl sulfonic acids, for example tosylic acid, may react with alcohols to form sulfonate esters, which are alkylating agents. Further, the equilibrium of the reaction is so surprisingly significantly displaced toward the dissociated tosylate anion that, even after spiking such a low amount as 1 ppm of ethyl tosylate into a 3% threo glycopyrrolate tosylate formulation, the ethyl tosylate levels diminish over time under long-term (25° C./60% relative humidity) and accelerated (40° C./75% relative humidity) stability conditions and are no longer detectable within weeks of the spike.

Suitable solvents for the preparation of the glycopyrrolate base include those where the cyclopentylmandelic acid, 1-methylpyrrolidin-3-ol and 1,1' carbonyldiimidazole are soluble such as toluene. The resolving acid is chosen so that the glycopyrrolate base formed, which is a mixture of four isomers, when treated with the resolving acid results in a salt which produces substantially the threo pair of isomers. The resolving acid may be dissolved in solvents such as an alcohol with one example being methanol. This reaction relies on the different solubilities of the salts produced. One such resolving acid is 5-Nitroisophthalic acid and it may be dissolved in methanol. Suitable bases for forming the threo glycopyrrolate base from the salt of the threo glycopyrrolate base and the resolving acid include hydroxides such as sodium hydroxide and such treatment may be done in a mixture of, for example, toluene and water. Treatment of the resulting base with p-toluenesulfonic acid methyl ester results in the desired threo glycopyrrolate tosylate. Suitable solvents include acetone and ethyl acetate. Water recrystallizations may then be used to form Form D of glycopyrrolate tosylate monohydrate. In some embodiments, seeding with Form D may assist in the formation of Form D. The Form D may then be dried in some embodiments. A general scheme for the synthesis of threo glycopyrrolate tosylate can be found in Scheme 1 which shows the ultimate formation of Form D.

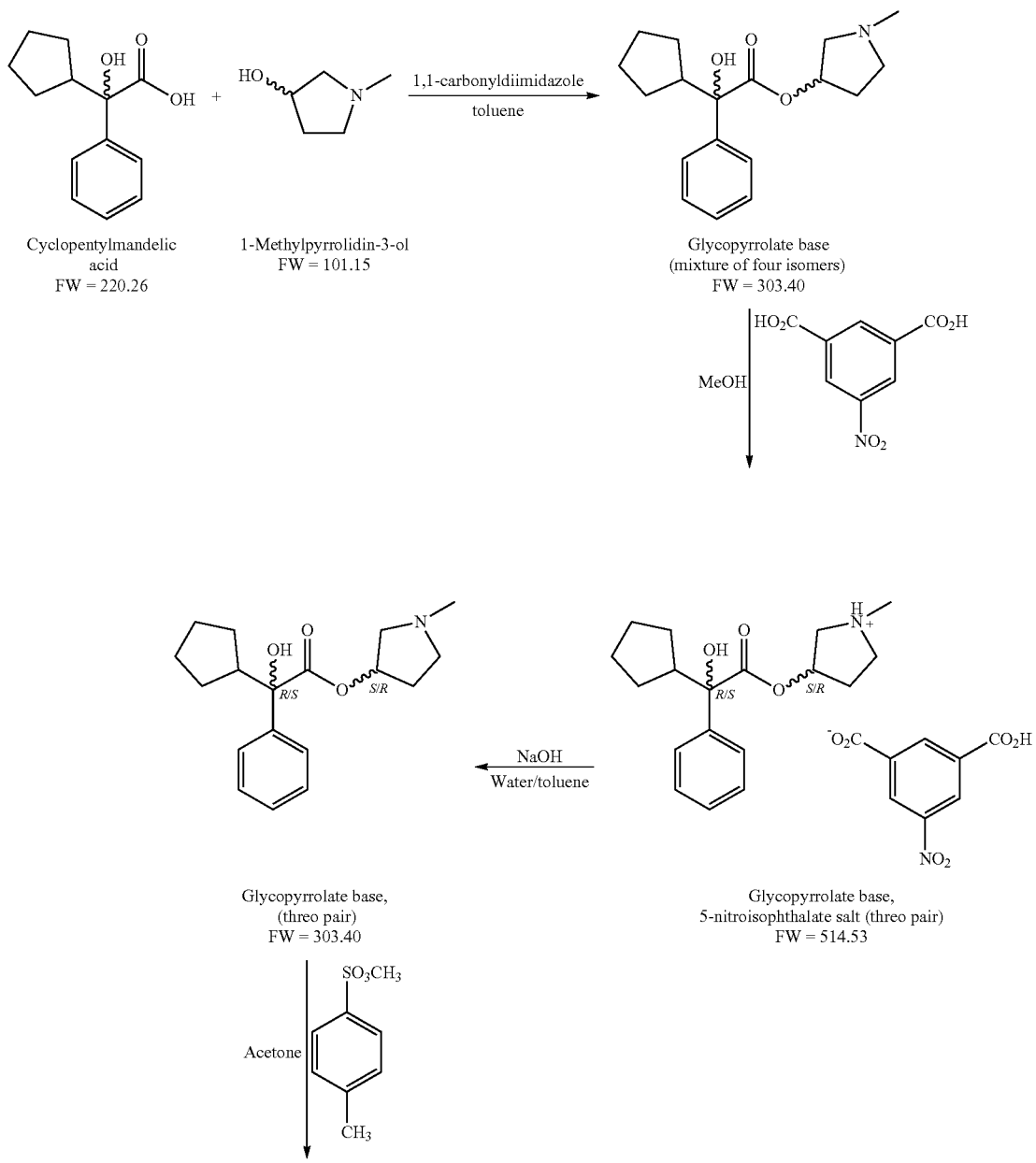

Scheme 1-Flow Diagram synthesis for Threo glycopyrrolate tosylate

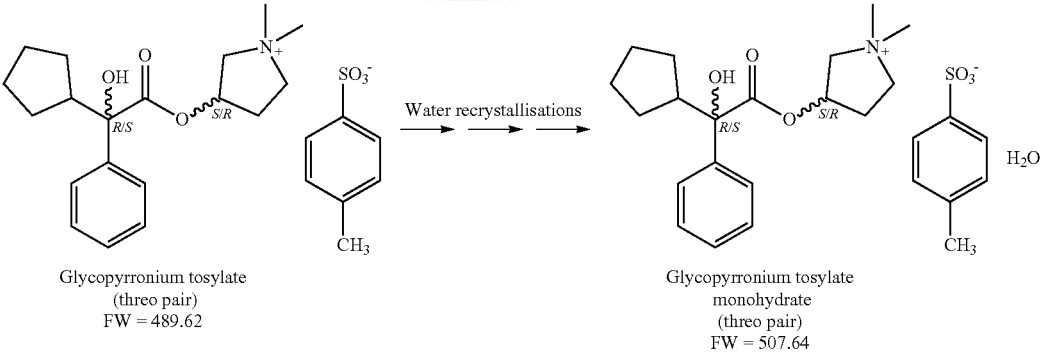

Glycopyrronium tosylate
(threo pair)
FW = 489.62

Water recrystallisations →

Glycopyrronium tosylate
monohydrate
(threo pair)
FW = 507.64

In another embodiment, the present invention provides threo glycopyrrolate tosylate in a topical which is not a solution such as ointment or a cream. An example of such a cream would be cetomacrogol cream. In another embodiment, the topical is a gel.

In one embodiment, the topical comprises threo glycopyrrolate tosylate. In some of these embodiments, the topical further comprises buffers and/or may be in an aqueous solution. When buffers are used, said buffers may be, for example, citric acid and sodium citrate. The buffered topical may further comprise an alcohol such as ethanol.

In another embodiment, the present invention provides a pharmaceutically acceptable solution comprising threo glycopyrrolate tosylate or a solvate thereof and one or more pharmaceutically acceptable additives. Such additives may include such co-solvents as ethanol and one or more pharmaceutically acceptable excipients.

In another embodiment, the pharmaceutically acceptable solution comprising threo glycopyrrolate tosylate or a solvate thereof is aqueous and further comprises one or more buffers. In many embodiments, the pharmaceutically acceptable solution is aqueous. Examples of buffers include, but are not limited to citric acid and sodium citrate dihydrate. The citric acid includes anhydrous citric acid. The solution may also contain one or more alcohols such as ethanol. Dehydrated ethanol is an alcohol that may be used. In one embodiment of the invention, the pharmaceutically acceptable aqueous solution comprising glycopyrrolate tosylate comprises about 0.15% by weight anhydrous citric acid, about 0.06% sodium citrate dihydrate by weight, between about 57 to about 59.5% by weight of dehydrated ethanol, and between about 1% and about 6% by weight glycopyrrolate tosylate.

In yet another embodiment, the topical is prepared so as to be film-forming. In such embodiments, a binding agent used. Examples of binding agents include povidones such as povidone K90. Such film-forming solutions further comprise one or more film-forming agents. Examples of film forming agents include butyl esters of a polyvinylmethylether/maleic anhydride acid copolymer. An example of such a film forming agent is the Gantrez™ ES-425 butyl ester copolymer In yet another embodiment, the aqueous pharmaceutically acceptable solution is prepared so as to be film-forming. In such embodiments, a binding agent used. Examples of binding agents include povidones such as povidone K90. Such film-forming solutions further comprise one or more film-forming agents. Examples of film forming agents include butyl esters of a polyvinylmethylether/maleic anhydride acid copolymer. An example of such a film forming agent is the Gantrez™ ES-425 butyl ester copolymer.

In some embodiments, the pharmaceutically acceptable solution is absorbed onto a carrier. For example, such a carrier may be a pad such as an absorbent pad or nonwoven wipe suitable for holding such solution when in storage as well as for application of the solution to desired areas of skin.

According to the present invention, the absorbent pad can be based on cotton fabric or non-cotton fabric. In one embodiment, the absorbent pad is based on synthetic nonwoven fabric, such as nonwoven rayon and polypropylene fabric. In one embodiment, the absorbent pad is a 75:25 rayon and polypropylene pad.

In some embodiments the absorbent pad material comprises polypropylene. In other embodiments, the absorbent pad is substantially all polypropylene and in others, the pad is 100% polypropylene. Such pads may be nonwoven fabric with the following characteristics:

TABLE 7

Pad Properties

| Physical Property | Characteristics |
|---|---|
| Basis Weight | 1.231-1.254 ounces/yard$^2$ |
| Machine Direction Grab Tensile | 15.495-18.862 lbf (pounds-force) |
| Cross Direction Grab Tensile | 14.425-16.190 lbf |
| Fiber Denier | 2.443-2.569 dpf (denier per filament) |

The pH of a topical such as a solution of glycopyrrolate tosylate, absorbed onto a pad is between 3.5 and 5.5 and often between about 4.0 and 5.0, including about 4 to 4.7 and about 4.1 to 4.6. For a glycopyrrolate tosylate monohydrate topical such as for a pad, the amount of glycopyrrolate tosylate monohydrate solution used in a pad is typically between about 2 g and 4 g including about 2.8 g or other pharmaceutically acceptable amounts.

A topical such as a solution may contain varying weight percents of glycopyrrolate tosylate such as glycopyrrolate tosylate monohydrate. In some embodiments, the weight percent of the glycopyrrolate tosylate, such as glycopyrrolate tosylate monohydrate, is between about 1% and about 4%, including between 1.25% and about 4%, including between 2.5% and 3.75% and including each of about 1.25%, 2.5% and about 3.75%. The weight percents of glycopyrrolate tosylate, including glycopyrrolate tosylate monohydrate, may also be expressed in glycopyrronium weight percent only. For these weight percents, the weight percents may vary between about 0.6% and about 3.2%, including between about 1.6% and about 2.4% and including each of about 0.6%, 1.6% and about 2.4%. These weights are readily converted into weight percents of Form D. For example, 1.6% of glycopyrronium ion translates into 2.5% of Form D. The glycopyrrolate tosylate in any of the embodiments wherein they are absorbed onto the pads or are contained or comprised within the other topicals may be threo glycopyrrolate tosylate. The topicals such as the absorbent pad containing a pharmaceutically acceptable solution can be applied to the area of the body to be treated.

Processes for making aqueous solutions of glycopyrrolate tosylate include treating solid glycopyrrolate tosylate in solution with water so as to dissolve the solid glycopyrrolate tosylate in solution. One may also add one or more buffers and/or alcohol, to the solution. The solution so obtained may then be wetted onto an absorbent pad so that a pharmaceutically acceptable amount of glycopyrrolate tosylate has been absorbed onto the pad. The alcohol may be ethanol such as dehydrated ethanol. The buffers may be citric acid and sodium citrate. In some embodiments, the glycopyrrolate tosylate or a solvate to be dissolved is in a crystalline form. Examples of such crystalline forms include Form C or Form D. In some embodiments, the glycopyrrolate tosylate or a solvate thereof is in an x-ray amorphous form. In other embodiments, pads containing a pharmaceutically acceptable aqueous solution of glycopyrrolate tosylate made by such processes are provided. The wetting may be done while the pad is in a pouch. In many embodiments, the pouch is heat-sealed after wetting. A typical pouch material is laminate containing aluminum foil as a layer. The glycopyrrolate tosylate of the processes herein may be threo glycopyrrolate tosylate.

In another embodiment, a pharmaceutically acceptable aqueous solution of glycopyrrolate tosylate may be prepared by dissolving glycopyrrolate tosylate in a mixture of water with ethanol. One or more pharmaceutically acceptable excipients can be added either prior to or after the addition of the glycopyrrolate tosylate or a solvate thereof and the aqueous solvent. Said glycopyrrolate tosylate may be threo glycopyrrolate tosylate.

The pharmaceutically acceptable solution of glycopyrrolate tosylate or a solvate thereof is therapeutically useful. For example, the pharmaceutically acceptable solution can be used for treating hyperhidrosis or reducing sweating in mammals. The pharmaceutically acceptable solution is typically applied from a pad on which the solution is absorbed. In one embodiment, the present invention provides a method of treating hyperhidrosis in a mammal by topically administering to the skin of the mammal a therapeutically effective amount of a pharmaceutically acceptable solution of glycopyrrolate tosylate or a solvate thereof. In one embodiment, the mammal is a human. The pharmaceutically acceptable solution can be applied to one or several areas or even the whole body including, but not limited to, the hands, e.g., palms; axillae; feet, e.g., soles; groin; face, e.g., cheeks and forehead; and trunk, e.g., back and abdomen, or scalp. In some embodiments, methods of treating primary axillary hyperhidrosis with glycopyrrolate tosylate or a solvate thereof comprising topically administering a therapeutically effective amount of an aqueous glycopyrrolate tosylate solution to the skin of a mammal in need thereof. In many embodiments, such administration may be with an absorbent pad. In other embodiments, methods of treating palmar or plantar hyperhidrosis with glycopyrrolate tosylate or a solvate thereof are provided. Dosing of glycopyrrolate tosylate may be daily. Said pharmaceutically acceptable solution of glycopyrrolate tosylate may be threo glycopyrrolate tosylate.

Instrumental Techniques Used in the Examples
X-ray Powder Diffraction (XRPD)
X-ray Powder Diffraction (XRPD)—Reflection Geometry XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640d) was analyzed to verify the observed position of the Si 111 peak is consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b. The data acquisition parameters for each pattern were: Cu (1.54059 Å) x-ray tube, 45 kV voltage, 40 mA amperage, 3.50-40.00° 2θ scan range, 0.017 or 0.08° 2θ step size, 1835-1947 s collection time, 1.1 or 1.2°/min scan speed, 1/8° divergence slit (DS), 1/4° incident-beam antiscatter slit (SS), 0.0 null revolution time.

X-Ray Powder Diffraction (XRPD)—Transmission Geometry

XRPD patterns were collected with a PANalytical X'Pert PRO MPD diffractometer using an incident beam of Cu radiation produced using an Optix long, fine-focus source. An elliptically graded multilayer mirror was used to focus Cu Kα x-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern were: Cu (1.54059 Å) x-ray tube, 45 kV voltage, 40 mA amperage, 1.0-39.99° 2θ scan range, 0.017° 2θ step size, 717-721 s collection time, 3.3 or 3.2°/min scan speed, ½° divergence slit (DS), null incident-beam antiscatter slit (SS), 1.0 null revolution time.

Variable Temperature X-Ray Powder Diffraction (VT-XRPD)

XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Data were collected and analyzed using Data Collector software v. 2.2b. Prior to the analysis, a silicon specimen (NIST SRM 640d) was analyzed to verify the Si 111 peak position. A specimen of the sample was packed into a nickel-coated copper well. Antiscatter slits (SS) were used to minimize the background generated by air scattering. Soller slits for the incident and diffracted beams were used to minimize broadening from axial divergence. Diffraction patterns were collected using a scanning position-sensitive detector (X'Celerator) located 240 mm from the sample. The data acquisition parameters for each pattern were: Cu (1.54059 Å) x-ray tube, 45 kV voltage, 40 mA amperage, 3.50-26.00° 2θ scan range, 0.008° 2θ step size, 1869 s collection time, 0.7°/min scan speed, ⅛° divergence slit (DS), ¼° incident-beam antiscatter slit (SS), 0.0 null revolution time.

An Anton Paar TTK 450 stage was used to collect in situ XRPD patterns at non-ambient temperatures. The sample was heated with a resistance heater located directly under the sample holder, and the temperature was monitored with a platinum 100 resistance sensor located directly under the specimen. The power to the heater was supplied and controlled by an Anton Paar TCU 100 interfaced with Data Collector.

Infrared Spectroscopy (IR)

IR spectra were acquired on Nicolet 6700 Fourier transform infrared (FT-IR) spectrophotometer (Thermo Nicolet) equipped with an Ever-Glo mid/far IR source, an extended range potassium bromide (KBr) beamsplitter, and a deuterated triglycine sulfate (DTGS) detector. Wavelength verification was performed using NIST SRM 1921b (polystyrene). An attenuated total reflectance (ATR) accessory (Thunderdome™, Thermo Spectra-Tech), with a germanium (Ge) crystal was used for data acquisition. Each spectrum represents 256 co-added scans collected at a spectral resolution of 2 cm−1. A background data set was acquired with a clean Ge crystal. A Log 1/R (R=reflectance) spectrum was obtained by taking a ratio of these two data sets against each other.

Differential Scanning Calorimetry (DSC)

DSC was performed using a TA Instruments 2920 differential scanning calorimeter. Temperature calibration was performed using NIST-traceable indium metal. The sample was placed into an aluminum DSC pan, covered with a lid, and the weight was accurately recorded. A weighed aluminum pan configured as the sample pan was placed on the reference side of the cell. Modulated DSC data (see, e.g., FIG. 23) were obtained on a TA Instruments Q2000 differential scanning calorimeter equipped with a refrigerated cooling system (RCS). Temperature calibration was performed using NIST-traceable indium metal. The sample was placed into an aluminum DSC pan, and the weight was accurately recorded. The pan was covered with a lid perforated with a laser pinhole, and the lid was hermetically sealed. A weighed, crimped aluminum pan was placed on the reference side of the cell. Data were obtained using a modulation amplitude of ±1° C. and a 60 second period with an underlying heating rate of 2° C./minute from −50 to 220° C. The reported glass transition temperatures are obtained from the inflection point of the step change in the reversing heat flow versus temperature curve.

Proton Nuclear Magnetic Resonance (1H NMR)

The solution NMR spectra were acquired with a Varian UNITYINOVA-400 spectrometer. The samples were prepared by dissolving a small amount of sample in DMSO-d6 containing TMS.

Pawley Refinement

Indexing and subsequent Pawley refinement provides the most accurate determination of unit cell volume and cell parameters from XRPD data. These computations were performed using TOPAS 4.2, 2009, Bruker AXS GmbH, Karlsruhe, Germany. The background was modeled using a 3rd order Chebychev polynomial. Peak shape was modeled using Lorentzian crystallite size broadening and axial divergence was modeled using the full axial model. Peak positions were allowed to vary by fitting the unit cell parameters. Whole pattern Pawley refinement was performed on all parameters simultaneously to a convergence of 0.001 in χ2.

Thermogravimetric Analysis (TGA)

TG analyses were performed using a TA Instruments 2950 thermogravimetric analyzer. Temperature calibration was performed using nickel and Alumel™. Each sample was placed in an aluminum pan and inserted into the TG furnace. The furnace was heated under a nitrogen purge. The data acquisition parameters are displayed above each thermogram in the Data section of this report. The method code on the thermogram is an abbreviation for the start and end temperature as well as the heating rate; e.g., 25-350-10 means "from 25 to 350° C., at 10° C./min."

EXAMPLES

Example 1—Salt Screen

Fourteen salts were targeted; however, only six glycopyrrolate salts were successfully isolated and characterized: acetate, benzoate, edisylate, oxalate, hydrogen sulfate, and tosylate. These salts were formed either by (1) reaction of glycopyrrolate bromide with silver salts of salt formers, or (2) reaction of glycopyrrolate acetate with salt former acids.

Example 2—Glycopyrrolate Benzoate

The glycopyrrolate benzoate salt was prepared only once using route (1) from Example 1. Glycopyrrolate benzoate was generated on reacting saturated aqueous solutions of each glycopyrrolate bromide with silver benzoate at approximately 92° C., followed by filtration and subsequent lyophilization of the mother liquor. The material was then recrystallized in acetone/MTBE (½, vol/vol) and sonicated to form white crystalline solids. An XRPD pattern associated with this material is in FIG. 12. Proton NMR showed the presence of equimolar amounts of the glycopyrrolate and benzoate species, as well as water. Thermal analysis of the sample showed a single endotherm with a peak maximum of 79° C. in the DSC thermogram concomitant with a 3.5 wt % loss between 25 and 80° C. in the TG trace. The weight loss was equivalent to approximately one mole of water indicating the formation of a monohydrate.

Example 3—Di-Glycopyrrolate Edisylate

Di-glycopyrrolate Edisylate salt was formed using process (2) from Example 1. A second molar equivalent of glycopyrrolate acetate was added to the reaction mixture of glycopyrrolate acetate and a minor amount of silver acetate and one molar equivalent of 1,2-ethanedisulfonic acid in ethyl acetate/isopropanol (83/17, vol/vol). The mixture was stirred for approximately five minutes before the resulting grey solids were isolated and dried under vacuum at ambient temperature for one day. The dried solids were crystalline with a minor amount of silver acetate by XRPD (FIG. 14). The XRPD pattern was successfully indexed which indicated that the material was composed of a single crystalline phase. Proton NMR spectroscopy confirmed the presence of two moles of glycopyrrolate per mole of edisylate, and water. Thermal analysis of the sample showed a 3.8 wt % loss between 25 and 95° C. in the TG trace and an endotherm with a peak maximum at 103° C. in the DSC thermogram. The mass loss equates to approximately two moles water indicating a dihydrate.

Example 4—Glycopyrrolate Oxalate

Glycopyrrolate oxalate was prepared using process (2) from Example 1. Equimolar amounts of oxalic acid and glycopyrrolate acetate were dissolved in methanol then fast evaporated and dried under vacuum. The resulting glassy, gel-like material was recrystallized by slurrying in ethyl acetate to produce grey solids that were then dried under vacuum before analysis by XRPD and proton NMR spectroscopy. The XRPD pattern can be found in FIG. 16.

Example 5—Glycopyrrolate Hydrogen Sulfate

Glycopyrrolate hydrogen sulfate was prepared as a mixture with a trace amount of silver sulfate using process (2) from Example 1. Equimolar amounts of glycopyrrolate acetate and sulfuric acid were stirred in anhydrous ethyl acetate for approximately one day before the resulting material was isolated and dried under vacuum. The solids were characterized by XRPD, proton NMR spectroscopy, thermal techniques and elemental analysis. The XRPD pattern was unique and contained a trace amount of silver sulfate (FIG. 17). The XRPD pattern was successfully indexed except for the silver sulfate peak at 28.35° 2θ, indicating that the glycopyrrolate hydrogen sulfate salt was composed of a single crystalline phase. The silver sulfate was likely formed from the silver acetate present in the glycopyrrolate acetate starting material. The NMR spectrum was consistent with a 1:1 ratio of a glycopyrrolate and hydrogen sulfate. Thermal analysis showed a major sharp endotherm with a peak maximum at 160° C. and a second endotherm with a peak maximum at 169° C., and a negligible weight loss of 0.2 wt % between 25 and 180° C. Elemental analysis confirmed the anhydrous salt stoichiometry.

Example 6—Glycopyrrolate Tosylate

In a dark room, silver tosylate (3.5 g) was dissolved in water (~100 mL) by sonication. The solution was heated to approximately 40° C. and additional water was added (~15 mL). An equimolar amount of glycopyrrolate bromide (5 g) (mixture of R,S and S,R diastereomers) was added and immediately resulted in a yellow precipitate. The slurry was stirred at approximately 40° C. overnight, and then slowly cooled while stirring to ambient temperature. At ambient temperature, the solids were vacuum filtered and the wet cake was washed three times with approximately 10 mL of water. The mother liquor was collected and filtered two times through a 0.2 μm nylon filter with glass microfiber (GMF). A clear solution was observed after filtration and was lyophilized at approximately −50° C. After 6 days, a mixture of white, needle-like and slightly sticky, glassy solids was observed. Toluene (~20 mL) was added, and the slurry was briefly sonicated and then stirred at ambient temperature. Additional toluene (~80 mL) was added for easier stirring, and the mixture was allowed to stand at ambient conditions for 1 day. Solids of glycopyrrolate tosylate were collected by vacuum filtration and vacuum drying at ambient temperature for 1 day.

Example 7—Preparation of Glycopyrrolate Tosylate

A slurry of equimolar amounts of glycopyrrolate acetate and p-toluenesulfonic acid was prepared in isopropanol (1 mL). The mixture was stirred at ambient temperature. Additional isopropanol (0.5 mL) was added to improve stirring, and the mixture was stirred overnight. Solids of glycopyrrolate tosylate were isolated by vacuum filtration and analyzed.

Example 8—Preparation of Glycopyrrolate Tosylate Form D

Glycopyrrolate tosylate (1.0569 g) made from Example 6 was dissolved in 4 mL ACN/H$_2$O (50/50 vol/vol) by sonication. The solution was filtered through 0.2 μm nylon filter into a clean vial. The solvent was allowed to partially evaporate from an open vial under ambient conditions. Further evaporation was subsequently performed under nitrogen gas flow. A gel resulted which was vacuum dried at 40° C. for 1 day. Toluene (5 mL) was added and the mixture was sonicated for approximately 10 minutes causing white solids to precipitate. The mixture was stirred at ambient temperature for 1 day. The solids were isolated by vacuum filtration and the wet cake was washed with approximately 10 mL of toluene. The solids were vacuum dried at ambient temperature for 1 day. After vacuum drying the solids were placed in a vial which remained uncapped and placed inside a relative humidity chamber (~97%). The chamber was placed inside an oven at 41° C. After 6 days, the solids were analyzed by XRPD showing Form D.

Example 9—Single Crystal Preparation of Form D

Glycopyrrolate tosylate (54.9 mg) made from Example 6 was dissolved in EtOAc/DMF (87/13 vol/vol) at approximately 55° C. at 24 mg/ml. The solution was hot filtered through a 0.2 μm nylon filter into a pre-warmed vial. The vial containing the solution was first placed in a dry ice/acetone bath and then in a freezer (approximately −25 to −10° C.). After 3 days, the solution was re-heated to approximately 50° C. and additional EtOAc was added for 96/4 EtOAc/DMF (vol/vol) at 7 mg/ml. The solution was quickly removed from elevated temperature and placed in the freezer. Solids were isolated by decanting the solvent and drying the solids under ambient conditions.

Single Crystal Data Collection

A colorless chunk of $C_{26}H_{37}NO_7S$ [$C_7H_7O_3S$, $C_{19}H_{28}NO_3$, $H_2O$] having approximate dimensions of 0.23× 0.20×0.18 mm, was mounted on a fiber in random orientation. Preliminary examination and data collection were performed with Cu Kα radiation (λ=1.54184 Å) on a Rigaku Rapid II diffractometer equipped with confocal optics. Refinements were performed using SHELX97.

Example 10—Preparation of Dehydrated Form D

A mixture of glycopyrrolate tosylate solids, including Form C and Form D, and a trace amount of silver tosylate was kept over P$_2$O$_5$ at ambient temperature for 18 days. The resulting solids were composed of a mixture of dehydrated Form D with a trace of silver tosylate as shown by XRPD analysis.

Example 11—Preparation of Form C Glycopyrrolate Tosylate

Glycopyrrolate tosylate Form D, containing trace amounts of Form C and silver tosylate, was heated on an Anton Paar TTK 450 stage and XRPD patterns were collected in situ in the range 3.5-26° (2θ). All heating steps were at approximately 10° C./min. The stage was heated in incremental steps of 20° C. from 25 to 125° C. At each step, an XRPD pattern was collected over approximately 4 minutes. The stage was then heated to 135° C. and an XRPD pattern was collected over approximately 16 minutes and after heating further to 145° C., a pattern was collected in approximately 31 minutes. The sample was subsequently cooled to 25° C. at approximately 24° C./min, upon which a final XRPD pattern was collected over approximately 16 min. The XRPD pattern of this final pattern was indexed as Form C.

Example 12—Preparation of Form C Glycopyrrolate Tosylate

Glycopyrrolate tosylate Form D from Example 6 was heated to an approximate temperature in the range 143-149° C. under a continuous nitrogen purge for approximately 3.3 hours. The vial containing the solids was capped, placed on a lab bench and allowed to cool down to room temperature. At room temperature, the vial was placed in a jar containing $P_2O_5$. The sample was prepared for XRPD analysis under nitrogen which confirmed production of Form C.

Example 13—Preparation of Form C Glycopyrrolate Tosylate

Glycopyrrolate tosylate (59.5 mg) from Example 6 was dissolved in acetone at approximately 50° C. at 27 mg/ml. The solution was hot filtered through a 0.2 µm nylon filter into a pre-warmed vial. The vial was capped and left on the hot plate which was subsequently turned off to allow the sample to cool slowly to ambient temperature. At ambient temperature the solution was stirred causing white solids to precipitate. The solids were isolated by vacuum filtration and the wet cake was washed with approximately 2 ml of acetone. XRPD analysis resulted in Form C.

Example 14—Amorphous Glycopyrrolate Tosylate

Glycopyrrolate tosylate from Example 6 was melted and cooled repeatedly until the majority of the solids had the appearance of a glass by microscopy. XRPD analysis indicated that the "glassy" sample was observed to be amorphous. A 2.2% weight loss was observed by TGA from 25 to 250° C. of the amorphous glycopyrrolate tosylate. The onset of the glass transition temperature was measured at 11.6° C.

Example 15—Preparing Crude Threo Glycopyrrolate Tosylate

Cyclopentylmandelic acid is combined with 1,1'-carbonyldiimidazol in toluene and is heated and stirred. N-methyl-3-pyrriolidinol is added while stirring and heated in toluene. The reaction mixture is then cooled and washed with purified water. The isolate toluene layer is then reduced to a concentrate of the glycopyrrolate base.

5-Nitroisophthalic acid (1 eq.) is dissolved in methanol (20 vol) at room temperature with moderate agitation. The glycopyrrolate base (1 eq.) obtained above is then added. Once crystallization is initiated, the mixture is stirred at room temperature. The solids are then recovered in a filtration centrifuge and washed with methanol. The crude product is then suspended in methanol and stirred at approximately 65° C. for one hour, then cooled to 20° C. and stirred for a further 4 hours. The product is again recovered, washed with methanol, partially dried and discharged as wet glycopyrrolate 5-nitroisophthalate. The ratio of threo:erythro diastereomeric pairs is typically 96:4. The threo-glycopyrrolate base is obtained by treatment of the wet 5-nitroisophthalate salt with aqueous sodium hydroxide and toluene.

The threo-glycopyrrolate base is dissolved in acetone and treated with a slight excess of methyl-p-toluenesulfonate. The completion of reaction is monitored by TLC until the remaining base is NMT 2%. The crude glycopyrronium tosylate is recovered and washed twice with acetone. The wet cake obtained is dried under vacuum at elevated temperature.

Example 16 Pure Threo Glycopyrrolate Tosylate

The product of Example 15 is triturated in purified water and recovered and washed with cold purified water. The wet cake is then dissolved in water with agitation. The solution obtained is cooled and held until crystallization begins. The mixture is then further cooled and agitated and the product is recovered and washed with cold purified water. The product then undergoes a second recrystallization under similar conditions. The product is tray dried at not more than 40° C. without vacuum for a minimum time until the water content is between about 2.5%-4.0%.

Example 17a—Preparing an Aqueous Solution of Glycopyrrolate Tosylate

To a vessel of appropriate size, add purified water, citric acid and sodium citrate dihydrate and dissolve by mixing. Add dehydrated alcohol; initiate mixing and continue to mix until a homogenous clear solution is obtained. Continue mixing and add solid glycopyrrolate tosylate and mix until the glycopyrrolate tosylate is dissolved and the solution is homogenous. The solution should be clear and colorless or pale yellow with a pH of between about 4.0 and about 5.0 at about 25° C.

Example 17b—Preparing an Aqueous Solution of Threo Glycopyrrolate Tosylate Using Form D To a vessel of appropriate size, add purified water, citric acid and sodium citrate dihydrate and dissolve by mixing. Add dehydrated alcohol; initiate mixing and continue to mix until a homogenous clear solution is obtained. Continue mixing and add Form D glycopyrrolate tosylate and mix until the glycopyrrolate tosylate is dissolved and the solution is homogenous. The solution should be clear and colorless or pale yellow with a pH of between about 4.0 and about 5.0 at about 25° C.

Example 18—Filling a Pouch and Pad

Each pouch is formed, heat sealed on three sides; bottom, and outer edges. A pad is folded and cut to size, and with a final fold in half, one pad is inserted into each preformed pouch through the open top. About 2.8 g of the glycopyrrolate tosylate product of Example 15 is added through the open top of each pouch wetting the enclosed pad. The top side of the pouch is heat sealed.

General Preparation of Solid Dispersions

Solutions of excipient and glycopyrrolate tosylate Form D were dissolved in water, ethanol/water or dioxane/water, filtered through a 0.2 µm nylon fiber membrane, dropwise, into a vial submerged in a liquid nitrogen bath. The addition rate of the solution was monitored so that each drop of the sample was frozen prior to the next drop being added. The samples were placed on dry ice and immediately transported to a LABCONCO Triad Series lyophilizer and dried. After drying, the solids were isolated and stored over desiccant in a freezer. All samples were removed from the freezer and warmed to ambient temperature in a desiccator prior to analysis. Attempts were made to limit the amount of time the sample experienced at ambient humidity prior to analysis. Excipients were purchased from commercial suppliers and used as received including: PVP K-29/32 ISP Technologies, Inc. Wayne N. J; Kollicoat I R, Kollidon V A. 64: BASF SE, Ludwigshafen, Germany; HPMCAS: Shin-Etsu Chemical Company Ltd., Tokyo, Japan; PVP K-90: Sigma-Aldrich, Inc., St. Louis Mo., USA. This general procedure was followed in the examples set forth Table 8 below using the weights of excipient, glycopyrrolate tosylate and solvent choice as indicated.

TABLE 8

Solid Dispersion Examples

| Example Number | Excipient (Loading) | Wt. Glycopyrrolate Tosylate (mg) | Wt. Excipient (mg) | Solvent |
|---|---|---|---|---|
| 19 | HPMCAS (1:1) | 79.1 | 79.6 | H₂O/Dioxane [1:3] |
| 20 | Sucrose (9:1) | 10.3 | 89.7 | H₂O |
| 21 | Kollicoat ® IR (1:1) | 82.0 | 80.1 | H₂O |
| 22 | Kollicoat ® IR (9:1) | 10.5 | 90.2 | H₂O |
| 23 | Soluplus ® (1:1) | 78.2 | 79.5 | H₂O/Dioxane [1:1] |
| 24 | PVP K-29/32 (1:1) | 80.4 | 80.5 | H₂O |
| 25 | PVPK-29/32 (8:1) | 11.3 | 89.5 | H₂O |
| 26 | PVP K-90 (1:1) | 79.5 | 80.4 | H₂O/EtOH [5:1] |
| 27 | Kollidon ® VA 64 (1:1) | 78.5 | 79.8 | H₂O |

All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A pharmaceutically acceptable solution comprising:
   a racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate, and
   at least one pharmaceutically acceptable additive;
   between about 57 and about 59.5% by weight dehydrated ethanol,
   wherein the weight percent of said racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate is between about 1% and about 6%; and
   the pH of said pharmaceutically acceptable solution is between 3.5 and 5.5.

2. The pharmaceutically acceptable solution of claim 1, wherein the pH of said pharmaceutically acceptable solution is between about 4.0 and about 5.0.

3. The pharmaceutically acceptable solution of claim 1, wherein the pH of said pharmaceutically acceptable solution is between about 4.0 and about 4.7.

4. The pharmaceutically acceptable solution of claim 1, wherein the pH of said pharmaceutically acceptable solution is between 4.1 and 4.6.

5. The pharmaceutically acceptable solution of claim 2, wherein said pharmaceutically acceptable solution is clear and colorless or pale yellow at a pH of between about 4.0 and about 5.0 at 25° C.

6. The pharmaceutically acceptable solution of claim 1, wherein said pharmaceutically acceptable additive is citric acid, sodium citrate, or a combination thereof as a buffer.

7. The pharmaceutically acceptable solution of claim 1, further comprising at least one pharmaceutically acceptable excipient.

8. The pharmaceutically acceptable solution of claim 1, further comprising povidone as a binding agent and a butyl ester of a polyvinylmethylether/maleic anhydride acid copolymer as a film-forming agent.

9. The pharmaceutically acceptable solution of claim 1, wherein the solution comprises about 0.15% by weight anhydrous citric acid and about 0.06% by weight sodium citrate.

10. The pharmaceutically acceptable solution of claim 9, wherein the weight percent of the racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate is between about 1% and about 4%.

11. The pharmaceutically acceptable solution of claim 9, wherein the weight percent of the racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate is between about 1.25% and about 4%.

12. The pharmaceutically acceptable solution of claim 9, wherein the weight percent of the racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate is between about 2.5% and about 3.75%.

13. The pharmaceutically acceptable solution of claim 11, wherein said weight percent of the racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate is about 1.25%.

14. The pharmaceutically acceptable solution of claim 11, wherein said weight percent of the racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate is about 2.5%.

15. The pharmaceutically acceptable solution of claim 11, wherein said weight percent of the racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate is about 3.75%.

16. A topical composition comprising a racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate and at least one pharmaceutically acceptable additive.

17. The topical composition of claim 16, wherein the weight percent of said a racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate is between about 1% and about 4%.

18. The topical composition of claim 16, wherein the weight percent of said a racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate is between about 1.25% and about 4%.

19. The topical composition of claim 16, wherein the weight percent of said a racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate is between about 2.5% and about 3.75%.

20. The topical composition of claim 16, wherein said topical composition is an ointment, a gel, a lotion, a spray, a cream, a paste, or a wash.

21. The topical composition of claim 16, wherein said topical composition is a patch, a dressing, a mask, a gauze, a bandage, a swab, or a pad.

22. The topical composition of claim 16, wherein said topical composition further comprises ethanol.

23. The topical composition of claim 16, wherein the pH of said topical composition is between 3.5 and 5.5.

24. The topical composition of claim 16, wherein the pH of said topical composition is between about 4.0 and about 5.0.

25. The topical composition of claim 16, wherein the pH of said topical composition is between about 4.0 and about 4.7.

26. The topical composition of claim 16, wherein the pH of said topical composition is between about 4.1 and about 4.6.

27. The topical composition of claim 24, wherein said topical composition is clear and colorless or pale yellow at a pH of between about 4.0 and about 5.0 at 25° C.

28. The topical composition of claim 16, wherein said topical composition further comprises citric acid, sodium citrate, or a combination thereof as a buffer.

29. The topical composition of claim 16, further comprising povidone as a binding agent.

30. The topical composition of claim 29, further comprising a butyl ester of a polyvinylmethylether/maleic anhydride acid copolymer as a film-forming agent.

31. The topical composition of claim 16, wherein the topical composition comprises about 0.15% by weight anhydrous citric acid, about 0.06% by weight sodium citrate, between about 57% to about 59.5% by weight dehydrated ethanol, and between about 1% and about 6% by weight of the racemic mixture of (R)-3-((S)-2-cyclopentyl-2-hydroxy-2-phenylacetoxy)-1,1-dimethylpyrrolidinium 4-methylbenzenesulfonate and (S)-3-((R)-2-cyclopentyl-2-hydroxy-2-phenylacetoxy)-1,1-dimethylpyrrolidinium 4-methylbenzenesulfonate.

32. An absorbent pad containing the topical solution of claim 16 absorbed to the pad.

33. The absorbent pad of claim 32, wherein the absorbent pad comprises polypropylene.

34. The absorbent pad of claim 32, wherein the absorbent pad is nonwoven 100% polypropylene.

35. The absorbent pad of claim 32, wherein the absorbent pad is sealed in a pouch.

36. The absorbent pad of claim 32, wherein the pouch is a laminate containing aluminum foil as a layer.

37. An absorbent pad containing the topical solution of claim 31 absorbed to the pad.

38. The absorbent pad of claim 37, wherein the absorbent pad comprises polypropylene.

39. The absorbent pad of claim 37, wherein the absorbent pad is nonwoven 100% polypropylene.

40. The absorbent pad of claim 37, wherein the absorbent pad is sealed in a pouch.

41. The absorbent pad of claim 37, wherein the pouch is a laminate containing aluminum foil as a layer.

* * * * *